(12) United States Patent
Vidal et al.

(10) Patent No.: US 6,544,298 B1
(45) Date of Patent: Apr. 8, 2003

(54) COMPOSITIONS FOR OXIDATION DYEING KERATIN FIBRES COMPRISING A CATIONIC COUPLER NOVEL CATIONIC COUPLERS THEIR USE FOR OXIDATION DYEING AND DYEING METHODS

(75) Inventors: Laurent Vidal, Paris (FR); Jean-Baptiste Saunier, Paris (FR)

(73) Assignee: L'Oreal (FR)

( * ) Notice: Subject to any disclaimer, the term of this patent is extended or adjusted under 35 U.S.C. 154(b) by 0 days.

(21) Appl. No.: 09/646,645

(22) PCT Filed: Jan. 20, 2000

(86) PCT No.: PCT/FR00/00126
§ 371 (c)(1),
(2), (4) Date: Nov. 21, 2000

(87) PCT Pub. No.: WO00/42979
PCT Pub. Date: Jul. 27, 2000

(30) Foreign Application Priority Data

Jan. 21, 1999 (FR) .............................. 99 00638

(51) Int. Cl.$^7$ ................................. A61K 7/13
(52) U.S. Cl. .................. 8/405; 8/405; 8/406; 8/407; 8/408; 8/409; 8/412; 546/293; 424/269; 430/553
(58) Field of Search ............... 8/405, 406, 407, 8/408, 409, 412; 546/293; 424/269; 430/553

(56) References Cited

U.S. PATENT DOCUMENTS

| | | | |
|---|---|---|---|
| 3,712,158 A | 1/1973 | Kalopissis et al. | 8/11 |
| 4,000,131 A | 12/1976 | Rosenberger et al. | 260/240 R |
| 4,003,699 A | 1/1977 | Rose et al. | 8/10.2 |
| 4,310,693 A | 1/1982 | Fujita et al. | 564/440 |
| 4,430,423 A | 2/1984 | Aoki et al. | 430/384 |
| 4,442,115 A | 4/1984 | Ramsden et al. | 424/269 |
| 4,772,543 A | 9/1988 | Sato et al. | 430/553 |
| 4,823,985 A | 4/1989 | Grollier et al. | 222/1 |
| 4,873,338 A | 10/1989 | Wiesen et al. | 546/293 |
| 4,929,539 A | 5/1990 | Sato et al. | 430/553 |
| 5,061,289 A | 10/1991 | Clausen et al. | 8/405 |
| 5,145,483 A | 9/1992 | Junino et al. | 8/412 |
| 5,380,340 A | 1/1995 | Neunhoeffer et al. | 8/402 |
| 5,766,576 A | 6/1998 | Löwe et al. | 424/62 |

FOREIGN PATENT DOCUMENTS

| | | |
|---|---|---|
| DE | 23 59 399 | 6/1975 |
| DE | 28 46 931 | 5/1979 |
| DE | 30 27 128 | 2/1981 |
| DE | 32 46 238 | 1/1983 |
| DE | 34 14 051 | 10/1984 |
| DE | 253 997 | 2/1988 |
| DE | 36 41 825 | 6/1988 |
| DE | 38 43 892 | 6/1990 |
| DE | 41 33 957 | 4/1993 |
| DE | 195 43 988 | 5/1997 |
| DE | 37 21 215 | 1/1998 |
| EP | 0 065 874 | 12/1982 |
| EP | 0 079 141 | 5/1983 |
| EP | 0 081 321 | 6/1983 |
| EP | 0 115 194 | 8/1984 |
| EP | 0 168 729 | 1/1986 |
| EP | 0 193 051 | 9/1986 |
| EP | 0 303 301 | 2/1989 |
| EP | 0 345 728 | 12/1989 |
| EP | 0 366 542 | 5/1990 |
| EP | 0 579 204 | 1/1994 |
| EP | 0 608 896 | 8/1994 |
| EP | 0 790 240 | 8/1997 |
| EP | WO 99/48856 | * 9/1999 |
| EP | WO 99/48874 | * 9/1999 |
| EP | WO 99/48875 | * 9/1999 |
| FR | 1 596 879 | 7/1970 |
| FR | 2 575 470 | 7/1986 |
| FR | 2 586 913 | 3/1987 |
| FR | 2 733 749 | 11/1996 |
| FR | 2 750 048 | 12/1997 |
| GB | 1 026 978 | 4/1966 |
| GB | 1 153 196 | 5/1969 |
| GB | 2 070 000 | 9/1981 |
| JP | 54-115230 | 9/1979 |
| JP | 59-59656 | 4/1984 |
| JP | 62-108859 | 5/1987 |
| JP | 62-173469 | 7/1987 |
| JP | 63-208562 | 8/1988 |
| JP | 64-2045 | 1/1989 |
| JP | 64-32261 | 2/1989 |
| JP | 1-249739 | 10/1989 |
| JP | 2-19576 | 1/1990 |
| JP | 2-255674 | 10/1990 |
| JP | 7-271075 | 10/1995 |
| JP | 9-110659 | 4/1997 |
| JP | 9-169705 | 6/1997 |
| WO | WO 94/08969 | 4/1994 |
| WO | WO 94/08970 | 4/1994 |
| WO | WO 94/19316 | 9/1994 |
| WO | WO 96/15765 | 5/1996 |

OTHER PUBLICATIONS

Co-pending Application No. 09/646,646; Attorney Docket No. 05725.0766–00000 Title: Novel Cationic 2–acylaminophenols, Their Use as Couplers For Oxidation Dyeing, Compositions Containing Them, and Dyeing Methods Inventor(s): Laurent Vidal et al. U.S. Filing Date: Sep. 20, 2000.

(List continued on next page.)

Primary Examiner—Yogendra N. Gupta
Assistant Examiner—Eisa Elhilo
(74) Attorney, Agent, or Firm—Finnegan, Henderson, Farabow, Garrett & Dunner

(57) ABSTRACT

The subject of the invention is a composition for the oxidation dyeing of keratinous fibers, and in particular human keratinous fibers such as hair, comprising at least one oxidation base and, as coupler, at least one 2-acylaminophenol of formula (I) comprising at least one cationic group Z of formula (II), their use as coupler for the oxidation dyeing of keratinous fibers, oxidation dyeing methods using them, as well as novel cationic 2-acylaminophenols of formula (I').

81 Claims, No Drawings

OTHER PUBLICATIONS

Jacqueline Schoenleber, "Pseudo–formazanes Dérivés du Méthylsulfate de Diméthylbenzoxazolium", Bulletin de la Société chimique de France, Jan. 1966, pp. 400–403.

Lauréano Oliveros et al., "Étude des sels de diméthyl–2,3 benzoxazolium. II. Formazanes", Bulletin de la Société chimique de France, Dec. 1969, pp. 4390–4394.

Zh. Org. Khim., vol. 8, 1972, pp. 2429–2431.

Tina L. Grubb et al., "Intermediates and Monomers for Vapor Phase Deposition and Polybenzoxazoles", Designed Monomers and Polymers, vol. 1, No. 1, 1998, pp. 15–36.

English language Derwent Abstract of DD 253 997, Feb. 10, 1988.

English language Derwent Abstract of DE 34 14 051, Oct. 18, 1984.

English language Derwent Abstract of DE 36 21 215, Oct. 7, 1988.

English language Derwent Abstract of FR 2 575 470, Jul. 4, 1986.

English language Derwent Abstract of FR 2 733 749, Nov. 8, 1996.

English language Derwent Abstract of FR 2 750 048, Dec. 26, 1997.

English language Derwent Abstract of JP 54–115230, Sep. 7, 1979.

English language Derwent Abstract of JP 62–108859, May 20, 1987.

English language Derwent Abstract of JP 62–173469, Jul. 30, 1987.

English language Derwent Abstract of JP 63–208562, Aug. 30, 1988.

English language Derwent Abstract of JP 64–2045, Jan. 6, 1989.

English language Derwent Abstract of JP 64–32261, Feb. 2, 1989.

English language Derwent Abstract of JP 1–249739, Oct. 5, 1989.

English language Derwent Abstract of JP 2–19576, Jan. 23, 1990.

English language Derwent Abstract of JP 2–255674, Oct. 16, 1990.

English language Derwent Abstract of JP 7–271075, Oct. 20, 1995.

English language Derwent Abstract of JP 9–110659, Apr. 28, 1997.

English language Derwent Abstract of JP 9–169705, Jun. 30, 1997.

\* cited by examiner

COMPOSITIONS FOR OXIDATION DYEING KERATIN FIBRES COMPRISING A CATIONIC COUPLER NOVEL CATIONIC COUPLERS THEIR USE FOR OXIDATION DYEING AND DYEING METHODS

The subject of the invention is a composition for the oxidation dyeing of keratinous fibres, and in particular human keratinous fibres such as hair, comprising at least one oxidation base and, as coupler, at least one 2-acylaminophenol of formula (I) comprising at least one cationic group Z of formula (II), their use as coupler for the oxidation dyeing of keratinous fibres, oxidation dyeing methods using them, as well as novel cationic 2-acylaminophenols of formula (I').

It is known to dye keratinous fibres and in particular human hair with dyeing compositions containing oxidation dye precursors, in particular ortho- or para-phenylenediamines, ortho- or para-aminophenols, heterocyclic compounds such as diaminopyrazole derivatives, generally called oxidation bases. Oxidation dye precursors, or oxidation bases, are colourless or weakly coloured compounds which, combined with oxidizing products, can give rise, through a process of oxidative condensation, to coloured or colouring compounds.

It is also known that it is possible to vary the shades obtained with these oxidation bases by combining them with couplers or colour modifiers, the latter being chosen in particular from aromatic meta-diamines, meta-aminophenols, meta-diphenols and certain heterocyclic compounds.

The variety of molecules used in oxidation bases and couplers allows a rich palette of colours to be obtained.

The so-called "permanent" colour obtained using these oxidation dyes must moreover satisfy a number of requirements. Thus, it must be without drawbacks from the toxicological point of view, it must make it possible to obtain shades in the desired intensity and exhibit good resistance towards external agents (light, adverse weather conditions, washing, permanent waving, perspiration, rubbing).

The dyes must also make it possible to cover grey hair and must finally be the least selective possible, that is to say make it possible to obtain the smallest possible differences in colour right along the same keratinous fibre, which may indeed be differently sensitized (i.e. damaged) between its tip and its root.

To obtain red shades, 4-aminophenol is generally used, alone or as a mixture with other bases, and in combination with appropriate couplers, and to obtain blue shades, para-phenylenediamines are normally used. The use of couplers derived from meta-phenylenediamines, in combination with derivatives of para-phenylenediamines, normally leads to blue shades whose fastness is generally poor.

It has already been proposed, in particular in patent FR-A-1,596,879, to use for the oxidation dyeing of keratinous fibres phenolic derivatives substituted at the 2-position with a ureinyl or thioureinyl radical, in combination with derivatives of para-phenylenediamines, in order to obtain shades similar to those obtained with the couplers derived from meta-phenylenediamines. However, the dyeing compositions containing the compounds mentioned in this patent generally lead, on the hair, to colours which are too selective and which lack intensity.

Moreover, it has already been proposed, in particular in patent BE 816,674, to use for the dyeing of keratinous fibres, in combination with derivatives of para-phenylenediamines, phenolic derivatives substituted at the 2-position with an acetyl or urea radical and at the 5-position with a halogen atom, in order to obtain colours ranging from green to green-blue. The fastness to light of the shades obtained on hair using these compositions is generally better than those obtained with dyeing compositions containing one or more meta-phenylenediamines as couplers. However, the fastness to adverse weather conditions and to washing as well as the intensities of the colours obtained are still too weak and constitute, in this respect, major disadvantages for persons skilled in the art.

In addition, there has already been proposed, in particular in patent application EP 0,579,204, to use for dyeing keratinous fibres, noncationic phenolic derivatives substituted at the 2-position with an acylamino, carbamoyl or ureyl radical, and at the 5-position with a $C_1$–$C_4$ alkyl radical, in combination with derivatives of para-phenylenediamine. However, the use of the phenolic derivatives mentioned in this European patent application does not make it possible to obtain a rich palette of colours, and, furthermore, the blue shades generally obtained are not completely satisfactory as regards their resistance to washing and to the action of light.

However, the applicant has now just discovered, completely unexpectedly and surprisingly, that the use, as coupler, of 2-acylaminophenols of formula (I) defined below and comprising at least one cationic group Z of formula (II) as defined below makes it possible to obtain dyeing compositions leading to intense colours in shades ranging from red to blue and exhibiting, furthermore, a remarkable fastness to light, adverse weather conditions, washing, perspiration or alternatively permanent waving.

These discoveries form the basis of the present invention.

The first subject of the invention is therefore a composition for the oxidation dyeing of keratinous fibres, and in particular human keratinous fibres such as hair, characterized in that it contains, in a medium appropriate for dyeing:
- at least one oxidation base, and
- at least one coupler chosen from the compounds of the following formula (I) and their addition salts with an acid:

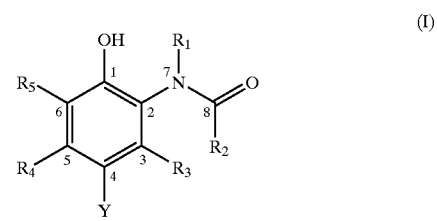

(I)

in which:
$R_1$ represents a hydrogen atom; a group Z as defined below; a radical comprising from 1 to 15 carbon atoms, linear or branched (it being possible for the branch(es) to form one or more carbon-containing rings comprising from 3 to 7 members) which may contain one or more double bonds and/or one or more triple bonds, (the said double bonds possibly leading to aromatic groups), in which one or more carbon atoms may be replaced by an oxygen, nitrogen or sulphur atom or by an $SO_2$ group, and in which the carbon atoms may, independently of each other, be substituted with one or more halogen atoms; it being understood that the said $SO_2$ group is not directly linked to the nitrogen atom at the 7-position carrying the radical $R_1$; the said radical $R_1$ comprising no peroxide bond or diazo, nitro or nitroso radicals;

$R_2$ represents a hydrogen atom; a group Z as defined below; a radical comprising from 1 to 20 carbon atoms, linear or branched (it being possible for the branch(es) to form one or more carbon-containing rings comprising from 3 to 7 members), which may contain one or more double bonds and/or one or more triple bonds (the said double bonds possibly leading to aromatic groups) and in which one or more carbon atoms may be replaced by an oxygen, nitrogen or sulphur atom or by an $SO_2$ group, and in which the carbon atoms may, independently of each other, be substituted with one or more halogen atoms; the said radical $R_2$ containing no peroxide bond or diazo, nitro or nitroso radicals; and it being understood that $R_2$ cannot represent a hydroxyl or thio radical;

the radicals $R_1$ and $R_2$ may, in addition, be linked to form a saturated or unsaturated ring comprising from 5 to 7 members, consisting of carbon, nitrogen, oxygen, sulphur and/or of a C=O group, each member being unsubstituted or substituted with one or two radicals R, which are identical or different, R being a $C_1$–$C_6$ alkyl radical, linear or branched (it being possible for the branch(es) to then form one or more rings comprising from 3 to 6 members), which may contain one or more double bonds and/or one or more triple bonds (the said double bonds possibly leading to aromatic groups), and in which one or more carbon atoms may be replaced by an oxygen, nitrogen or sulphur atom or by an $SO_2$ group, and in which the carbon atoms may, independently of each other, be substituted with one or more halogen atoms; the said radical R containing no peroxide bond or diazo, nitro or nitroso radicals;

$R_3$, $R_4$ and $R_5$, which are identical or different, represent a hydrogen or halogen atom; a group Z as defined below; a radical comprising from 1 to 20 carbon atoms, linear or branched (it being possible for the branch(es) to then form one or more rings comprising from 3 to 7 members), which may contain one or more double bonds and/or one or more triple bonds (the said double bonds possibly leading to aromatic groups), and in which one or more carbon atoms may be replaced by an oxygen, nitrogen or sulphur atom or by an $SO_2$ group, and in which the carbon atoms may, independently of each other, be substituted with one or more halogen atoms; the said radicals $R_3$, $R_4$ and $R_5$ comprising no peroxide bond or diazo, nitro or nitroso radicals; and it being understood that $R_5$ cannot represent a hydroxyl, thio or amino radical or a substituted or unsubstituted sulphonylamino group; and it being understood that the radicals $R_3$, $R_4$ and $R_5$ cannot be linked to the benzene ring of formula (I) by an —NH—NH-bond;

the radicals $R_1$ and $R_3$ may, in addition, be linked to form a saturated ring comprising from 6 to 7 members, consisting of carbon, nitrogen, oxygen, sulphur and/or of a C=O group, each member being unsubstituted or substituted with 1 or 2 radicals R, which are identical or different, R having the same meanings as those indicated above; the said radical R comprising no peroxide bond or diazo, nitro or nitroso radicals;

the radicals $R_2$ and $R_3$ may also be linked to form a saturated ring comprising from 5 to 7 members, consisting of carbon, nitrogen, oxygen, sulphur and/or of a C=O group, each member being unsubstituted or substituted with 1 or 2 radicals R, which are identical or different, R having the same meanings as those indicated above; the said radical R comprising no peroxide bond or diazo, nitro or nitroso radicals;

Y represents a hydrogen or halogen atom; a group —$OR_6$, —$SR_6$ or —NH—$SO_2R_6$ in which $R_6$ represents a $C_1$–$C_6$ alkyl radical, linear or branched (it being possible for the branch(es) to then form one or more rings comprising from 3 to 6 members), unsubstituted or substituted with one or more radicals chosen from the group consisting of a halogen atom, a hydroxyl, $C_1$–$C_4$ alkoxy, amino and $C_1$–$C_4$ aminoalkyl radical; a phenyl radical which is unsubstituted or substituted with one or two radicals chosen from the group consisting of a $C_1$–$C_4$ alkyl, trifluoromethyl, carboxyl, $C_1$–$C_4$ alkoxycarbonyl, halogen, hydroxyl, $C_1$–$C_4$ alkoxy, amino and $C_1$–$C_4$ aminoalkyl radical; or a benzyl radical; and it being understood that Y cannot represent —NH—$SO_2R_6$ when $R_3$ represents a hydroxyl radical;

Z is a cationic group represented by the following formula (II):

(II)

in which:

B represents a radical comprising from 1 to 15 carbon atoms, linear or branched (it being possible for the branch(es) to then form one or more rings comprising from 3 to 7 members), which may contain one or more double bonds and/or one or more triple bonds, the said double bonds possibly leading to aromatic groups, and in which one or more carbon atoms may be replaced with an oxygen, nitrogen or sulphur atom or with an $SO_2$ radical; and in which one or more carbon atoms may, independently of each other, be substituted with one or more halogen atoms or with one or more groups Z; the said radical B containing no peroxide bond or diazo, nitro or nitroso radicals;

D is chosen from the cationic groups of the following formulae (III) and (IV):

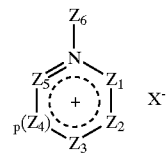
(III)

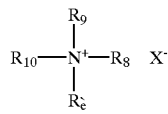
(IV)

in which:

the radical B is linked to the group D by any one of the atoms of the radical D;

n and p can, independently of each other, take the value 0 or 1;

when n=0, then the group of formula (IV) can be linked to the compound of formula (I) directly by the nitrogen atom of the quaternary ammonium, in place of the radical $R_{10}$;

$Z_1$, $Z_2$, $Z_3$ and $Z_4$, independently of each other, represent an oxygen atom; a sulphur atom; a nitrogen atom which is unsubstituted or substituted with a radical $R_{11}$; or a carbon atom which is unsubstituted or substituted with one or two radicals $R_{11}$, which are identical or different;

$Z_5$ represents a nitrogen atom or a carbon atom which is unsubstituted or substituted with a radical $R_{11}$;

$Z_6$ can have the same meanings as those indicated below for the radical $R_{11}$; it being understood that $Z_6$ is different from a hydrogen atom;

the radicals $Z_1$ or $Z_5$ can, in addition, form with $Z_6$ a saturated or unsaturated ring comprising from 5 to 7 members, each member being unsubstituted or substituted with one or two radicals $R_{11}$ which are identical or different;

$R_{11}$ represents a hydrogen atom; a group Z; a radical comprising from 1 to 10 carbon atoms, linear or branched, which may contain one or more double bonds and/or one or more triple bonds, it being possible for the said double bonds to then possibly lead to aromatic groups, and in which one or more carbon atoms may be replaced with an oxygen, nitrogen or sulphur atom, or with an $SO_2$ group, and in which one or more carbon atoms may, independently of each other, be substituted with one or more halogen atoms; the said radical containing no peroxide bond or diazo, nitro or nitroso radicals; it being possible, in addition, for two of the adjacent radicals $Z_1$, $Z_2$, $Z_3$, $Z_4$ and $Z_5$ to form a ring comprising from 5 to 7 members, each member being independently represented by a carbon atom which is unsubstituted or substituted with one or two radicals $R_{11}$ which are identical or different; a nitrogen atom which is unsubstituted or substituted with a radical $R_{11}$; an oxygen atom; or a sulphur atom;

$R_7$, $R_8$, $R_9$ and $R_{10}$, which are identical or different, have the same meanings as those indicated above for the radical $R_{11}$;

it being possible for the radicals $R_7$, $R_8$ and $R_9$ to also form, in pairs with the quaternary nitrogen atom to which they are attached, one or more saturated rings comprising from 5 to 7 members, each member being independently represented by a carbon atom which is unsubstituted or substituted with one or two radicals $R_{11}$ which are identical or different; a nitrogen atom which is unsubstituted or substituted with a radical $R_{11}$; an oxygen atom; or a sulphur atom;

$X^-$ represents an organic or inorganic anion and is preferably chosen from the group consisting of a halide group such as chloride, bromide, fluoride, iodide; a hydroxide; a sulphate; a hydrogen sulphate; a $(C_1-C_6)$alkyl sulphate such as for example a methyl sulphate or an ethyl sulphate; an acetate; a tartrate; an oxalate; a $(C_1-C_6)$alkyl sulphonate such as methyl sulphonate; an aryl sulphonate which is unsubstituted or substituted with a $C_1-C_4$ alkyl radical such as for example a 4-toluoyl sulphonate;

it being understood that at least one of the groups $R_1$ to $R_5$ represents a group Z.

As indicated above, the oxidation dyeing composition containing the compound(s) of formula (I) in accordance with the invention makes it possible to obtain intense colours in shades ranging from red to blue and exhibiting, furthermore, a remarkable fastness to the various treatments to which the keratinous fibres may be subjected. These properties are particularly remarkable in particular as regards the resistance of the colours obtained to the action of light, adverse weather conditions, washing, permanent waving and perspiration.

According to the invention, and when it is indicated that one or more of the carbon atoms of the radical(s) $R_1$ to $R_5$ can be replaced by an oxygen, nitrogen or sulphur atom or by an $SO_2$ group, and/or that the said radicals $R_1$ to $R_5$ may contain one or more double bonds and/or one or more triple bonds, that means that it is possible, by way of example, to make the following conversions:

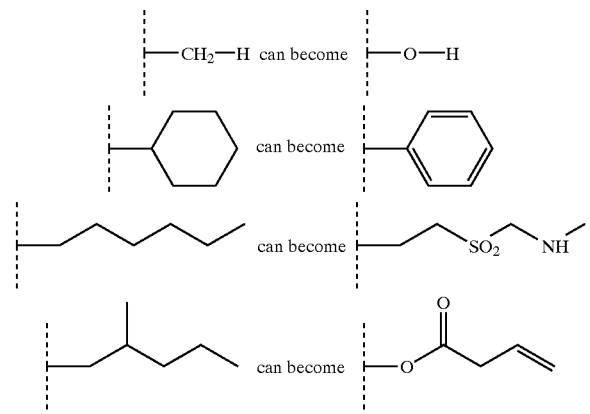

According to the invention, $R_1$ preferably denotes a hydrogen atom, a radical Z; a group $A_1$, $A_2$, $A_3$, $A_4$ or $A_5$, optionally separated from the nitrogen situated at the 7-position onto which the radical $R_1$ is attached by a —(CO)— group.

According to the invention, "group $A_1$" is understood to mean a linear or branched $C_1-C_8$ alkyl radical which may carry one or two double bonds or one triple bond, which may be unsubstituted or substituted with a group chosen from a group $A_2$, $A_4$ and $A_5$, which may be unsubstituted or substituted with one or two groups, which are identical or different, chosen from the N—$(C_1-C_3)$alkylamino, N—$(C_1-C_3)$alkyl-N—$(C_1-C_3)$alkylamino, $(C_1-C_6)$alkoxy, oxo, alkoxycarbonyl, acyloxy, amide, acylamino, ureyl, sulphoxy, sulphonyl, sulphonamido, sulphonylamino, bromo, cyano and carboxyl groups, and which may be unsubstituted or substituted with one or more hydroxyl, fluoro or chloro groups.

"Group $A_2$" is understood to mean an aromatic group of the phenyl or naphthyl type, which may be unsubstituted or substituted with one to three groups, which are identical or different, chosen from the methyl, trifluoromethyl, ethyl, isopropyl, butyl, pentyl, fluoro, chloro, bromo, methoxy, trifluoromethoxy, ethoxy, propyloxy, acetyloxy, acetyl and cyano groups.

"Group $A_3$" is understood to mean heteroaromatic groups chosen from the furanyl, thiophenyl, pyrrolyl, imidazolyl, thiazolyl, oxazolyl, 1,2,3-triazolyl, 1,2,4-triazolyl, isoxazolyl, isothiazolyl, pyrazolyl, pyrazolotriazolyl, pyrazoloimidazolyl, pyrrolotriazolyl, pyrazolopyrimidyl, pyrazolopyridyl, pyridyl, pyrimidyl, benzoimidazolyl, benzoxazolyl, benzothiazolyl, indolyl, indolidinyl, isoindolyl, indazolyl, benzotriazolyl, quinolinyl, benzoimidazolyl and benzopyrimidyl groups, the said groups being unsubstituted or substituted with 1 to 3 radicals chosen from a linear or branched $C_1$–$C_4$ alkyl radical, a $C_1$–$C_4$ monohydroxyalkyl radical, a $C_2$–$C_4$ polyhydroxyalkyl radical, a carboxyl radical, an alkoxycarbonyl radical, a halogen atom, an amido radical, an amino radical and a hydroxyl radical.

"Group $A_4$" is understood to mean a $C_3$–$C_7$ cycloalkyl radical, a norbonyl radical, carrying or otherwise a double bond and unsubstituted or substituted with 1 or 2 radicals chosen from a linear or branched $C_1$–$C_4$ alkyl radical, a $C_1$–$C_4$ monohydroxyalkyl radical, a $C_2$–$C_4$ polyhydroxyalkyl radical, a carboxyl radical, an alkoxycarbonyl radical, a halogen atom, an amido radical, an amino radical and a hydroxyl radical.

"Group $A_5$" is understood to mean a heterocycle chosen from the dihydrofuranyl, tetrahydrofuranyl, butyrolactonyl, dihydrothiophenyl, tetrahydrothiophenyl, tetrahydrothiophenonyl, iminothiolane, dihydropyrrolyl, pyrrolidinyl, pyrrolidinonyl, imidazolidinonyl, imidazolidinethionyl, oxazolidinyl, oxazolidinonyl, oxazolanethione, thiazolidinyl, isothiazolonyl, mercaptothiazolinyl, pyrazolidinonyl, iminothiolane, dioxolanyl, pentalactone, dioxanyl, dihydropyridinyl, piperidinyl, pentalactam, morpholinyl, pyrazoli(di)nyl, pyrimi(di)nyl, pyrazinyl, piperazinyl and azepinyl rings.

Among these substituents, $R_1$ represents more particularly a hydrogen atom; a methyl, ethyl, isopropyl, allyl, phenyl, benzyl, fluorobenzyl, hydroxybenzyl, difluorobenzyl, trifluorobenzyl, chlorobenzyl, bromobenzyl, methoxybenzyl, dimethoxybenzyl, (trifluoromethoxy) benzyl, 3,4-methylenedioxybenzyl, 6-chloropiperonyl, 4-methylthiobenzyl, 4-methylsulphonylbenzyl, 4-acetylaminobenzyl, 4-carboxybenzyl, 1-naphthomethyl or 2-naphthomethyl radical; or a 2-hydroxyethyl, 2-methoxyethyl or 2-ethoxyethyl group.

Still more preferably, $R_1$ represents a hydrogen atom or a methyl radical.

According to the invention, $R_2$ preferably denotes a hydrogen atom, an amino group; a group Z; a group $A_1$, $A_2$, $A_3$, $A_4$ or $A_5$ as defined above, optionally separated from the carbon (at the 8-position) with respect to the amide function of the compound of formula (I) by a group —O—, —NH, —N($C_1$–$C_3$)alkyl-, —(CO)—, —(CO)O— or —(CO)NH—.

Among these substituents, $R_2$ preferably denotes a group Z; a radical chosen from the group (G1) consisting of a methyl, ethyl, propyl, isopropyl, butyl, isobutyl, tert-butyl, pentyl, isopentyl, neopentyl, hexyl; cyclopropyl, cyclobutyl, cyclopentyl, cyclopentylmethyl, 3-cyclopentylpropyl, cyclohexyl, 2-cyclohexylethyl, norborn-2-yl, vinyl, 1-methylvinyl, 2-methylvinyl, 2,2-dimethylvinyl, allyl, 3-butenyl, phenyl, methylphenyl, dimethylphenyl, 2,4,6-trimethylphenyl, 4-ethylphenyl, (trifluoromethyl)phenyl, hydroxyphenyl, methoxyphenyl, ethoxyphenyl, acetoxyphenyl, (trifluoromethoxy)phenyl, aminophenyl, 4-dimethylaminophenyl, fluorophenyl, difluorophenyl, fluoro(trifluoromethyl)phenyl, chlorophenyl, dichlorophenyl, bromophenyl, naphth-1-yl, naphth-2-yl, (2-methoxy)naphth-1-yl, benzyl, 4'-methoxybenzyl, 2',5'-dimethoxybenzyl, 3',4'-dimethoxybenzyl, 4'-fluorobenzyl, 4'-chlorobenzyl, 2-phenylvinyl, (1-naphthyl)methyl, (2-naphthyl)methyl; tetrahydrofuran-2-yl, furan-2-yl, 5-methyl-2-(trifluoromethyl)furan-3-yl, 2-methyl-5-phenylfuran-3-yl, thiophen-2-yl, (thiophen-2-yl)methyl, 3-chlorothiophen-2-yl, 2,5-dichlorothiophen-3-yl, benzothiophen-2-yl, 3-chlorobenzothiophen-2-yl, isoxazol-5-yl, 5-methylisoxazol-3-yl, 3,5-dimethylisoxazol-4-yl, 1,3-dimethylpyrazol-5-yl, 1-ethyl-3-methylpyrazol-5-yl, 1-tert-butyl-3-methylpyrazol-5-yl, 3-tert-butyl-1-methylpyrazol-5-yl, 4-bromo-1-ethyl-3-methylpyrazol-5-yl, indol-3-ylcarboxyl, pyridinyl, chloropyridinyl, dichloropyridinyl, 5-(bromo)pyridin-3-yl, piperazin-2-yl, quinoxal-2-yl, fluoromethyl, difluoromethyl, trifluoromethyl, 1,1,2,2-tetrafluoroethyl, pentafluoroethyl, heptafluoropropyl, 1,1,2,2,3,3,4,4-octafluorobutyl, nonafluorobutyl, chloromethyl, chloroethyl, 1,1-dimethyl-2-chloroethyl, 1,2-dichloroethyl, 1-chloropropyl, 3-chloropropyl, 4-chlorobutyl, hydroxymethyl, methoxymethyl, phenoxymethyl, (4-chlorophenoxy)methyl, benzyloxymethyl, acetoxymethyl, 1,2-dihydroxyethyl, 1-phenoxyethyl, 1-acetoxyethyl, 2-(2-carboxyethoxy)ethyl, 1-phenoxyethyl, 1-acetoxyethyl, methoxycarbonyl, ethoxycarbonyl, (methoxycarbonyl)methyl, 2-carboxyethyl, 2-(methoxycarbonyl)ethyl, 2-carboxycyclopropyl, 2-carboxycyclohexane, methoxy, ethoxy, propoxy, isopropoxy, butoxy, isobutoxy, pentoxy, neopentoxy, hexyloxy, cyclopentyloxy, cyclohexyloxy, vinyloxy, allyloxy, propargyloxy, chloromethoxy, 1-chloroethoxy, 2-methoxyethoxy, 4-chlorobutoxy, phenoxy, 4-methylphenoxy, 4-fluorophenoxy, 4-bromophenoxy, 4-chlorophenoxy, 4-methoxyphenoxy, naphth-2-yloxy, benzyloxy; amino, methylamino, ethylamino, propylamino, isopropylamino, butylamino, cyclohexylamino, allylamino, 2-chloroethylamino, 3-chloropropylamino, carboxymethylamino, phenylamino, fluorophenylamino, (trifluoromethyl)phenylamino, chlorophenylamino, bromophenylamino, 4-acetylphenylamino, methoxyphenylamino, (trifluoromethoxy)phenylamino, naphth-1-ylamino, benzylamino, phenethylamino, pyrid-3-ylamino, dimethylamino, 1-pyrrolidinyl and 4-morpholinyl radical.

When $R_1$ and $R_2$ form a ring, the said ring is preferably chosen from the 2-pyrrolidinon-1-yl, methyl-2-pyrrolidinon-1-yl, 5-carboxy-2-pyrrolidinon-1-yl, 5-methoxycarbonyl-2-pyrrolidinon-1-yl, pyrazolinon-1-yl, succinimid-1-yl, 3,5-diketopyrazolidin-1-yl, oxindolin-1-yl, maleimid-1-yl, isoindole-1,3-dion-2-yl, 2-piperidinon-1-yl and glutarimid-1-yl groups.

Still more preferably, $R_2$ represents a radical chosen from the group (G2) consisting of a methyl, ethyl, propyl, allyl, phenyl, tetrahydrofuran-2-yl, furan-2-yl, thiophen-2-yl, pyridinyl, piperazin-2-yl, fluoromethyl, chloromethyl, 2-chloroethyl, methoxymethyl, acetoxymethyl, 1,2-dihydroxyethyl, methoxycarbonyl, 2-carboxyethyl, methoxy, ethoxy, propoxy, allyloxy, 2-chloroethoxy, 2-methoxyethoxy, amino, ethylamino, allylamino, 2-chloroethylamino, pyridylamino, dimethylamino, 1-pyrrolidinyl or 4-morpholinyl radical; or a group —$D_1$, —E—$D_1$, —O—E—$D_1$, —NH—E—$D_1$, in which —E— represents a —$(CH_2)_q$— arm, q being an integer equal to 1 or 2, and $D_1$ represents a group D' chosen from the 3-methylimidazolidinium-1-yl, 3-(2-hydroxyethyl) imidazolidinium-1-yl, 1,2,4-triazolinium-1-yl, 1,2,4-triazolinium-4-yl, N-($C_1$–$C_4$)alkylpyridinium-2-yl, N-($C_1$–$C_4$)alkylpyridinium-3-yl, N-($C_1$–$C_4$) alkylpyridinium-4-yl, N-(2-hydroxyethyl)pyridinium-2-yl, N-(2-hydroxyethyl)pyridinium-3-yl, N-(2-hydroxyethyl) pyridinium-4-yl, pyridinium-1-yl, tri($C_1$–$C_4$) alkylammonium-N-yl, 1-methylpiperidinium-1-yl and 1,4-dimethylpiperazinium-1-yl groups.

Still more preferably, $R_2$ represents a methyl, methoxymethyl, 2-carboxyethyl, methoxy, amino, ethylamino or 1-pyrrolidinyl radical; a group —$D_1$, —E—$D_1$, —O—E—$D_1$ or —NH—E—$D_1$, in which —E— represents a —$(CH_2)_q$— arm, q=1 to 2 and $D_1$ a group D' as defined below.

According to the invention, $R_3$ and $R_4$, which are identical or different, preferably denote a hydrogen or halogen atom; a hydroxyl or amino group; a group Z; a group $A_1$, $A_4$ or $A_5$ as defined above; a group $A_1$, $A_2$, $A_3$, $A_4$ or $A_5$ as defined above and separated from the phenolic ring of the formula (I) by an oxygen atom or by a group —NH—, —N($C_1$-$C_3$)alkyl-, —O(CO)—, —NH(CO)—, —N($C_1$-$C_3$)alkyl(CO)—, —NH[C=NH]—, —NH(CO)NH—, —NH(CO)N($C_1$-$C_3$)alkyl-, —NH(CO)O—, —NHSO$_2$—, —NHSO$_2$NH— or —NHSO$_2$N($C_1$-$C_3$)alkyl-.

Among these substituents, $R_3$ represents still more preferably a hydrogen or chlorine atom; a group Z; a methyl, hydroxymethyl, methoxymethyl, 1-hydroxyethyl, aminomethyl, methylaminomethyl, hydroxyl, methoxy, acetoxy, amino, methylamino or 2-hydroxyethylamino radical; a group —NH(CO)$R_{12}$ in which $R_{12}$ represents one of the radicals listed in the group (G1) as defined above; a group —NHSO$_2$$R_{13}$, in which $R_{13}$ represents one of the radicals listed in the group (G3) consisting of the methyl, trifluoromethyl, ethyl, 2-chloroethyl, propyl, 3-chloropropyl, isopropyl, butyl, thiophen-2-yl, hydroxyl, ethoxy and dimethylamino radicals.

When $R_1$ and $R_3$ form a ring, together with the nitrogen atom at the 7-position of the compound of formula (I), the —CH$_2$CH$_2$CH$_2$— linkage is preferred for —$R_1R_3$—.

When $R_2$ and $R_3$ form a ring, together with the nitrogen atom at the 7-position of the compound of formula (I), the —CH$_2$—, —C(CH$_3$)$_2$— or —CH$_2$CH$_2$— linkages are preferred for —$R_2R_3$—.

Still more preferably, $R_3$ represents a hydrogen atom; a methyl, hydroxymethyl, aminomethyl, hydroxyl, methoxy, amino or methylamino radical; a methanesulphonylamino group; ethanesulphonylamino; dimethylaminosulphonylamino; a group —NH(CO)$R_{14}$ in which $R_{14}$ represents one of the radicals listed in the group (G2) as defined above; or a group —O—E—D$_2$, —NH—E—D$_2$, —CH$_2$O—E—D$_2$, —CH$_2$NH—E—D$_2$, —CH$_2$NH(CO)—D$_2$, —NH(CO)—D$_2$, —NH(CO)—E—D$_2$, —NH(CO)O—E—D$_2$, —NH(CO)NH—E—D$_2$ or —NH(SO$_2$)—E—D$_2$, in which —E— has the same meaning as that indicated above and D$_2$ represents a group D' as defined above.

Among these substituents, $R_4$ preferably represents a hydrogen or chlorine atom; a group Z; a methyl, ethyl, hydroxymethyl, methoxymethyl, aminomethyl, methylaminomethyl, hydroxyl, methoxy, acetoxy, amino, methylamino, N-piperidino or N-morpholino radical; a group —NH(CO)$R_{15}$ in which $R_{15}$ represents one of the radicals listed in the group (G1) defined above; or a group —NHSO$_2$$R_{16}$ in which $R_{16}$ represents one of the radicals listed in the group (G3) defined above.

Still more preferably, $R_4$ represents a hydrogen or chlorine atom; a methyl, hydroxymethyl, aminomethyl, hydroxyl, methoxy, amino or methylamino radical; a methanesulphonylamino group; ethanesulphonylamino; dimethylaminosulphonylamino; a group —NH(CO)$R_{17}$ in which $R_{17}$ represents one of the radicals listed in the group (G2) defined above; or a group —O—E—D$_3$, —NH—E—D$_3$, —CH$_2$O—E—D$_3$, —CH$_2$NH—E—D$_3$, —CH$_2$NH(CO)—D$_3$, —NH(CO)—D$_3$, —NH(CO)—E—D$_3$, —NH(CO)O—E—D$_3$, —NH(CO)NH—E—D$_3$ or —NH(SO$_2$)—E—D$_3$, in which —E— has the same meaning as indicated above, and D$_3$ represents a group D' as defined above.

According to the invention, $R_5$ is preferably chosen from a hydrogen or halogen atom; a group Z; a group $A_1$, $A_4$ or $A_5$ as defined above; a group $A_1$, $A_2$, $A_3$, $A_4$ or $A_5$ as defined above and separated from the phenolic ring of the compounds of formula (I) by an oxygen or sulphur atom or by a group —NH—, —N($C_1$-$C_3$)alkyl-, —O(CO)—, —NH(CO)—, —N($C_1$-$C_3$)alkyl(O)—, —NH[C=NH]—, —NH(CO)NH—, —NH(CO)N($C_1$-$C_3$)alkyl-, or —NH(CO)O—.

Among these substituents, $R_5$ preferably represents a hydrogen, chlorine, fluorine or bromine atom; a group Z; a methyl, trifluoromethyl, allyl, hydroxymethyl, methoxymethyl, 1-hydroxyethyl, aminomethyl, methylaminomethyl, methoxy, acetoxy or methylamino radical; or a group —NH(CO)$R_{18}$ in which $R_{18}$ represents one of the radicals listed in the group (G1) defined above.

Still more preferably, $R_5$ represents a hydrogen, chlorine or fluorine atom; a methyl, hydroxymethyl, aminomethyl, methoxy or methylamino radical; a group —NH(CO)$R_{19}$ in which $R_{19}$ represents one of the radicals listed in the group (G2) defined above; or a group —O—E—D$_4$, —NH—E—D$_4$, —CH$_2$O—E—D$_4$, —CH$_2$NH—E—D$_4$, —CH$_2$NH(CO)—D$_4$, —NH(CO)—D$_4$, —NH(CO)—E—D$_4$, —NH(CO)O—E—D$_4$, or —NH(CO)NH—E—D$_4$, in which —E— has the same meaning as that indicated above, and D$_4$ represents a group D' as defined above.

According to the invention, Y is preferably chosen from a hydrogen, chlorine, fluorine or bromine atom; a methoxy, ethoxy, propoxy, benzyloxy, phenoxy, —OCH$_2$CH$_2$OCH$_3$; —OCH$_2$CH$_2$N(CH$_3$)$_2$; —OCH$_2$(CO)OH, —OCH$_2$(CO)OCH$_3$, —OCH$_2$(CO)OC$_2$H$_5$, —SCH$_2$CH$_2$CO$_2$H or —NHSO$_2$CH$_3$ group; it being understood that Y cannot represent a group —NHSO$_2$CH$_3$ when $R_3$ represents a hydroxyl radical.

Still more preferably, Y represents a hydrogen or chlorine atom or a methoxy, —OCH$_2$(CO)OH or —OCH$_2$(CO)OCH$_3$ group.

Among the groups D, there may be mentioned, by way of example, the imidazolinium, thiazolinium, oxazolinium, pyrrolinium, 1,2,3-triazolinium, 1,2,4-triazolinium, isoxazolinium, isothiazolinium, imidazolidinium, thiazolidinium, pyrazolinium, pyrazolidinium, oxazolidinium, pyrazoltriazolinium, pyrazoloimidazolinium, pyrrolotriazolinium, pyrazolopyrimidinium, pyrazolopyridinium, pyridinium, pyrimidinium, pyrazinium, triazinium, benzoimidazolinium, benzoxazolinium, benzothiazolinium, indolinium, indolidinium, isoindolinium, indazolinium, benzotriazolinium, quinolinium, tetrahydroquinolinium, benzoimidazolidinium, benzopyrimidinium, tetra($C_1$-$C_4$)-alkylammonium, polyhydroxytetra ($C_1$-$C_4$) alkylammonium, dialkylpiperidinium, dialkylpyrrolidinium, dialkylmorpholinium, dialkylthiomorpholinium, dialkylpiperazinium, azepinium and 1,4-diazabicyclo-[2.2.2]octanium groups.

Still more preferably, D represents a 3-methylimidazolidinium-1-yl, 3-(2-hydroxyethyl)imidazolidinium-1-yl, 1,2,4-triazolinium-1-yl, 1,2,4-triazolinium-4-yl, N-($C_1$-$C_4$)alkylpyridin-2-yl, N-($C_1$-$C_4$)alkylpyridin-3-yl, N-($C_1$-$C_4$)alkylpyridin-4-yl, N-(2-hydroxyethyl)pyridin-2-yl, N-(2-hydroxyethyl)pyridin-3-yl, N-(2-hydroxyethyl)pyridin-4-yl, pyridin-1-yl, tri($C_1$-$C_4$)alkylammonium-N-yl, 1-methylpiperidinium-1-yl, thiazolinium-3-yl or 1,4-dimethylpiperazinium-1-yl groups.

Among the compounds of formula (I), there are particularly preferred those in which:

i)

$R_1$ represents a hydrogen atom;

$R_2$ represents a group —$D_1$, —E—$D_1$, —O—E—$D_1$, —NH—E—$D_1$, as defined above; or a radical chosen from the group (G4) consisting of a methyl, methoxymethyl, 2-carboxyethyl, methoxy, amino, ethylamino or 1-pyrrolidinyl radical;

$R_3$ represents a hydroxyl, amino or methylamino radical; a group —NH(CO)$R_{20}$ in which $R_{20}$ represents one of the radicals listed in the group (G4) defined above; a methanesulphonylamino, ethanesulphonylamino or dimethylaminosulphonylamino group; a group —O—E—$D_2$, —NH—E—$D_2$, —NH(CO)—$D_2$, —NH(CO)—E—$D_2$, —NH(CO)O—E—$D_2$, —NH(CO)NH—E—$D_2$ or —NH(SO$_2$)—E—$D_2$, as defined above;

$R_4$ represents a hydrogen or chlorine atom, or a methyl group;

$R_5$ represents a hydrogen, chlorine or fluorine atom, or a methyl group;

Y represents a hydrogen or chlorine atom; a methoxy or —OCH$_2$(CO)OCH$_3$ group; it being understood that at least one of the groups $R_2$ and $R_3$ contains a group Z;

ii)
$R_1$ represents a hydrogen atom;

$R_2$ represents a group —$D_1$, —E—$D_1$, —O—E—$D_1$ or —NH—E—$D_1$, as defined above; or one of the radicals listed in the group (G4) defined above;

$R_3$ represents a hydrogen atom; or a methyl radical;

$R_4$ represents a hydroxyl, amino, methylamino, methanesulphonylamino, ethanesulphonylamino or dimethylaminosulphonylamino radical; a group —NH(CO)$R_{21}$ in which $R_{21}$ represents one of the radicals listed in the group (G4) defined above; or a group —O—E—$D_3$, —NH—E—$D_3$, —NH(CO)—$D_3$, —NH(CO)—E—$D_3$, —NH(CO)O—E—$D_3$, —NH(CO)NH—E—$D_3$ or —NH(SO$_2$)—E—$D_3$, as defined above;

$R_5$ represents a hydrogen, chlorine or fluorine atom; or a methyl, methoxy or methylamino group;

Y represents a hydrogen or chlorine atom; a methoxy or —OCH$_2$(CO)OCH$_3$ group; it being understood that at least one of the groups $R_2$ and $R_4$ contains a group Z;

iii)
$R_1$ represents a hydrogen atom;

$R_2$ represents one of the radicals listed in the group (G4) defined above; or a group —$D_1$, —E—$D_1$, —O—E—$D_1$, —NH—E—$D_1$, as defined above;

$R_3$ represents a hydrogen atom; or a methyl radical;

$R_4$ represents a hydrogen or chlorine atom; a methyl radical; or a methoxy or methylamino group;

$R_5$ represents a group —NH(CO)$R_{22}$ in which $R_{22}$ represents one of the radicals listed in the group (G4) defined above; or a group —O—E—$D_4$, —NH—E—$D_4$, —NH(CO)—$D_4$, —NH(CO)—E—$D_4$, —NH(CO)O—E—$D_4$ or —NH(CO)NH—E—$D_4$, as defined above;

Y represents a hydrogen or chlorine atom; or a methoxy or —OCH$_2$(CO)OCH$_3$ group; it being understood that at least one of the groups $R_2$ and $R_5$ contains a group Z;

iv)
$R_1$ represents a hydrogen atom;

$R_2$ represents a group —$D_1$, —E—$D_1$, —O—E—$D_1$ or —NH—E—$D_1$, as defined above;

$R_3$ represents a hydrogen atom; or a methyl radical;

$R_4$ represents a hydrogen or chlorine atom; or a methyl radical;

$R_5$ represents a hydrogen, chlorine or fluorine atom; or a methyl group;

Y represents a hydrogen or chlorine atom; or a methoxy or —OCH$_2$(CO)OCH$_3$ group.

Among the compounds of formula (I) above, there may be mentioned most particularly:

3-[(2-Hydroxyphenylcarbamoyl)methyl]-1-methyl-3H-imidazol-1-ium chloride;

3-[(2-Hydroxy-3-(2-(3-methyl-1H-imidazol-3-ium-1-yl)acetylamino)phenylcarbamoyl)methyl]-1-methyl-3H-imidazol-1-ium dichloride;

3-[(2-Hydroxy-4-(2-(3-methyl-1H-imidazol-3-ium-1-yl)acetylamino)phenylcarbamoyl)methyl]-1-methyl-3H-imidazol-1-ium dichloride;

3-[(2-Hydroxy-4-methylphenylcarbamoyl)methyl]-1-methyl-3H-imidazol-1-ium chloride;

3-[(2-Hydroxy-4-aminophenylcarbamoyl)methyl]-1-methyl-3H-imidazol-1-ium chloride;

3-[(2-Hydroxy-4-acetylaminophenylcarbamoyl)methyl]-1-methyl-3H-imidazol-1-ium chloride;

3-[(2-Hydroxy-4-methoxycarbonylaminophenylcarbamoyl)methyl]-1-methyl-3H-imidazol-1-ium chloride;

3-[(3-Hydroxy-4-acetylaminophenylcarbamoyl)methyl]-1-methyl-3H-imidazol-1-ium chloride;

3-[(3-Hydroxy-4-methoxycarbonylaminophenylcarbamoyl)methyl]-1-methyl-3H-imidazol-1-ium chloride;

3-[(2-Hydroxy-5-chlorophenylcarbamoyl)methyl]-1-methyl-3H-imidazol-1-ium chloride;

3-[(2-Hydroxy-4-methyl-5-chlorophenylcarbamoyl)methyl]-1-methyl-3H-imidazol-1-ium chloride;

3-[(2-Hydroxy-4-amino-5-chlorophenylcarbamoyl)methyl]-1-methyl-3H-imidazol-1-ium chloride;

3-[(2-Hydroxy-4-acetylamino-5-chlorophenylcarbamoyl)methyl]-1-methyl-3H-imidazol-1-ium chloride;

3-[(2-Hydroxy-4-methoxycarbonylamino-5-chlorophenylcarbamoyl)methyl]-1-methyl-3H-imidazol-1-ium chloride;

3-[(3-Hydroxy-4-acetylamino-5-chlorophenylcarbamoyl)methyl]-1-methyl-3H-imidazol-1-ium chloride;

3-[(3-Hydroxy-4-methoxycarbonylamino-6-chlorophenylcarbamoyl)methyl]-1-methyl-3H-imidazol-1-ium chloride;

3-[(2-Hydroxy-5-methoxyphenylcarbamoyl)methyl]-1-methyl-3H-imidazol-1-ium chloride;

3-[(2-Hydroxy-4-methyl-5-methoxyphenylcarbamoyl)methyl]-1-methyl-3H-imidazol-1-ium chloride;

3-[(2-Hydroxy-4-amino-5-methoxyphenylcarbamoyl)methyl]-1-methyl-3H-imidazol-1-ium chloride;

3-[(2-Hydroxy-4-acetylamino-5-methoxyphenylcarbamoyl)methyl]-1-methyl-3H-imidazol-1-ium chloride;

3-[(2-Hydroxy-4-methoxycarbonylamino-5-methoxyphenylcarbamoyl)methyl]-1-methyl-3H-imidazol-1-ium chloride;

3-[(3-Hydroxy-4-acetylamino-6-methoxyphenylcarbamoyl)methyl]-1-methyl-3H-imidazol-1-ium chloride;

3-[(3-Hydroxy-4-methoxycarbonylamino-6-methoxyphenylcarbamoyl)methyl]-1-methyl-3H-imidazol-1-ium chloride;

3-[(2-Hydroxy-6-aminophenylcarbamoyl)methyl]-1-methyl-3H-imidazol-1-ium chloride;

3-[(2-Hydroxy-6-acetylaminophenylcarbamoyl)methyl]-1-methyl-3H-imidazol-1-ium chloride;

3-[(2-Hydroxy-4,6-diaminophenylcarbamoyl)methyl]-1-methyl-3H-imidazol-1-ium chloride;

3-[(2-Hydroxy-4-acetylamino-6-aminophenylcarbamoyl)methyl]-1-methyl-3H-imidazol-1-ium chloride;

3-[(2-Hydroxy-3,5-dichloro-4-methylphenylcarbamoyl)methyl]-1-methyl-3H-imidazol-1-ium chloride;

3-[(2-Hydroxy-3,5-dichloro-4-aminophenylcarbamoyl)methyl]-1-methyl-3H-imidazol-1-ium chloride;

3-[(2-Hydroxy-3,5-dichloro-4-acetylaminophenylcarbamoyl)methyl]-1-methyl-3H-imidazol-1-ium chloride;
3-[(2-Hydroxy-3,5-dichloro-4-methoxycarbonylaminophenylcarbamoyl)methyl]-1-methyl-3H-imidazol-1-ium chloride;
3-[(2-Hydroxy-3-acetylaminophenylcarbamoyl)methyl]-1-methyl-3H-imidazol-1-ium chloride;
1-[(2-Hydroxyphenylcarbamoyl)methyl]pyridinium chloride;
1-[(2-Hydroxy-3-(2-(pyridinium-1-yl)acetylamino)phenylcarbamoyl)methyl]pyridinium dichloride;
1-[(2-Hydroxy-4-(2-(pyridinium-1-yl)acetylamino)phenylcarbamoyl)methyl]pyridinium dichloride;
1-[(2-Hydroxy-4-methylphenylcarbamoyl)methyl]pyridinium chloride;
1-[(2-Hydroxy-4-aminophenylcarbamoyl)methyl]pyridinium chloride;
1-[(2-Hydroxy-4-acetylaminophenylcarbamoyl)methyl]pyridinium chloride;
1-[(2-Hydroxy-4-methoxycarbonylaminophenylcarbamoyl)methyl]pyridinium chloride;
1-[(3-Hydroxy-4-acetylaminophenylcarbamoyl)methyl]pyridinium chloride;
1-[(3-Hydroxy-4-methoxycarbonylaminophenylcarbamoyl)methyl]pyridinium chloride;
1-[(2-Hydroxy-5-chlorophenylcarbamoyl)methyl]pyridinium chloride;
1-[(2-Hydroxy-4-methyl-5-chlorophenylcarbamoyl)methyl]pyridinium chloride;
1-[(2-Hydroxy-4-amino-5-chlorophenylcarbamoyl)methyl]pyridinium chloride;
1-[(2-Hydroxy-4-acetylamino-5-chlorophenylcarbamoyl)methyl]pyridinium chloride;
1-[(2-Hydroxy-4-methoxycarbonylamino-5-chlorophenylcarbamoyl)methyl]pyridinium chloride;
1-[(3-Hydroxy-4-acetylamino-6-chlorophenylcarbamoyl)methyl]pyridinium chloride;
1-[(3-Hydroxy-4-methoxycarbonylamino-6-chlorophenylcarbamoyl)methyl]pyridinium chloride;
1-[(2-Hydroxy-5-methoxyphenylcarbamoyl)methyl]pyridinium chloride;
1-[(2-Hydroxy-4-methyl-5-methoxyphenylcarbamoyl)methyl]pyridinium chloride;
1-[(2-Hydroxy-4-amino-5-methoxyphenylcarbamoyl)methyl]pyridinium chloride;
1-[(2-Hydroxy-4-acetylamino-5-methoxyphenylcarbamoyl)methyl]pyridinium chloride;
1-[(2-Hydroxy-4-methoxycarbonylamino-5-methoxyphenylcarbamoyl)methyl]pyridinium chloride;
1-[(3-Hydroxy-4-acetylamino-6-methoxyphenylcarbamoyl)methyl]pyridinium chloride;
1-[(3-Hydroxy-4-methoxycarbonylamino-6-methoxyphenylcarbamoyl)methyl]pyridinium chloride;
1-[(2-Hydroxy-6-aminophenylcarbamoyl)methyl]pyridinium chloride;
1-[(2-Hydroxy-6-acetylaminophenylcarbamoyl)methyl]pyridinium chloride;
1-[(2-Hydroxy-4,6-diaminophenylcarbamoyl)methyl]pyridinium chloride;
1-[(2-Hydroxy-4-acetylamino-6-aminophenylcarbamoyl)methyl]pyridinium chloride;
1-[(2-Hydroxy-3,5-dichloro-4-methylphenylcarbamoyl)methyl]pyridinium chloride;
1-[(2-Hydroxy-3,5-dichloro-4-aminophenylcarbamoyl)methyl]pyridinium chloride;
1-[(2-Hydroxy-3,5-dichloro-4-acetylaminophenylcarbamoyl)methyl]pyridinium chloride;
1-[(2-Hydroxy-3,5-dichloro-4-methoxycarbonylaminophenylcarbamoyl)methyl]pyridinium chloride;
1-[(2-Hydroxy-3-acetylaminophenylcarbamoyl)methyl]pyridinium chloride;
1-[(2-Hydroxyphenylcarbamoyl)methyl]-1,4-dimethylpiperazin-1-ium chloride;
1-[(2-Hydroxy-3-(2-(1,4-dimethylpiperazin-1-ium-1-yl)acetyl)aminophenylcarbamoyl)methyl]-1,4-dimethylpiperazin-1-ium dichloride;
1-[(2-Hydroxy-4-(2-(1,4-dimethylpiperazin-1-ium-1-yl)acetyl)aminophenylcarbamoyl)methyl]-1,4-dimethylpiperazin-1-ium dichloride;
1-[(2-Hydroxy-4-methylphenylcarbamoyl)methyl]-1,4-dimethylpiperazin-1-ium chloride;
1-[(2-Hydroxy-4-aminophenylcarbamoyl)methyl]-1,4-dimethylpiperazin-1-ium chloride;
1-[(2-Hydroxy-4-acetylaminophenylcarbamoyl)methyl]-1,4-dimethylpiperazin-1-ium chloride;
1-[(2-Hydroxy-4-methoxycarbonylaminophenylcarbamoyl)methyl]-1,4-dimethylpiperazin-1-ium chloride;
1-[(3-Hydroxy-4-acetylaminophenylcarbamoyl)methyl]-1,4-dimethylpiperazin-1-ium chloride;
1-[(3-Hydroxy-4-methoxycarbonylaminophenylcarbamoyl)methyl]-1,4-dimethylpiperazin-1-ium chloride;
1-[(2-Hydroxy-5-chlorophenylcarbamoyl)methyl]-1,4-dimethylpiperazin-1-ium chloride;
1-[(2-Hydroxy-4-methyl-5-chlorophenylcarbamoyl)methyl]-1,4-dimethylpiperaziln-1-ium chloride;
1-[(2-Hydroxy-4-amino-5-chlorophenylcarbamoyl)methyl]-1,4-dimethylpiperazin-1-ium chloride;
1-[(2-Hydroxy-4-acetylamino-5-chlorophenylcarbamoyl)methyl]-1,4-dimethylpiperazin-1-ium chloride;
1-[(2-Hydroxy-4-methoxycarbonylamino-5-chlorophenylcarbamoyl)methyl]-1,4-dimethylpiperazin-1-ium chloride;
1-[(3-Hydroxy-4-acetylamino-6-chlorophenylcarbamoyl)methyl]-1,4-dimethylpiperazin-1-ium chloride;
1-[(3-Hydroxy-4-methoxycarbonylamino-6-chlorophenylcarbamoyl)methyl]-1,4-dimethylpiperazin-1-ium chloride;
1-[(2-Hydroxy-5-methoxyphenylcarbamoyl)methyl]-1,4-dimethylpiperazin-1-ium chloride;
1-[(2-Hydroxy-4-methyl-5-methoxyphenylcarbamoyl)methyl]-1,4-dimethylpiperazin-1-ium chloride;
1-[(2-Hydroxy-4-amino-5-methoxyphenylcarbamoyl)methyl]-1,4-dimethylpiperazin-1-ium chloride;
1-[(2-Hydroxy-4-acetylamino-5-methoxyphenylcarbamoyl)methyl]-1,4-dimethylpiperazin-1-ium chloride;
1-[(2-Hydroxy-4-methoxycarbonylamino-5-methoxyphenylcarbamoyl)methyl]-1,4-dimethylpiperazin-1-ium chloride;
1-[(3-Hydroxy-4-acetylamino-6-methoxyphenylcarbamoyl)methyl]-1,4-dimethylpiperazin-1-ium chloride;
1-[(3-Hydroxy-4-methoxycarbonylamino-6-methoxyphenylcarbamoyl)methyl]-1,4-dimethylpiperazin-1-ium chloride;
1-[(2-Hydroxy-6-aminophenylcarbamoyl)methyl]-1,4-dimethylpiperazin-1-ium chloride;
1-[(2-Hydroxy-6-acetylaminophenylcarbamoyl)methyl]-1,4-dimethylpiperazin-1-ium chloride;
1-[(2-Hydroxy-4,6-diaminophenylcarbamoyl)methyl]-1,4-dimethylpiperazin-1-ium chloride;
1-[(2-Hydroxy-4-acetylamino-6-aminophenylcarbamoyl)methyl]-1,4-dimethylpiperazin-1-ium chloride;
1-[(2-Hydroxy-3,5-dichloro-4-methylphenylcarbamoyl)methyl]-1,4-dimethylpiperazin-1-ium chloride;

1-[(2-Hydroxy-3,5-dichloro-4-aminophenylcarbamoyl)
methyl]-1,4-dimethylpiperazin-1-ium chloride;
1-[(2-Hydroxy-3,5-dichloro-4-
acetylaminophenylcarbamoyl)methyl]-1,4-
dimethylpiperazin-1-ium chloride;
1-[(2-Hydroxy-3,5-dichloro-4-
methoxycarbonylaminophenylcarbamoyl)methyl]-1,4-
dimethylpiperazin-1-ium chloride;
1-[(2-Hydroxy-3-acetylaminophenylcarbamoyl)methyl]-1,
4-dimethylpiperazin-1-ium chloride; and their addition
salts with an acid.

The compound(s) of formula (I) in accordance with the invention and/or the or their addition salt(s) with an acid preferably represent from 0.0005 to 12% by weight approximately of the total weight of the dyeing composition and still more preferably from 0.005 to 6% by weight approximately of this weight.

The nature of the oxidation base(s) which can be used in the dyeing composition in accordance with the invention is not critical. They are preferably chosen from the oxidation bases conventionally used in oxidation dyeing and among which there may be mentioned in particular para-phenylenediamines, bisphenylalkylenediamines, para-aminophenols, ortho-aminophenols and heterocyclic bases.

Among the para-phenylenediamines, there may be mentioned more particularly by way of example para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, and their addition salts with an acid.

Among the para-phenylenediamines mentioned above, there are most particularly preferred para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and their addition salts with an acid.

Among the bisphenylalkylenediamines, there may be mentioned more particularly by way of example N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,5-dioxaoctane, and their addition salts with an acid.

Among the para-aminophenols, there may be mentioned more particularly by way of example para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and their addition salts with an acid.

Among the ortho-aminophenols, there may be mentioned more particularly by way of example 2-aminophenol, 2-amino-5-methylphenol, 2-amino-6-methylphenol, 5-acetamido-2-aminophenol, and their addition salts with an acid.

Among the heterocyclic bases, there may be mentioned more particularly by way of example pyridine derivatives, pyrimidine derivatives and pyrazole derivatives.

Among the pyridine derivatives, there may be mentioned more particularly the compounds described for example in Patents GB 1,026,978 and GB 1,153,196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and their addition salts with an acid.

Among the pyrimidine derivatives, there may be mentioned more particularly the compounds described for example in German Patent DE 2,359,399 or Japanese Patents JP 88-169,571 and JP 91-10659 or Patent Application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and the pyrazolopyrimidine derivatives such as those mentioned in patent application FR-A-2,750,048 and among which there may be mentioned pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-amrinopyrazolo[1,5-a]pyrimidin-7-ylamino)ethanol, 2-(7-aminopyrazolo[1,5-a]pyrimidin-3-ylamino) ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)-(2-hydroxyethyl)amino]ethanol, 5,6-dimethylpyrazolo[1,5-a]pyrimidin-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, 3-amino-5-methyl-7-imidazolylpropylaminopyrazolo[1,5-a]pyrimidine, their tautomeric forms, when a tautomeric equilibrium exists, and their addition salts with an acid.

Among the pyrazole derivatives, there may be mentioned more particularly the compounds described in Patents DE 3,843,892, DE 4,133,957 and Patent Applications WO 94/08969, WO 94/08970, FR-A-2,733,749 and DE 195 43 988 such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3- hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl) amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl) amino-1-methylpyrazole, and their addition salts with an acid.

According to the invention, the dyeing compositions containing one or more para-phenylenediamines and/or one or more heterocyclic oxidation bases are particularly preferred.

The oxidation base(s) preferably represent from 0.0005 to 12% by weight approximately of the total weight of the dyeing composition, and still more preferably from 0.005 to 6% by weight approximately of this weight.

The dyeing composition in accordance with the invention may also contain, in addition to the compound(s) of formula (I) above, one or more additional couplers which may be chosen from the couplers conventionally used in oxidation dyeing and among which there may be mentioned in particular meta-phenylenediamines, meta-aminophenols, meta-diphenols and heterocyclic couplers such as, for example, indole derivatives, indoline derivatives, pyridine derivatives and pyrazolones, and their addition salts with an acid.

These couplers are more particularly chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy) benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one, 1-phenyl-3-methylpyrazol-5-one, and their addition salts with an acid.

When they are present, these additional couplers preferably represent from 0.0001 to 10% by weight approximately of the total weight of the dyeing composition and still more preferably from 0.005 to 5% by weight approximately of this weight.

In general, the addition salts with an acid which can be used in the context of the dyeing compositions of the invention (compounds of formula (I), oxidation bases and additional couplers) are chosen in particular from hydrochlorides, hydrobromides, sulphates, citrates, succinates, tartrates, lactates and acetates.

The medium appropriate for dyeing (or carrier) generally consists of water or of a mixture of water and at least one organic solvent for solubilizing the compounds which might not be sufficiently soluble in water. By way of organic solvent, there may be mentioned for example lower $C_1-C_4$ alkanols such as ethanol and isopropanol; glycerol; glycols and glycol ethers such as 2-butoxyethanol, propylene glycol, monomethyl ether of propylene glycol, monoethyl ether and monomethyl ether of diethylene glycol, as well as aromatic alcohols such as benzyl alcohol or phenoxyethanol, similar products and mixtures thereof.

The solvents may be present in proportions preferably of between 1 and 40% by weight approximately relative to the total weight of the dyeing composition, and still more preferably between 5 and 30% by weight approximately.

The pH of the dyeing composition in accordance with the invention is generally between 3 and 12 approximately, and preferably between 5 and 11 approximately. It can be adjusted to the desired value by means of acidifying or alkalinizing agents normally used in dyeing keratinous fibres.

Among the acidifying agents, there may be mentioned, by way of example, inorganic or organic acids such as hydrochloric acid, orthophosphoric acid, sulphuric acid, carboxylic acids such as acetic acid, tartaric acid, citric acid, lactic acid and sulphonic acids.

Among the alkalinizing agents, there may be mentioned, by way of example, aqueous ammonia, alkali metal carbonates, alkanolamines such as mono-, di- and triethanolamines as well as their derivatives, sodium or potassium hydroxides and the compounds of the following formula (V):

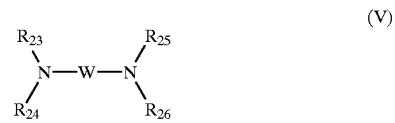

in which W is a propylene residue which is unsubstituted or substituted with a hydroxyl group or a $C_1-C_6$ alkyl radical; $R_{23}$, $R_{24}$, $R_{25}$ and $R_{26}$, which are identical or different, represent a hydrogen atom, a $C_1-C_6$ alkyl or $C_1-C_6$ hydroxyalkyl radical.

The oxidation dyeing compositions in accordance with the invention may also contain at least one direct dye, in particular for modifying the shades or enriching them with glints.

The dyeing composition in accordance with the invention may also contain various adjuvants, conventionally used in hair dyeing compositions, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetrating agents, sequestering agents, perfumes, buffers, dispersing agents, conditioning agents such as for example modified or unmodified, volatile or nonvolatile silicones, film-forming agents, ceramides, preservatives, opacifying agents.

Of course, persons skilled in the art will be careful to choose this or these possible additional compound(s) such that the advantageous properties which are intrinsically attached to the oxidation dyeing composition in accordance with the invention are not, or not substantially, impaired by the addition(s) envisaged.

The dyeing composition according to the invention may be provided in various forms, such as in the form of liquids, creams, gels, or in any other form appropriate for dyeing keratinous fibres, and in particular human hair.

The subject of the invention is also a method of oxidation dyeing of keratinous fibres, and in particular human keratinous fibres such as hair, using the dyeing composition as defined above.

According to this method, at least one dyeing composition as defined above is applied to the fibres, the colour being developed at acidic, neutral or alkaline pH with the aid of an oxidizing agent which is added just at the time of use to the dyeing composition or which is present in an oxidizing composition applied simultaneously or sequentially.

According to a preferred embodiment of the dyeing method of the invention, the dyeing composition described above is preferably mixed, at the time of use, with an oxidizing composition containing, in a medium appropriate for dyeing, at least one oxidizing agent present in a sufficient quantity to develop a colour. The mixture obtained is then applied to the keratinous fibres and allowed to act for 3 to 50 minutes approximately, preferably 5 to 30 minutes approximately, after which they are rinsed, washed with shampoo, rinsed again and dried.

The oxidizing agent may be chosen from the oxidizing agents conventionally used for the oxidation dyeing of keratinous fibres, and among which there may be mentioned hydrogen peroxide, urea peroxide, alkali metal bromates, persalts such as perborates and persulphates, and enzymes such as peroxidases, laccases, tyrosinases and oxidoreductases among which there may be mentioned in particular pyranose oxidases, glucose oxidases, glycerol oxidases, lactate oxidases, pyruvate oxidases and uricases.

The pH of the oxidizing composition containing the oxidizing agent as defined above is such that after mixing with the dyeing composition, the pH of the resulting composition applied to the keratinous fibres preferably varies between 3 and 12 approximately, and still more preferably between 5 and 11. It is adjusted to the desired value by means of acidifying or alkalinizing agents normally used for dyeing keratinous fibres and as defined above.

The oxidizing composition as defined above may also contain various adjuvants conventionally used in hair-dyeing compositions and as defined above.

The composition which is finally applied to the keratinous fibres may be provided in various forms, such as in the form of liquids, creams, gels or in any other form appropriate for dyeing keratinous fibres, and in particular human hair.

Another subject of the invention is a multicompartment device or dyeing "kit" or any other multicompartment packaging system in which a first compartment contains the dyeing composition as defined above and a second compartment contains the oxidizing composition as defined above. These devices may be equipped with a means which makes it possible to deliver the desired mixture to the hair, such as the devices described in patent FR-2,586,913 in the name of the applicant.

Some compounds of formula (I) are novel per se and thereby constitute another subject of the invention. These novel compounds, as well as their addition salts with an acid, correspond to the following formula (I)':

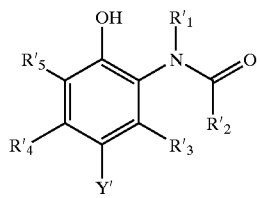

(I)' in which R'$_1$, R'$_2$, R'$_3$, R'$_4$, R'$_5$ and Y can have the same meanings as those indicated above for R$_1$, R$_2$, R$_3$, R$_4$, R$_5$ and Y, in which at least one of the groups R'$_1$ to R'$_5$ represents a group Z' which can have the same meanings as those indicated above for the group Z; excluding the following compounds:

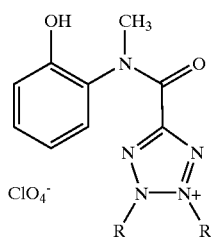

in which R represents a 4-methyl-C$_6$H$_4$, 4-chloro-C$_6$H$_4$ or 2-ethoxy-C$_6$H$_4$ radical

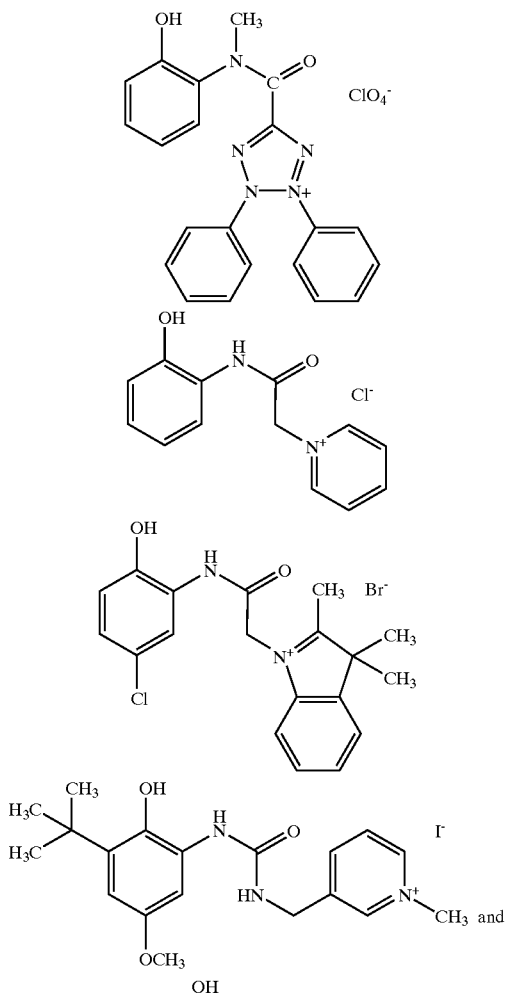

which are known in the photographic or medical field, see in particular the documents Bull. Soc. Chim. Fr. (1966), 400–3; Bull. Soc. Chim. Fr. (1969), 4390–4; Zh. Org. Khim. (1972), 8, 2429–31; Des. Monomers Polym. (1998), 1, 15–36; and the patent applications EP 0,303,301; JP 07,271,075 and EP 0,790,240.

Among the compounds of formula (I') in accordance with the invention, there may be mentioned in particular:

3-[(2-Hydroxyphenylcarbamoyl)methyl]-1-methyl-3H-imidazol-1-ium chloride;

3-[(2-Hydroxy-3-(2-(3-methyl-1H-imidazol-3-ium-1-yl)acetylamino)phenylcarbamoyl)methyl]-1-methyl-3H-imidazol-1-ium dichloride;

3-[(2-Hydroxy-4-(2-(3-methyl-1H-imidazol-3-ium-1-yl)acetylamino)phenylcarbamoyl)methyl]-1-methyl-3H-imidazol-1-ium dichloride;

3-[(2-Hydroxy-4-methylphenylcarbamoyl)methyl]-1-methyl-3H-imidazol-1-ium chloride;

3-[(2-Hydroxy-4-aminophenylcarbamoyl)methyl]-1-methyl-3H-imidazol-1-ium chloride;

3-[(2-Hydroxy-4-acetylaminophenylcarbamoyl)methyl]-1-methyl-3H-imidazol-1-ium chloride;

3-[(2-Hydroxy-4-methoxycarbonylaminophenylcarbamoyl)
methyl]-1-methyl-3H-imidazol-1-ium chloride;
3-[(3-Hydroxy-4-acetylaminophenylcarbamoyl)methyl]-1-
methyl-3H-imidazol-1-ium chloride;
3-[(3-Hydroxy-4-methoxycarbonylaminophenylcarbamoyl)
methyl]-1-methyl-3H-imidazol-1-ium chloride;
3-[(2-Hydroxy-5-chlorophenylcarbamoyl)methyl]-1-
methyl-3H-imidazol-1-ium chloride;
3-[(2-Hydroxy-4-methyl-5-chlorophenylcarbamoyl)
methyl]-1-methyl-3H-imidazol-1-ium chloride;
3-[(2-Hydroxy-4-amino-5-chlorophenylcarbamoyl)methyl]-
1-methyl-3H-imidazol-1-ium chloride;
3-[(2-Hydroxy-4-acetylamino-5-chlorophenylcarbamoyl)
methyl]-1-methyl-3H-imidazol-1-ium chloride;
3-[(2-Hydroxy-4-methoxycarbonylamino-5-
chlorophenylcarbamoyl)methyl]-1-methyl-3H-imidazol-
1-ium chloride;
3-[(3-Hydroxy-4-acetylamino-5-chlorophenylcarbamoyl)
methyl]-1-methyl-3H-imidazol-1-ium chloride;
3-[(3-Hydroxy-4-methoxycarbonylamino-6-
chlorophenylcarbamoyl)methyl]-1-methyl-3H-imidazol-
1-ium chloride;
3-[(2-Hydroxy-5-methoxyphenylcarbamoyl)methyl]-1-
methyl-3H-imidazol-1-ium chloride;
3-[(2-Hydroxy-4-methyl-5-methoxyphenylcarbamoyl)
methyl]-1-methyl-3H-imidazol-1-ium chloride;
3-[(2-Hydroxy-4-amino-5-methoxyphenylcarbamoyl)
methyl]-1-methyl-3H-imidazol-1-ium chloride;
3-[(2-Hydroxy-4-acetylamino-5-methoxyphenylcarbamoyl)
methyl]-1-methyl-3H-imidazol-1-ium chloride;
3-[(2-Hydroxy-4-methoxycarbonylamino-5-
methoxyphenylcarbamoyl)methyl]-1-methyl-3H-
imidazol-1-ium chloride;
3-[(3-Hydroxy-4-acetylamino-6-methoxyphenylcarbamoyl)
methyl]-1-methyl-3H-imidazol-1-ium chloride;
3-[(3-Hydroxy-4-methoxycarbonylamino-6-
methoxyphenylcarbamoyl)methyl]-1-methyl-3H-
imidazol-1-ium chloride;
3-[(2-Hydroxy-6-aminophenylcarbamoyl)methyl]-1-
methyl-3H-imidazol-1-ium chloride;
3-[(2-Hydroxy-6-acetylaminophenylcarbamoyl)methyl]-1-
methyl-3H-imidazol-1-ium chloride;
3-[(2-Hydroxy-4,6-diaminophenylcarbamoyl)methyl]-1-
methyl-3H-imidazol-1-ium chloride;
3-[(2-Hydroxy-4-acetylamino-6-aminophenylcarbamoyl)
methyl]-1-methyl-3H-imidazol-1-ium chloride;
3-[(2-Hydroxy-3,5-dichloro-4-methylphenylcarbamoyl)
methyl]-1-methyl-3H-imidazol-1-ium chloride;
3-[(2-Hydroxy-3,5-dichloro-4-aminophenylcarbamoyl)
methyl]-1-methyl-3H-imidazol-1-ium chloride;
3-[(2-Hydroxy-3,5-dichloro-4-
acetylaminophenylcarbamoyl)methyl]-1-methyl-3H-
imidazol-1-ium chloride;
3-[(2-Hydroxy-3,5-dichloro-4-
methoxycarbonylaminophenylcarbamoyl)methyl]-1-
methyl-3H-imidazol-1-ium chloride;
3-[(2-Hydroxy-3-acetylaminophenylcarbamoyl)methyl]-1-
methyl-3H-imidazol-1-ium chloride;
1-[(2-Hydroxyphenylcarbamoyl)methyl]pyridinium chloride;
1-[(2-Hydroxy-3-(2-(pyridinium-1-yl)acetylamino)
phenylcarbamoyl)methyl]pyridinium dichloride;
1-[(2-Hydroxy-4-(2-(pyridinium-1-yl)acetylamino)
phenylcarbamoyl)methyl]pyridinium dichloride;
1-[(2-Hydroxy-4-methylphenylcarbamoyl)methyl]
pyridinium chloride;
1-[(2-Hydroxy-4-aminophenylcarbamoyl)methyl]
pyridinium chloride;
1-[(2-Hydroxy-4-acetylaminophenylcarbamoyl)methyl]
pyridinium chloride;
1-[(2-Hydroxy-4-methoxycarbonylaminophenylcarbamoyl)
methyl]pyridinium chloride;
1-[(3-Hydroxy-4-acetylaminophenylcarbamoyl)methyl]
pyridinium chloride;
1-[(3-Hydroxy-4-methoxycarbonylaminophenylcarbamoyl)
methyl]pyridinium chloride;
1-[(2-Hydroxy-5-chlorophenylcarbamoyl)methyl]
pyridinium chloride;
1-[(2-Hydroxy-4-methyl-5-chlorophenylcarbamoyl)methyl]
pyridinium chloride;
1-[(2-Hydroxy-4-amino-5-chlorophenylcarbamoyl)methyl]
pyridinium chloride;
1-[(2-Hydroxy-4-acetylamino-5-chlorophenylcarbamoyl)
methyl]pyridinium chloride;
1-[(2-Hydroxy-4-methoxycarbonylamino-5-
chlorophenylcarbamoyl)methyl]pyridinium chloride;
1-[(3-Hydroxy-4-acetylamino-6-chlorophenylcarbamoyl)
methyl]pyridinium chloride;
1-[(3-Hydroxy-4-methoxycarbonylamino-6-
chlorophenylcarbamoyl)methyl]pyridinium chloride;
1-[(2-Hydroxy-5-methoxyphenylcarbamoyl)methyl]
pyridinium chloride;
1-[(2-Hydroxy-4-methyl-5-methoxyphenylcarbamoyl)
methyl]pyridinium chloride;
1-[(2-Hydroxy-4-amino-5-methoxyphenylcarbamoyl)
methyl]pyridinium chloride;
1-[(2-Hydroxy-4-acetylamino-5-methoxyphenylcarbamoyl)
methyl]pyridinium chloride;
1-[(2-Hydroxy-4-methoxycarbonylamino-5-
methoxylphenylcarbamoyl)methyl]pyridinium chloride;
1-[(3-Hydroxy-4-acetylamino-6-methoxyphenylcarbamoyl)
methyl]pyridinium chloride;
1-[(3-Hydroxy-4-methoxycarbonylamino-6-
methoxyphenylcarbamoyl)methyl]pyridinium chloride;
1-[(2-Hydroxy-6-aminophenylcarbamoyl)methyl]
pyridinium chloride;
1-[(2-Hydroxy-6-acetylaminophenylcarbamoyl)methyl]
pyridinium chloride;
1-[(2-Hydroxy-4,6-diaminophenylcarbamoyl)methyl]
pyridinium chloride;
1-[(2-Hydroxy-4-acetylamino-6-aminophenylcarbamoyl)
methyl]pyridinium chloride;
1-[(2-Hydroxy-3,5-dichloro-4-methylphenylcarbamoyl)
methyl]pyridinium chloride;
1-[(2-Hydroxy-3,5-dichloro-4-aminophenylcarbamoyl)
methyl]pyridinium chloride;
1-[(2-Hydroxy-3,5-dichloro-4-
acetylaminophenylcarbamoyl)methyl]pyridinium chloride;
1-[(2-Hydroxy-3,5-dichloro-4-
methoxycarbonylaminophenylcarbamoyl)methyl]
pyridinium chloride;
1-[(2-Hydroxy-3-acetylaminophenylcarbamoyl)methyl]
pyridinium chloride;
1-[(2-Hydroxyphenylcarbamoyl)methyl]-1,4-
dimethylpiperazin-1-ium chloride;
1-[(2-Hydroxy-3-(2-(1,4-dimethylpiperazin-1-ium-1-yl)
acetyl)aminophenylcarbamoyl)methyl]-1,4-
dimethylpiperazin-1-ium dichloride;
1-[(2-Hydroxy-4-(2-(1,4-dimethylpiperazin-1-ium-1-yl)
acetyl)aminophenylcarbamoyl)methyl]-1,4-
dimethylpiperazin-1-ium dichloride;
1-[(2-Hydroxy-4-methylphenylcarbamoyl)methyl]-1,4-
dimethylpiperazin-1-ium chloride;
1-[(2-Hydroxy-4-aminophenylcarbamoyl)methyl]-1,4-
dimethylpiperazin-1-ium chloride;

1-[(2-Hydroxy-4-acetylaminophenylcarbamoyl)methyl]-1,4-dimethylpiperazin-1-ium chloride;
1-[(2-Hydroxy-4-methoxycarbonylaminophenylcarbamoyl)methyl]-1,4-dimethylpiperazin-1-ium chloride;
1-[(3-Hydroxy-4-acetylaminophenylcarbamoyl)methyl]-1,4-dimethylpiperazin-1-ium chloride;
1-[(3-Hydroxy-4-methoxycarbonylaminophenylcarbamoyl)methyl]-1,4-dimethylpiperazin-1-ium chloride;
1-[(2-Hydroxy-5-chlorophenylcarbamoyl)methyl]-1,4-dimethylpiperazin-1-ium chloride;
1-[(2-Hydroxy-4-methyl-5-chlorophenylcarbamoyl)methyl]-1,4-dimethylpiperazin-1-ium chloride;
1-[(2-Hydroxy-4-amino-5-chlorophenylcarbamoyl)methyl]-1,4-dimethylpiperazin-1-ium chloride;
1-[(2-Hydroxy-4-acetylamino-5-chlorophenylcarbamoyl)methyl]-1,4-dimethylpiperazin-1-ium chloride;
1-[(2-Hydroxy-4-methoxycarbonylamino-5-chlorophenylcarbamoyl)methyl]-1,4-dimethylpiperazin-1-ium chloride;
1-[(3-Hydroxy-4-acetylamino-6-chlorophenylcarbamoyl)methyl]-1,4-dimethylpiperazin-1-ium chloride;
1-[(3-Hydroxy-4-methoxycarbonylamino-6-chlorophenylcarbamoyl)methyl]-1,4-dimethylpiperazin-1-ium chloride;
1-[(2-Hydroxy-5-methoxyphenylcarbamoyl)methyl]-1,4-dimethylpiperazin-1-ium chloride;
1-[(2-Hydroxy-4-methyl-5-methoxyphenylcarbamoyl)methyl]-1,4-dimethylpiperazin-1-ium chloride;
1-[(2-Hydroxy-4-amino-5-methoxyphenylcarbamoyl)methyl]-1,4-dimethylpiperazin-1-ium chloride;
1-[(2-Hydroxy-4-acetylamino-5-methoxyphenylcarbamoyl)methyl]-1,4-dimethylpiperazin-1-ium chloride;
1-[(2-Hydroxy-4-methoxycarbonylamino-5-methoxyphenylcarbamoyl)methyl]-1,4-dimethylpiperazin-1-ium chloride;
1-[(3-Hydroxy-4-acetylamino-6-methoxyphenylcarbamoyl)methyl]-1,4-dimethylpiperazin-1-ium chloride;
1-[(3-Hydroxy-4-methoxycarbonylamino-6-methoxyphenylcarbamoyl)methyl]-1,4-dimethylpiperazin-1-ium chloride;
1-[(2-Hydroxy-6-aminophenylcarbamoyl)methyl]-1,4-dimethylpiperazin-1-ium chloride;
1-[(2-Hydroxy-6-acetylaminophenylcarbamoyl)methyl]-1,4-dimethylpiperazin-1-ium chloride;
1-[(2-Hydroxy-4,6-diaminophenylcarbamoyl)methyl]-1,4-dimethylpiperazin-1-ium chloride;
1-[(2-Hydroxy-4-acetylamino-6-aminophenylcarbamoyl)methyl]-1,4-dimethylpiperazin-1-ium chloride;
1-[(2-Hydroxy-3,5-dichloro-4-methylphenylcarbamoyl)methyl]-1,4-dimethylpiperazin-1-ium chloride;
1-[(2-Hydroxy-3,5-dichloro-4-aminophenylcarbamoyl)methyl]-1,4-dimethylpiperazin-1-ium chloride;
1-[(2-Hydroxy-3,5-dichloro-4-acetylaminophenylcarbamoyl)methyl]-1,4-dimethylpiperazin-1-ium chloride;
1-[(2-Hydroxy-3,5-dichloro-4-methoxycarbonylaminophenylcarbamoyl)methyl]-1,4-dimethylpiperazin-1-ium chloride;
1-[(2-Hydroxy-3-acetylaminophenylcarbamoyl)methyl]-1,4-dimethylpiperazin-1-ium chloride; and their addition salts with an acid.

The addition salts with an acid of the compounds of formula (I') may be in particular chosen from hydrochlorides, hydrobromides, sulphates, citrates, succinates, tartrates, lactates and acetates.

These novel compounds of formula (I') may be prepared according to methods well known in the state of the art and described for example in patent applications or patents FR-A-1,596,879; BE 816,674; EP 0,579,204; DE 2,846,931; JP-54-115230; GB 2,070,000; DE 3,027,128; EP 0,065,874; EP 0,115,194; EP 0,079,141; EP 0,081,321; DE 3,246,238; EP 0,168,729; DE 3,414,051; JP-59-059656; FR-A-2,575,470; EP-0,193,051; JP-63-208562; JP-62-173469; JP-62-108859; JP-62-173469; DD253997; DE 3,641,825, JP-63-208562; DE 3,621,215; JP-01-249739; JP-64-002045; JP-02-255674; JP-01-032261; JP-02-255674; EP 0,608,896; WO 94/19316; JP-09-169705; EP 0,790,240; as well as in the documents Res. Discl. (1981), 202, 76–8; Synthesis (1982), 940–2, Res. Discl. (1983), 235, 352–3; Res. Discl. (1984), 247, 554–6; Res. Discl. (1985), 251, 134–9; Chem. Ind. (Dekker) (1992), 47 (Catal. Org. React.), 147–51; and J. Med. Chem. (199) 4062–79.

The subject of the invention is finally the use of the compounds of formula (I') as coupler for the oxidation dyeing of keratinous fibres and in particular human keratinous fibres such as hair.

The following examples are intended to illustrate the invention without limiting the scope thereof as a result.

EXAMPLES OF PREPARATION

Example of Preparation 1

Synthesis of 3-[(3,5-dichloro-2-hydroxy-4-methylphenylcarbamoyl)methyl]-1-methyl-3H-imidazol-1-ium chloride

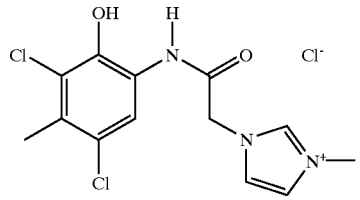

Step No. 1

24.3 ml of triethylamine (2 equivalents) are added dropwise to a suspension of 6-amino-2,4-dichloro-3-methylphenol hydrochloride (20 g, 87 mmol) in 1 liter of tetrahydrofuran, with stirring and under an inert atmosphere; after 2 hours, 30.7 ml of chloroacetyl chloride (1 equivalent) are added over 15 minutes. The suspension was filtered on sintered glass and the inorganic salts were abundantly rinsed with tetrahydrofuran. The mixture of the organic solvents was concentrated under vacuum. The residue was taken up in ethyl acetate, washed with water with 6 times 100 ml, dried over sodium sulphate and concentrated, to give 23 g of a brown powder. This powder was washed several times with ether and dried under vacuum to give 18.5 g of 2-chloro-N-(3,5-dichloro-2-hydroxy-4-methylphenyl)acetamide whose melting point was 149° C. (yield 78%).

Step No. 2

4.45 ml of N-methylimidazole (56 mmol) were added to a suspension of 5 g of 2-chloro-N-(3,5-dichloro-2-hydroxy-4-methylphenyl)acetamide (18.6 mmol), obtained above in the preceding step, in 5 ml of ethyl acetate, leading to a clear solution. After 3 hours and 30 minutes, the insoluble product which formed was drained and abundantly washed with ethyl acetate. The new precipitate which formed in the filtrates was drained and abundantly washed with ethyl acetate. The white powders thus obtained were combined and dried to give 5 g of 3-[(3,5-dichloro-2-hydroxy-4-methylphenylcarbamoyl)methyl]-1-methyl-3H-imidazol-1-ium chloride whose melting point was 251° C., (yield 77%).

The elemental analysis calculated for $C_{13}H_{14}Cl_3N_3O_2$ was the following:

|  | % | | | |
|---|---|---|---|---|
|  | C | H | N | O |
| Calculated | 44.05 | 3.97 | 11.82 | 9.15 |
| Found | 44.53 | 4.02 | 11.98 | 9.13 |

Example of Preparation 2

Synthesis of 3-[(4-acetylamino-2-hydroxyphenylcarbamoyl)methyl]-1-methyl-3H-imidazol-1-ium chloride

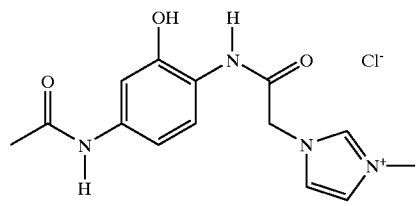

Step No. 1

27.5 ml of triethylamine (2 equivalents) were added dropwise to a suspension of 2-amino-5-(acetylamino)phenol hydrochloride (20 g, 98 mmol) in 1 liter of tetrahydrofuran, with stirring and under an inert atmosphere. After stirring for 1 hour, 8.26 ml of chloroacetyl chloride (1.05 equivalent) were added over 15 minutes. The suspension was filtered on sintered glass and the inorganic salts were abundantly rinsed with tetrahydrofuran. The mixture of organic solvents was concentrated under vacuum. The residue was taken up in ethyl acetate, the insoluble products were drained and washed with ethyl acetate to give 22 g of a brown powder. This powder was washed several times with ether and dried under vacuum to give 18.5 g of N-(4-acetylamino-2-hydroxyphenyl)-2-chloroacetamide whose melting point was 218° C., (yield 90%).

Step No. 2

9.85 ml of N-methylimidazole (123 mmol) were added to a suspension of 10 g (41 mmol) of N-(4-acetylamino-2-hydroxyphenyl)-2-chloroacetamide obtained above in the preceding step in 30 ml of ethyl acetate. The reaction medium was heated under reflux for 6 hours and then the insoluble product formed was drained and abundantly washed with ethyl acetate. The brown solid thus obtained was taken up in water and filtered and then the filtrate was poured over dioxane. The precipitate obtained was drained, abundantly washed with dioxane and then with isopropyl ether and dried under vacuum to give 10.6 g of 3-[(4-acetylamino-2-hydroxyphenylcarbamoyl)methyl]-1-methyl-3H-imidazol-1-ium chloride in the form of a purple-brown powder whose melting point was 225° C., (yield 79%).

EXAMPLES OF DYEING

Examples 1 to 6 of Dyeing in Alkaline Medium

The following dyeing compositions were prepared (contents in mol):

| EXAMPLE | 1 | 2 | 3 | 4 | 5 | 6 |
|---|---|---|---|---|---|---|
| 3-[(3,5-Dichloro-2-hydroxy-4-methylphenylcarbamoyl)methyl]-1-methyl-3H-imidazol-1-ium chloride (compound of formula (I)) | $3 \times 10^{3-}$ | — | — | $3 \times 10^{3-}$ | — | — |
| 1-[(3,5-Dichloro-2-hydroxy-4-methylphenylcarbamoyl)methyl]-1,4-dimethylpiperazin-1-ium chloride (compound of formula (I)) | — | $3 \times 10^{3-}$ | — | — | $3 \times 10^{3-}$ | — |
| 3-[(4-Acetylamino-2-hydroxyphenylcarbamoyl)methyl]-1-methyl-3H-imidazol-1-ium chloride (compound of formula (I)) | — | — | $3 \times 10^{3-}$ | — | — | $3 \times 10^{3-}$ |
| para-Phenylenediamine (oxidation base) | $3 \times 10^{3-}$ | — | — | $3 \times 10^{3-}$ | — | — |
| 4,5-diamino-1-methyl-3-methylpyrazole.2HCl (oxidation base) | — | $3 \times 10^{3-}$ | — | — | $3 \times 10^{3-}$ | — |
| Common dye carrier No. 1 | (*) | (*) | (*) | (*) | (*) | (*) |
| Demineralized water qs | 100 g | 100 g | 100 g | 100 g | 100 g | 100 g |

(*) Common dyeing carrier No. 1:

| Ethyl alcohol at 96% | 18 g |
|---|---|
| Sodium metabisulphite in aqueous solution at 35% | 0.68 g |
| Pentasodium salt of diethylenetriamino-pentaacetatic acid | 1.1 g |
| Aqueous ammonia at 20% | 10.0 g |

At the time of use, each of the above dyeing compositions was mixed weight for weight with a solution of hydrogen peroxide at 20 volumes (6% by weight) of pH 3.

The mixture obtained was applied to locks of permanently waved grey hair which is 90% white for 30 minutes. The locks were then rinsed, washed with a standard shampoo, rinsed again and then dried.

The shades obtained are presented in the table below:

| EXAMPLE | Dyeing pH | Shade obtained |
|---------|-----------|----------------|
| 1 | 10 ± 0.2 | slightly matt ashen chestnut brown |
| 2 | 10 ± 0.2 | ashen matt light chestnut brown |
| 3 | 10 ± 0.2 | slightly bluish ashen purple |
| 4 | 10 ± 0.2 | dark blue |
| 5 | 10 ± 0.2 | ashen blue |
| 6 | 10 ± 0.2 | violet ashen light chestnut brown |

Examples 7 to 12 of Dyeing in Alkaline Medium

The following dyeing compositions were prepared (contents in mol):

| EXAMPLE | 7 | 8 | 9 | 10 | 11 | 12 |
|---------|---|---|---|----|----|----|
| 3-[(3,5-Dichloro-2-hydroxy-4-methylphenylcarbamoyl)-methyl]-1-methyl-3H-imidazol-1-ium chloride (compound of formula (I)) | $3 \times 10^{3-}$ | — | — | $3 \times 10^{3-}$ | — | — |
| 1-[(3,5-Dichloro-2-hydroxy-4-methylphenylcarbamoyl)-methyl]-1,4-dimethylpiperazin-1-ium chloride (compound of formula (I)) | — | $3 \times 10^{3-}$ | — | — | $3 \times 10^{3-}$ | — |
| 3-[(4-Acetylamino-2-hydroxyphenylcarbamoyl)methyl]-1-methyl-3H-imidazol-1-ium chloride (compound of formula (I)) | — | — | $3 \times 10^{3-}$ | — | — | $3 \times 10^{3-}$ |
| Pyrazolo[1,5-a]pyrimidine-3,7-diamine.2HCl (oxidation base) | $3 \times 10^{3-}$ | — | — | $3 \times 10^{3-}$ | — | — |
| N,N-bis-β-Hydroxyethyl-para-phenylenediamine (oxidation base) | — | $3 \times 10^{3-}$ | — | — | $3 \times 10^{3-}$ | — |
| Common dye carrier No. 1 | (*) | (*) | (*) | (*) | (*) | (*) |
| Demineralized water qs | 100 g | 100 g | 100 g | 100 g | 100 g | 100 g |

(*) Common dye carrier No. 1:

It was identical to that used above for Examples 1 to 6.

At the time of use, each of the above dyeing compositions was mixed weight for weight with a solution of hydrogen peroxide at 20 volumes (6% by weight) of pH 3.

The mixture obtained was applied to locks of permanently waved grey hair which is 90% white for 30 minutes. The locks were then rinsed, washed with a standard shampoo, rinsed again and then dried.

The shades obtained are presented in the table below:

| EXAMPLE | Dyeing pH | Shade obtained |
|---------|-----------|----------------|
| 7 | 10 ± 0.2 | slightly ashen iridescent violet |
| 8 | 10 ± 0.2 | slightly ashen violet iridescent blonde |
| 9 | 10 ± 0.2 | red iridescent dark blonde |
| 10 | 10 ± 0.2 | matt blonde |
| 11 | 10 ± 0.2 | matt light blonde |
| 12 | 10 ± 0.2 | blue |

What is claimed is:

1. A composition for oxidation dyeing keratinous fibers comprising, in a medium suitable for dyeing:
(a) at least one oxidation base; and
(b) at least one coupler chosen from compounds of formula (I) and acid addition salts of any of the foregoing compounds:

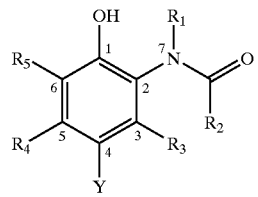

wherein:
at least one of $R_1$, $R_2$, $R_3$, $R_4$, and $R_5$, as defined below, is chosen from a group Z, as defined below;
$R_1$ is chosen from:
(1) a hydrogen atom;
(2) linear and branched, saturated and unsaturated groups containing from 1–15 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
(i) said $R_1$ does not comprise a group chosen from a peroxide group, a diazo group, a nitro group, and a nitroso group, and
(ii) said $SO_2$ group is not directly linked to the nitrogen atom at the 7-position of formula (I);
(3) a group Z chosen from cationic groups of formula (II):

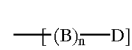

wherein:
groups B are chosen from linear and branched, saturated and unsaturated groups containing from 1–15 carbon atoms, optionally substituted with at least one substituent chosen from a halogen atom and a group Z, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the proviso that:

(i) said B does not comprise a group chosen from a peroxide group, a diazo group, a nitro group, and a nitroso group; and groups D are chosen from cationic groups of formulae (III) and (IV):

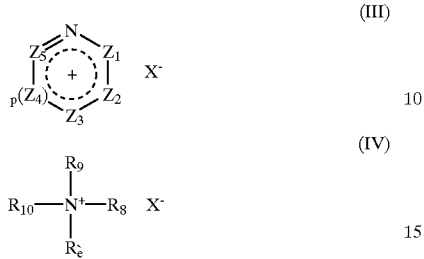

(III)

(IV)

wherein:
group $Z_1$, group $Z_2$, group $Z_3$, and group $Z_4$, which are identical or different, are each chosen from
1) an oxygen atom and a sulfur atom,
2) a nitrogen atom, optionally substituted with an $R_{11}$, group, as defined below, and
3) a carbon atom, optionally substituted with one or two $R_{11}$ groups, as defined below, which are identical or different;

group $Z_5$ is chosen from
1) a nitrogen atom and
2) a carbon atom, optionally substituted with an $R_{11}$ group, as defined below;

two of the adjacent groups $Z_1$, $Z_2$, $Z_3$, $Z_4$ and $Z_5$ may optionally form a 5- to 7-membered ring, wherein each member is chosen from
1) an oxygen atom and a sulfur atom,
2) a nitrogen atom, optionally substituted with an $R_{11}$ group, as defined below, and
3) a carbon atom, optionally substituted with one or two $R_{11}$ groups, as defined below, which are identical or different;

wherein:
said groups $R_{11}$ are chosen from:
a hydrogen atom;
a group Z as defined above;
linear and branched, saturated and unsaturated groups containing from 1 to 10 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the proviso that:
(i) said $R_{11}$ does not comprise a group chosen from a peroxide group, a diazo group, a nitro group, and a nitroso group, $Z_6$ is chosen from said $R_{11}$ groups, provided that $Z_6$ is not a hydrogen atom;

$Z_1$ and $Z_6$, or $Z_5$ and $Z_6$, optionally form a 5- to 7-membered ring chosen from saturated rings and unsaturated rings, wherein said members are each optionally substituted with one or two said radicals $R_{11}$, which are identical or different;

$R_\dot{e}$, $R_8$, $R_9$, and $R_{10}$, which are identical or different, are each chosen from said groups $R_{11}$;

groups $R_\dot{e}$, $R_8$, and $R_9$ optionally form, in pairs with the quaternary nitrogen atom to which they are attached, at least one 5- to 7-membered saturated ring, wherein said members are each chosen from
1) an oxygen atom and a sulfur atom,
2) a nitrogen atom, optionally substituted with a said $R_{11}$ group, and
3) a carbon atom, optionally substituted with one or two said $R_{11}$ groups, which are identical or different;

$X^-$ is chosen from organic anions and inorganic anions;

said groups B are linked to said groups D by any one of the atoms of said group D;

n and p, independently of each other, are equal to 0 or 1;

when n=0, then said group $R_{10}$ is optionally a direct bond, wherein said cationic group of formula (IV) is linked directly to said compound of formula (I) by way of the nitrogen cation of said cationic group of formula (IV);

$R_2$ is chosen from:
(1) a hydrogen atom;
(2) a group Z as defined above;
(3) linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
(i) said $R_2$ does not comprise a group chosen from a peroxide group, a diazo group, a nitro group, and a nitroso group; and
(ii) $R_2$ is not a hydroxyl or a thio group;

said $R_1$ and said $R_2$, together with the atoms to which they are attached, optionally form a 5- to 7-membered ring chosen from saturated rings and unsaturated rings, wherein said members are each chosen from a carbon atom, a nitrogen atom, an oxygen atom, a sulfur atom, and a carbonyl group, and said members are optionally substituted with 1 or 2 groups R, wherein
R is chosen from linear and branched, saturated and unsaturated, $C_1$–$C_6$ alkyl groups, optionally substituted with at least one halogen atom, wherein at least one carbon atom is optionally and independently replaced by an oxygen atom, a nitrogen atom, a sulfur atom, or an $SO_2$ group, and at least one branch of said branched $C_1$–$C_6$ alkyl group optionally forms at least one ring chosen from saturated and unsaturated 3- to 6-membered rings; with the proviso that:
(i) said R does not comprise a group chosen from a peroxide group, a diazo group, a nitro group, and a nitroso group;

$R_3$ and $R_4$, which are identical or different, are each chosen from:
a hydrogen atom and halogen atoms;
a group Z as defined above;
linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally form at least one 3- to 7-membered ring comprising at least one carbon atom, with the provisos that:
(i) said $R_3$ and said $R_4$ do not comprise a group chosen from a peroxide group, a diazo group, a nitro group, and a nitroso group;
(ii) said $R_3$ and said $R_4$ are not a hydroxyl group; and
(iii) said $R_3$ and said $R_4$ are not directly linked to the benzene ring of formula (I) by an —NH—NH— group;

$R_5$ is chosen from:
a hydrogen atom and halogen atoms;
a group Z as defined above;
linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
(i) said $R_5$ does not comprise a group chosen from a peroxide group, a diazo group, a nitro group, and a nitroso group;
(ii) said $R_5$ is chosen from a group other than a hydroxyl group, a thio group, an amino group, and an optionally substituted sulphonylamino group; and
(iii) said $R_5$ is not directly linked to the benzene ring of formula (I) by a —NH—NH— group;

said $R_1$ and said $R_3$, together with the atoms to which they are attached, optionally form a 6- to 7-membered saturated ring, wherein said members are each chosen from a carbon atom, a nitrogen atom, an oxygen atom, a sulfur atom, and a carbonyl group, and said members are optionally substituted with 1 or 2 said groups R as defined above, with the proviso that:
(i) said R does not comprise a group chosen from a peroxide group, a diazo group, a nitro group, and a nitroso group; and said $R_2$ and said $R_3$, together with the atoms to which they are attached, optionally form a 5- to 7-membered saturated ring, wherein said members are each chosen from a carbon atom, a nitrogen atom, an oxygen atom, a sulfur atom, and a carbonyl group, and said members are optionally substituted with 1 or 2 said groups R as defined above, with the proviso that:
(i) said R does not comprise a group chosen from a peroxide group, a diazo group, a nitro group, and a nitroso group;
(ii) when said $R_2$ and said $R_3$ form a 5- to 7-membered saturated ring, said $R_3$ optionally is a bond;

Y is chosen from:
a hydrogen atom and halogen atoms;
groups —$OR_6$, —$SR_6$ and —NH—$SO_2R_6$, wherein
$R_6$ is chosen from linear and branched $C_1$–$C_6$ alkyl groups, optionally substituted with at least one group chosen from a halogen atom, a hydroxyl group, $C_1$–$C_4$ alkoxy groups, an amino group, amino($C_1$–$C_4$ alkyl) groups, wherein at least one branch of said $R_6$ optionally forms at least one 3- to 6-membered ring;
a phenyl group, optionally substituted with one or two groups chosen from $C_1$–$C_4$ alkyl groups, a trifluoromethyl group, a carboxyl group, $C_1$–$C_4$ alkoxycarbonyl groups, a halogen atom, a hydroxyl group, $C_1$–$C_4$ alkoxy groups, an amino group and amino ($C_1$–$C_4$ alkyl) groups; and
a benzyl group, optionally substituted with one or two oxy groups.

2. A composition for oxidation dyeing keratinous fibers comprising, in a medium suitable for dyeing:
(a) at least one oxidation base; and
(b) at least one coupler chosen from compounds of formula (I) and acid addition salts of any of the foregoing compounds:

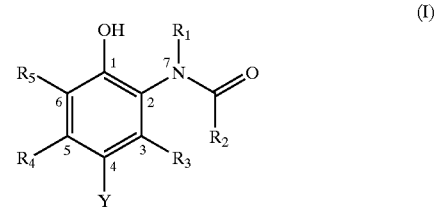

(I)

wherein:
at least one of $R_1$, $R_2$, $R_3$, $R_4$, and $R_5$, as defined below, is chosen from a group Z, as defined below;
$R_1$ is chosen from:
(1) a hydrogen atom;
(2) a group Z chosen from cationic groups of formula (II);

(II)

wherein:
groups B are chosen from linear and branched, saturated and unsaturated groups containing from 1–15 carbon atoms, optionally substituted with at least one substituent chosen from a halogen atom and a group Z, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the proviso that:
(i) said B does not comprise a group chosen from a peroxide group, a diazo group, a nitro group, and a nitroso group; and
groups D are chosen from cationic groups of formulae (III) and (IV):

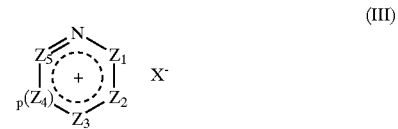

(III)

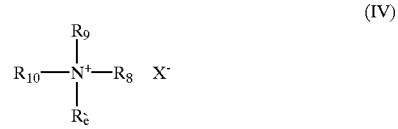

(IV)

wherein:
group $Z_1$, group $Z_2$, group $Z_3$, and group $Z_4$, which are identical or different, are each chosen from
1) an oxygen atom and a sulfur atom,
2) a nitrogen atom, optionally substituted with an $R_{11}$ group, as defined below, and 3) a carbon atom, optionally substituted with one or two $R_{11}$ groups, as defined below, which are identical or different;

group $Z_5$ is chosen from
1) a nitrogen atom and
2) a carbon atom, optionally substituted with an $R_{11}$ group, as defined below;

two of the adjacent groups $Z_1$, $Z_2$, $Z_3$, $Z_4$ and $Z_5$ may optionally from a 5- to 7-membered ring, wherein each member is chosen from
1) an oxygen atom and a sulfur atom,
2) a nitrogen atom, optionally substituted with an $R_{11}$ group, as defined below, and
3) a carbon atom, optionally substituted with one or two $R_{11}$ groups, as defined below, which are identical or different;

wherein:
said groups $R_{11}$ are chosen from:
a hydrogen atom;
a group Z as defined above;
linear and branched, saturated and unsaturated groups containing from 1 to 10 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the proviso that:
(i) said $R_{11}$ does not comprise a group chosen from a peroxide group, a diazo group, a nitro group, and a nitroso group, $Z_6$ is chosen from said $R_{11}$ groups, provided that $Z_6$ is not a hydrogen atom;

$Z_1$ and $Z_6$, or $Z_5$ and $Z_6$, optionally form a 5- to 7-membered ring chosen from a saturated ring and an unsaturated ring, wherein said members are each optionally substituted with one or two said radicals $R_{11}$, which are identical or different;

$R_7$, $R_8$, $R_9$, and $R_{10}$, which are identical or different, are each chosen from said groups $R_{11}$;

groups $R_7$, $R_8$, and $R_9$ optionally form, in pairs with the quaternary nitrogen atom to which they are attached, at least one 5- to 7-membered saturated ring, wherein said members are each chosen from
1) an oxygen atom and a sulfur atom,
2) a nitrogen atom, optionally substituted with a said $R_{11}$ group, and
3) a carbon atom, optionally substituted with one or two said $R_{11}$ groups, which are identical or different;

$X^-$ is chosen from organic anions and inorganic anions;

said groups B are linked to said groups D by any one of the atoms of said group D;

n and p, independently of each other, are equal to 0 or 1;

when n=0, then said group $R_{10}$ is optionally a direct bond, wherein said cationic group of formula (IV) is linked directly to said compound of formula (I) by way of the nitrogen cation of said cationic group of formula (IV);

(3) a Group $A_1$, wherein said Group $A_1$ is chosen from linear and branched $C_1$–$C_8$ alkyl groups optionally unsaturated and optionally substituted with at least one substituent chosen from:
a group $A_2$, $A_4$, or $A_5$ as defined below;
one or two groups, which are identical or different, chosen from N—$(C_1$–$C_3)$alkylamino, N—$(C_1$–$C_3)$alkyl-N—$(C_1$–$C_3)$alkylamino, $(C_1$–$C_6)$alkoxy, oxo, alkoxycarbonyl, acyloxy, amide, acylamino, ureyl, sulphoxy, sulphonyl, sulphonamido, sulphonylamino, bromo, cyano, and carboxyl; and
at least one group chosen from a hydroxyl group, a fluoro group, and a chloro group;

(4) a Group $A_2$ aromatic group chosen from a phenyl group, and a naphthyl group, wherein said aromatic group is optionally substituted with one to three groups, which are identical or different, chosen from methyl, trifluoromethyl, ethyl, isopropyl, butyl, pentyl, fluoro, chloro, bromo, methoxy, trifluoromethoxy, ethoxy, propyloxy, acetyloxy, acetyl, and cyano;

(5) a Group $A_3$ heteroaromatic group chosen from furanyl, thiophenyl, pyrrolyl, imidazolyl, thiazolyl, oxazolyl, 1,2,3-triazolyl, 1,2,4-triazolyl, isoxazolyl, isothiazolyl, pyrazolyl, pyrazolotriazolyl, pyrazoloimidazolyl, pyrrolotriazolyl, pyrazolopyrimidyl, pyrazolopyridyl, pyridyl, pyrimidyl, benzoimidazolyl, benzoxazolyl, benzothiazolyl, indolyl, indolidinyl, isoindolyl, indazolyl, benzotriazolyl, quinolinyl, benzoimidazolyl and benzopyrimidyl, wherein said heteroaromatic group is optionally substituted with 1 to 3 groups chosen from linear and branched $C_1$–$C_4$ alkyl groups, a $C_1$–$C_4$ monohydroxyalkyl group, a $C_2$–$C_4$ polyhydroxyalkyl group, a carboxyl group, an alkoxycarbonyl group, an amido group, an amino group, a hydroxyl group, and a halogen atom;

(6) a Group $A_4$, chosen from $C_3$–$C_7$ cycloalkyl groups and a norbornyl group, wherein said $C_3$–$C_7$ cycloalkyl groups and said norbornyl group optionally comprise at least one double bond, and wherein said $C_3$–$C_7$ cycloalkyl groups and said norbornyl group are optionally substituted with 1 or 2 substituents chosen from linear and branched $C_1$–$C_4$ alkyl groups, $C_1$–$C_4$ monohydroxyalkyl groups, $C_2$–$C_4$ polyhydroxyalkyl groups, a carboxyl group, alkoxycarbonyl groups, an amido group, an amino group, a hydroxyl group, and halogen atoms;

(7) a Group $A_5$ heterocycle chosen from dihydrofuranyl; tetrahydrofuranyl; butyrolactonyl; dihydrothiophenyl; tetrahydrothiophenyl; tetrahydrothiophenonyl; iminothiolane; dihydropyrrolyl; pyrrolidinyl; pyrrolidinonyl; imidazolidinonyl; imidazolidinethionyl; oxazolidinyl; oxazolidinonyl; oxazolanethione; thiazolidinyl; isothiazolonyl; mercaptothiazolinyl; pyrazolidinonyl; iminothiolane; dioxolanyl; pentalactone; dioxanyl; dihydropyridinyl; piperidinyl; pentalactam; morpholinyl; pyrazoli(di)nyl; pyrimi(di)nyl; pyrazinyl; piperazinyl; and azepinyl;

provided that when said $R_1$ is chosen from said Groups $A_1$, $A_2$, $A_3$, $A_4$, and $A_5$, said $R_1$ is optionally attached to the nitrogen atom at the 7-position of formula (I) by way of a group —(CO)—;

$R_2$ is chosen from:
(1) a hydrogen atom;
(2) a group Z as defined above;
(3) linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
(i) said $R_2$ does not comprise a group chosen from a peroxide group, a diazo group, a nitro group, and a nitroso group; and
(ii) $R_2$ is not a hydroxyl or a thio group;
said $R_1$ and said $R_2$, together with the atoms to which they are attached, optionally form a 5- to 7-membered ring chosen from saturated rings and unsaturated rings, wherein said members are each chosen from a carbon atom, a nitrogen atom, an oxygen atom, a sulfur atom, and a carbonyl group, and said members are optionally substituted with 1 or 2 groups R, wherein
R is chosen from linear and branched, saturated and unsaturated, $C_1$–$C_6$ alkyl groups, optionally substituted with at least one halogen atom, wherein at least one carbon atom is optionally and independently replaced by an oxygen atom, a nitrogen atom, a sulfur atom, or an $SO_2$ group, and at least one branch of said branched $C_1$–$C_6$ alkyl group optionally forms at least one ring chosen from saturated and unsaturated 3- to 6-membered rings; with the proviso that:
(i) said R does not comprise a group chosen from a peroxide group, a diazo group, a nitro group, and a nitroso group;
$R_3$ and $R_4$, which are identical or different, are each chosen from:
a hydrogen atom and halogen atoms;
a group Z as defined above;
linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally form at least one 3- to 7-membered ring comprising at least one carbon atom, with the provisos that:
(i) said $R_3$ and said $R_4$ do not comprise a group chosen from a peroxide group, a diazo group, a nitro group, and a nitroso group;
(ii) said $R_3$ and said $R_4$ are not a hydroxyl group; and
(iii) said $R_3$ and said $R_4$ are not directly linked to the benzene ring of formula (I) by an —NH—NH— group;
$R_5$ is chosen from:
a hydrogen atom and halogen atoms;
a group Z as defined above;
linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
(i) said $R_5$ does not comprise a group chosen from a peroxide group, a diazo group, a nitro group, and a nitroso group;
(ii) said $R_5$ is chosen from a group other than a hydroxyl group, a thio group, an amino group, and an optionally substituted sulphonylamino group; and
(iii) said $R_5$ is not directly linked to the benzene ring of formula (I) by a —NH—NH— group;
said $R_1$ and said $R_3$, together with the atoms to which they are attached, optionally form a 6- to 7-membered saturated ring, wherein said members are each chosen from a carbon atom, a nitrogen atom, an oxygen atom, a sulfur atom, and a carbonyl group, and said members are optionally substituted with 1 or 2 said groups R as defined above, with the proviso that:
(i) said R does not comprise a group chosen from a peroxide group, a diazo group, a nitro group, and a nitroso group; and
said $R_2$ and said $R_3$, together with the atoms to which they are attached, optionally form a 5- to 7-membered saturated ring, wherein said members are each chosen from a carbon atom, a nitrogen atom, an oxygen atom, a sulfur atom, and a carbonyl group, and said members are optionally substituted with 1 or 2 said groups R as defined above, with the proviso that:
(i) said R does not comprise a group chosen from a peroxide group, a diazo group, a nitro group, and a nitroso group;
(ii) when said $R_2$ and said $R_3$ form a 5- to 7-membered saturated ring, said $R_3$ optionally is a bond;
Y is chosen from:
a hydrogen atom and halogen atoms;
groups —$OR_6$, —$SR_6$ and —NH—$SO_2R_6$, wherein
$R_6$ is chosen from linear and branched $C_1$–$C_6$ alkyl groups, optionally substituted with at least one group chosen from a halogen atom, a hydroxyl group, $C_1$–$C_4$ alkoxy groups, an amino group, amino($C_1$–$C_4$ alkyl) groups, wherein at least one branch of said $R_6$ optionally forms at least one 3- to 6-membered ring;
a phenyl group, optionally substituted with one or two groups chosen from $C_1$–$C_4$ alkyl groups, a trifluoromethyl group, a carboxyl group, $C_1$–$C_4$ alkoxycarbonyl groups, a halogen atom, a hydroxyl group, $C_1$–$C_4$ alkoxy groups, an amino group and amino ($C_1$–$C_4$ alkyl) groups; and
a benzyl group, optionally substituted with one or two oxy groups.

3. A composition for oxidation dyeing keratinous fibers comprising, in a medium suitable for dyeing:
(a) at least one oxidation base; and
(b) at least one coupler chosen from compounds of formula (I) and acid addition salts of any of the foregoing compounds:

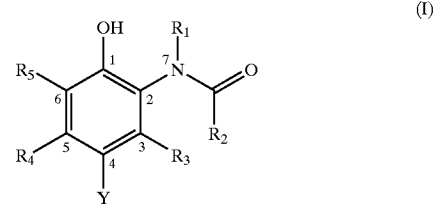

(I)

wherein:
at least one of $R_1$, $R_2$, $R_3$, $R_4$, and $R_5$, as defined below, is chosen from a group Z, as defined below;
$R_1$ is chosen from:
(1) a hydrogen atom;
(2) linear and branched, saturated and unsaturated groups containing from 1–15 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
(i) said $R_1$ does not comprise a group chosen from a peroxide group, a diazo group, a nitro group, and a nitroso group, and
(ii) said $SO_2$ group is not directly linked to the nitrogen atom at the 7-position of formula (I);
(3) a group Z chosen from cationic groups of formula (II);

(II)

wherein:
groups B are chosen from linear and branched, saturated and unsaturated groups containing from 1–15 carbon atoms, optionally substituted with at least one substituent chosen from a halogen atom and a group Z, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the proviso that:
(i) said B does not comprise a group chosen from a peroxide group, a diazo group, a nitro group, and a nitroso group; and
groups D are chosen from cationic groups of formulae (III) and (IV):

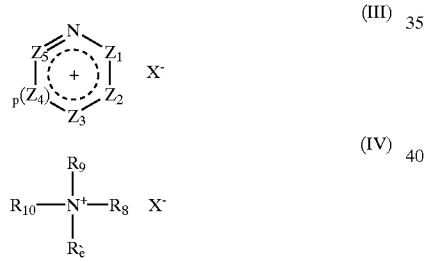

(III)

(IV)

wherein:
group $Z_1$, group $Z_2$, group $Z_3$, and group $Z_4$, which are identical or different, are each chosen from
1) an oxygen atom and a sulfur atom,
2) a nitrogen atom, optionally substituted with an $R_{11}$ group, as defined below, and
3) a carbon atom, optionally substituted with one or two $R_{11}$ groups, as defined below, which are identical or different;
group $Z_5$ is chosen from
1) a nitrogen atom and
2) a carbon atom, optionally substituted with an $R_{11}$ group, as defined below;
two of the adjacent groups $Z_1$, $Z_2$, $Z_3$, $Z_4$ and $Z_5$ may optionally form a 5- to 7-membered ring, wherein each member is chosen from
1) an oxygen atom and a sulfur atom,
2) a nitrogen atom, optionally substituted with an $R_{11}$ group, as defined below, and
3) a carbon atom, optionally substituted with one or two $R_{11}$ groups, as defined below, which are identical or different;

wherein:
said groups $R_{11}$ are chosen from:
a hydrogen atom;
a group Z as defined above;
linear and branched, saturated and unsaturated groups containing from 1 to 10 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the proviso that:
(i) said $R_{11}$ does not comprise a group chosen from a peroxide group, a diazo group, a nitro group, and a nitroso group,
$Z_6$ is chosen from said $R_{11}$ groups, provided that $Z_6$ is not a hydrogen atom;
$Z_1$ and $Z_6$, or $Z_5$ and $Z_6$, optionally form a 5- to 7-membered ring chosen from saturated rings and unsaturated rings, wherein said members are each optionally substituted with one or two said radicals $R_{11}$, which are identical or different;
$R_{\dot{s}}$, $R_8$, $R_9$, and $R_{10}$, which are identical or different, are each chosen from said groups $R_{11}$;
groups $R_{\dot{s}}$, $R_8$, and $R_9$ optionally form, in pairs with the quaternary nitrogen atom to which they are attached, at least one 5- to 7-membered saturated ring, wherein said members are each chosen from
1) an oxygen atom and a sulfur atom,
2) a nitrogen atom, optionally substituted with a said $R_{11}$ group, and
3) a carbon atom, optionally substituted with one or two said $R_{11}$ groups, which are identical or different;
$X^-$ is chosen from organic anions and inorganic anions;
said groups B are linked to said groups D by any one of the atoms of said group D;
n and p, independently of each other, are equal to 0 or 1;
when n=0, then said group $R_{10}$ is optionally a direct bond, wherein said cationic group of formula (IV) is linked directly to said compound of formula (I) by way of the nitrogen cation of said cationic group of formula (IV);
$R_2$ is chosen from:
(1) a hydrogen atom;
(2) an amino group;
(3) a group Z as defined above;
(4) a Group $A_1$, wherein said Group $A_1$ is chosen from linear and branched $C_1$–$C_8$ alkyl groups optionally unsaturated and optionally substituted with at least one substituent chosen from:
a group $A_2$, $A_4$, or $A_5$ as defined below;
one or two groups, which are identical or different, chosen from N—($C_1$–$C_3$)alkylamino, N—($C_1$–$C_3$)alkyl-N—($C_1$–$C_3$)alkylamino, ($C_1$–$C_6$)alkoxy, oxo, alkoxycarbonyl, acyloxy, amide, acylamino, ureyl, sulphoxy, sulphonyl, sulphonamido, sulphonylamino, bromo, cyano, and carboxyl; and
at least one group chosen from a hydroxyl group, a fluoro group, and a chloro group;

(5) a Group $A_2$ aromatic group chosen from a phenyl group, and a naphthyl group, wherein said aromatic group is optionally substituted with one to three groups, which are identical or different, chosen from methyl, trifluoromethyl, ethyl, isopropyl, butyl, pentyl, fluoro, chloro, bromo, methoxy, trifluoromethoxy, ethoxy, propyloxy, acetyloxy, acetyl, and cyano;

(6) a Group $A_3$ heteroaromatic group chosen from furanyl, thiophenyl, pyrrolyl, imidazolyl, thiazolyl, oxazolyl, 1,2,3-triazolyl, 1,2,4-triazolyl, isoxazolyl, isothiazolyl, pyrazolyl, pyrazolotriazolyl, pyrazoloimidazolyl, pyrrolotriazolyl, pyrazolopyrimidyl, pyrazolopyridyl, pyridyl, pyrimidyl, benzoimidazolyl, benzoxazolyl, benzothiazolyl, indolyl, indolidinyl, isoindolyl, indazolyl, benzotriazolyl, quinolinyl, benzoimidazolyl and benzopyrimidyl, wherein said heteroaromatic group is optionally substituted with 1 to 3 groups chosen from linear and branched $C_1$–$C_4$ alkyl groups, a $C_1$–$C_4$ monohydroxyalkyl group, a $C_2$–$C_4$ polyhydroxyalkyl group, a carboxyl group, an alkoxycarbonyl group, an amido group, an amino group, a hydroxyl group, and a halogen atom;

(7) a Group $A_4$, chosen from $C_3$–$C_7$ cycloalkyl groups and a norbornyl group, wherein said $C_3$–$C_7$ cycloalkyl groups and said norbornyl group optionally comprise at least one double bond, and wherein said $C_3$–$C_7$ cycloalkyl groups and said norbornyl group are optionally substituted with 1 or 2 substituents chosen from linear and branched $C_1$–$C_4$ alkyl groups, $C_1$–$C_4$ monohydroxyalkyl groups, $C_2$–$C_4$ polyhydroxyalkyl groups, a carboxyl group, alkoxycarbonyl groups, an amido group, an amino group, a hydroxyl group, and halogen atoms;

(8) a Group $A_5$ heterocycle chosen from dihydrofuranyl; tetrahydrofuranyl; butyrolactonyl; dihydrothiophenyl; tetrahydrothiophenyl; tetrahydrothiophenonyl; iminothiolane; dihydropyrrolyl; pyrrolidinyl; pyrrolidinonyl; imidazolidinonyl; imidazolidinethionyl; oxazolidinyl; oxazolidinonyl; oxazolanethione; thiazolidinyl; isothiazolonyl; mercaptothiazolinyl; pyrazolidinonyl; iminothiolane; dioxolanyl; pentalactone; dioxanyl; dihydropyridinyl; piperidinyl; pentalactam; morpholinyl; pyrazoli(di)nyl; pyrimi(di)nyl; pyrazinyl; piperazinyl; and azepinyl;

provided that said groups $A_1$, $A_2$, $A_3$, $A_4$, and $A_5$ are optionally attached to the carbon at the 8-position of the compounds of formula (I) by way of an —O— atom, an —NH— group, an —N($C_1$–$C_3$)alkyl-group, a —(CO)— group, a —(CO)O— group, or a —(CO)NH— group;

said $R_1$ and said $R_2$, together with the atoms to which they are attached, optionally form a 5- to 7-membered ring chosen from saturated rings and unsaturated rings, wherein said members are each chosen from a carbon atom, a nitrogen atom, an oxygen atom, a sulfur atom, and a carbonyl group, and said members are optionally substituted with 1 or 2 groups R, wherein
R is chosen from linear and branched, saturated and unsaturated, $C_1$–$C_6$ alkyl groups, optionally substituted with at least one halogen atom, wherein at least one carbon atom is optionally and independently replaced by an oxygen atom, a nitrogen atom, a sulfur atom, or an $SO_2$ group, and at least one branch of said branched $C_1$–$C_6$ alkyl group optionally forms at least one ring chosen from saturated and unsaturated 3- to 6-membered rings; with the proviso that:
(i) said R does not comprise a group chosen from a peroxide group, a diazo group, a nitro group, and a nitroso group;

$R_3$ and $R_4$, which are identical or different, are each chosen from:
a hydrogen atom and halogen atoms;
a group Z as defined above;
linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally form at least one 3- to 7-membered ring comprising at least one carbon atom, with the provisos that:
(i) said $R_3$ and said $R_4$ do not comprise a group chosen from a peroxide group, a diazo group, a nitro group, and a nitroso group;
(ii) said $R_3$ and said $R_4$ are not a hydroxyl group; and
(iii) said $R_3$ and said $R_4$ are not directly linked to the benzene ring of formula (I) by an —NH—NH— group;

$R_5$ is chosen from:
a hydrogen atom and halogen atoms;
a group Z as defined above;
linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
(i) said $R_5$ does not comprise a group chosen from a peroxide group, a diazo group, a nitro group, and a nitroso group;
(ii) said $R_5$ is chosen from a group other than a hydroxyl group, a thio group, an amino group, and an optionally substituted sulphonylamino group; and
(iii) said $R_5$ is not directly linked to the benzene ring of formula (I) by a —NH—NH— group;

said $R_1$ and said $R_3$, together with the atoms to which they are attached, optionally form a 6- to 7-membered saturated ring, wherein said members are each chosen from a carbon atom, a nitrogen atom, an oxygen atom, a sulfur atom, and a carbonyl group, and said members are optionally substituted with 1 or 2 said groups R as defined above, with the proviso that:
(i) said R does not comprise a group chosen from a peroxide group, a diazo group, a nitro group, and a nitroso group; and said $R_2$ and said $R_3$, together with the atoms to which they are attached, optionally form a 5- to 7-membered saturated ring, wherein said members are each chosen from a carbon atom, a nitrogen atom, an oxygen atom, a sulfur atom, and a carbonyl group, and said members are optionally substituted with 1 or 2 said groups R as defined above, with the proviso that:
(i) said R does not comprise a group chosen from a peroxide group, a diazo group, a nitro group, and a nitroso group;
(ii) when said $R_2$ and said $R_3$ form a 5- to 7-membered saturated ring, said $R_3$ optionally is a bond;

Y is chosen from:
  a hydrogen atom and halogen atoms;
  groups —$OR_6$, —$SR_6$ and —NH—$SO_2R_6$, wherein—
    $R_6$ is chosen from linear and branched $C_1$–$C_6$ alkyl groups, optionally substituted with at least one group chosen from a halogen atom, a hydroxyl group, $C_1$–$C_4$ alkoxy groups, an amino group, amino($C_1$–$C_4$ alkyl) groups, wherein at least one branch of said $R_6$ optionally forms at least one 3- to 6-membered ring;
  a phenyl group, optionally substituted with one or two groups chosen from $C_1$–$C_4$ alkyl groups, a trifluoromethyl group, a carboxyl group, $C_1$–$C_4$ alkoxycarbonyl groups, a halogen atom, a hydroxyl group, $C_1$–$C_4$ alkoxy groups, an amino group and amino ($C_1$–$C_4$ alkyl) groups; and
  a benzyl group, optionally substituted with one or two oxy groups.

4. A composition for oxidation dyeing keratinous fibers comprising, in a medium suitable for dyeing:
(a) at least one oxidation base; and
(b) at least one coupler chosen from compounds of formula (I) and acid addition salts of any of the foregoing compounds:

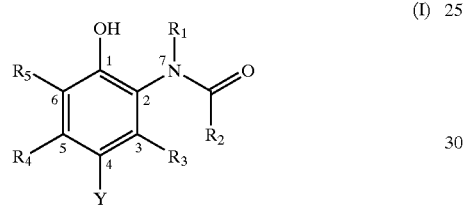

(I)

wherein:
  at least one of $R_1$, $R_2$, $R_3$, $R_4$, and $R_5$, as defined below, is chosen from a group Z, as defined below;
  $R_1$ is chosen from:
    (1) a hydrogen atom;
    (2) linear and branched, saturated and unsaturated groups containing from 1–15 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
      (i) said $R_1$ does not comprise a group chosen from a peroxide group, a diazo group, a nitro group, and a nitroso group, and
      (ii) said $SO_2$ group is not directly linked to the nitrogen atom at the 7-position of formula (I);
    (3) a group Z chosen from cationic groups of formula (II);

(II)

wherein:
  groups B are chosen from linear and branched, saturated and unsaturated groups containing from 1–15 carbon atoms, optionally substituted with at least one substituent chosen from a halogen atom and a group Z, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the proviso that:
    (i) said B does not comprise a group chosen from a peroxide group, a diazo group, a nitro group, and a nitroso group; and
  groups D are chosen from cationic groups of formulae (III) and (IV):

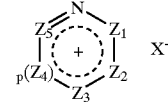

(III)

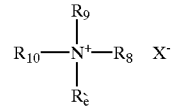

(IV)

wherein:
  group $Z_1$, group $Z_2$, group $Z_3$, and group $Z_4$, which are identical or different, are each chosen from
    1) an oxygen atom and a sulfur atom,
    2) a nitrogen atom, optionally substituted with an $R_{11}$ group, as defined below, and
    3) a carbon atom, optionally substituted with one or two $R_{11}$ groups, as defined below, which are identical or different;
  group $Z_5$ is chosen from
    1) a nitrogen atom and
    2) a carbon atom, optionally substituted with an $R_{11}$ group, as defined below;
  two of the adjacent groups $Z_1$, $Z_2$, $Z_3$, $Z_4$ and $Z_5$ may optionally form a 5- to 7-membered ring, wherein each member is chosen from
    1) an oxygen atom and a sulfur atom,
    2) a nitrogen atom, optionally substituted with an $R_{11}$ group, as defined below, and
    3) a carbon atom, optionally substituted with one or two $R_{11}$ groups, as defined below, which are identical or different;
wherein:
  said groups $R_{11}$ are chosen from:
    a hydrogen atom;
    a group Z as defined above;
    linear and branched, saturated and unsaturated groups containing from 1 to 10 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the proviso that:
    (i) said $R_{11}$ does not comprise a group chosen from a peroxide group, a diazo group, a nitro group, and a nitroso group,
  $Z_6$ is chosen from said $R_{11}$ groups, provided that $Z_6$ is not a hydrogen atom;
  $Z_1$ and $Z_6$, or $Z_5$ and $Z_6$, optionally form a 5- to 7-membered ring chosen from saturated rings and unsaturated rings, wherein said members are each optionally substituted with one or two said radicals $R_{11}$, which are identical or different;

$R_7$, $R_8$, $R_9$, and $R_{10}$, which are identical or different, are each chosen from said groups $R_{11}$;

groups $R_7$, $R_8$, and $R_9$ optionally form, in pairs with the quaternary nitrogen atom to which they are attached, at least one 5- to 7-membered saturated ring, wherein said members are each chosen from
1) an oxygen atom and a sulfur atom,
2) a nitrogen atom, optionally substituted with a said $R_{11}$ group, and
3) a carbon atom, optionally substituted with one or two said $R_{11}$ groups, which are identical or different;

$X^-$ is chosen from organic anions and inorganic anions;

said groups B are linked to said groups D by any one of the atoms of said group D;

n and p, independently of each other, are equal to 0 or 1;

when n=0, then said group $R_{10}$ is optionally a direct bond, wherein said cationic group of formula (IV) is linked directly to said compound of formula (I) by way of the nitrogen cation of said cationic group of formula (IV);

$R_2$ is chosen from:
(1) a hydrogen atom;
(2) a group Z as defined above;
(3) linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
(i) said $R_2$ does not comprise a group chosen from a peroxide group, a diazo group, a nitro group, and a nitroso group; and
(ii) $R_2$ is not a hydroxyl or a thio group;

said $R_1$ and said $R_2$, together with the atoms to which they are attached, optionally form a 5- to 7-membered ring chosen from saturated rings and unsaturated rings, wherein said members are each chosen from a carbon atom, a nitrogen atom, an oxygen atom, a sulfur atom, and a carbonyl group, and said members are optionally substituted with 1 or 2 groups R, wherein R is chosen from linear and branched, saturated and unsaturated, $C_1$–$C_6$ alkyl groups, optionally substituted with at least one halogen atom, wherein at least one carbon atom is optionally and independently replaced by an oxygen atom, a nitrogen atom, a sulfur atom, or an $SO_2$ group, and at least one branch of said branched $C_1$–$C_6$ alkyl group optionally forms at least one ring chosen from saturated and unsaturated 3- to 6-membered rings; with the proviso that:
(i) said R does not comprise a group chosen from a peroxide group, a diazo group, a nitro group, and a nitroso group;

$R_3$ and $R_4$, which are identical or different, are each chosen from:
(1) a hydrogen atom and halogen atoms;
(2) an amino group;
(3) a group Z as defined above;
(4) a Group $A_1$, $A_4$, and $A_5$, as defined below,
(5) a Group $A_1$, $A_2$, $A_3$, $A_4$, and $A_5$, as defined below, wherein said groups are attached to the phenolic nucleus in formula (I) by way of an —O— atom, an —NH— group, an —N($C_1$–$C_3$)alkyl- group, an —O(CO)— group, an —NH(CO)— group, an —N($C_1$–$C_3$)alkyl(CO)— group, an —NH[C=NH]— group, an —NH(CO)NH— group, an —NH(CO)N($C_1$–$C_3$)alkyl- group, an —NH(CO)O— group, an —NHSO$_2$— group, an —NHSO$_2$NH— group, and an —NHSO$_2$N($C_1$–$C_3$)alkyl- group;

wherein said Group $A_1$ is chosen from linear and branched $C_1$–$C_8$ alkyl groups optionally unsaturated and optionally substituted with at least one substituent chosen from:
(i) a group $A_2$, $A_4$, or $A_5$ as defined below;
(ii) one or two groups, which are identical or different, chosen from N—($C_1$–$C_3$)alkylamino, N—($C_1$–$C_3$)alkyl-N—($C_1$–$C_3$)alkylamino, ($C_1$–$C_6$)alkoxy, oxo, alkoxycarbonyl, acyloxy, amide, acylamino, ureyl, sulphoxy, sulphonyl, sulphonamido, sulphonylamino, bromo, cyano, and carboxyl; and
(iii) at least one group chosen from a hydroxyl group, a fluoro group, and a chloro group;

wherein said Group $A_2$ is an aromatic group chosen from a phenyl group, and a naphthyl group, wherein said aromatic group is optionally substituted with one to three groups, which are identical or different, chosen from methyl, trifluoromethyl, ethyl, isopropyl, butyl, pentyl, fluoro, chloro, bromo, methoxy, trifluoromethoxy, ethoxy, propyloxy, acetyloxy, acetyl, and cyano;

wherein said Group $A_3$ is a heteroaromatic group chosen from furanyl, thiophenyl, pyrrolyl, imidazolyl, thiazolyl, oxazolyl, 1,2,3-triazolyl, 1,2,4-triazolyl, isoxazolyl, isothiazolyl, pyrazolyl, pyrazolotriazolyl, pyrazoloimidazolyl, pyrrolotriazolyl, pyrazolopyrimidyl, pyrazolopyridyl, pyridyl, pyrimidyl, benzoimidazolyl, benzoxazolyl, benzothiazolyl, indolyl, indolidinyl, isoindolyl, indazolyl, benzotriazolyl, quinolinyl, benzoimidazolyl and benzopyrimidyl, wherein said heteroaromatic group is optionally substituted with 1 to 3 groups chosen from linear and branched $C_1$–$C_4$ alkyl groups, a $C_1$–$C_4$ monohydroxyalkyl group, a $C_2$–$C_4$ polyhydroxyalkyl group, a carboxyl group, an alkoxycarbonyl group, an amido group, an amino group, a hydroxyl group, and a halogen atom;

wherein said Group $A_4$ is chosen from $C_3$–$C_7$ cycloalkyl groups and a norbornyl group, wherein said $C_3$–$C_7$ cycloalkyl groups and said norbornyl group optionally comprise at least one double bond, and wherein said $C_3$–$C_7$ cycloalkyl groups and said norbornyl group are optionally substituted with 1 or 2 substituents chosen from linear and branched $C_1$–$C_4$ alkyl groups, $C_1$–$C_4$ monohydroxyalkyl groups, $C_2$–$C_4$ polyhydroxyalkyl groups, a carboxyl group, alkoxycarbonyl groups, an amido group, an amino group, a hydroxyl group, and halogen atoms; and wherein said Group $A_5$ is a heterocycle chosen from dihydrofuranyl; tetrahydrofuranyl; butyrolactonyl; dihydrothiophenyl; tetrahydrothiophenyl; tetrahydrothiophenonyl; iminothiolane; dihydropyrrolyl; pyrrolidinyl; pyrrolidinonyl;

imidazolidinonyl; imidazolidinethionyl; oxazolidinyl; oxazolidinonyl; oxazolanethione; thiazolidinyl; isothiazolonyl; mercaptothiazolinyl; pyrazolidinonyl; iminothiolane; dioxolanyl; pentalactone; dioxanyl; dihydropyridinyl; piperidinyl; pentalactam; morpholinyl; pyrazoli(di)nyl; pyrimi(di)nyl; pyrazinyl; piperazinyl; and azepinyl;

$R_5$ is chosen from:
  a hydrogen atom and halogen atoms;
  a group Z as defined above;
  linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
    (i) said $R_5$ does not comprise a group chosen from a peroxide group, a diazo group, a nitro group, and a nitroso group;
    (ii) said $R_5$ is chosen from a group other than a hydroxyl group, a thio group, an amino group, and an optionally substituted sulphonylamino group; and
    (iii) said $R_5$ is not directly linked to the benzene ring of formula (I) by a —NH—NH— group;

said $R_1$ and said $R_3$, together with the atoms to which they are attached, optionally form a 6- to 7-membered saturated ring, wherein said members are each chosen from a carbon atom, a nitrogen atom, an oxygen atom, a sulfur atom, and a carbonyl group, and said members are optionally substituted with 1 or 2 said groups R as defined above, with the proviso that:
  (i) said R does not comprise a group chosen from a peroxide group, a diazo group, a nitro group, and a nitroso group; and said $R_2$ and said $R_3$, together with the atoms to which they are attached, optionally form a 5- to 7-membered saturated ring, wherein said members are each chosen from a carbon atom, a nitrogen atom, an oxygen atom, a sulfur atom, and a carbonyl group, and said members are optionally substituted with 1 or 2 said groups R as defined above, with the proviso that:
  (i) said R does not comprise a group chosen from a peroxide group, a diazo group, a nitro group, and a nitroso group;
  (ii) when said $R_2$ and said $R_3$ form a 5- to 7-membered saturated ring, said $R_3$ optionally is a bond;

Y is chosen from:
  a hydrogen atom and halogen atoms;
  groups —$OR_6$, —$SR_6$ and —NH—$SO_2R_6$, wherein $R_6$ is chosen from linear and branched $C_1$–$C_6$ alkyl groups, optionally substituted with at least one group chosen from a halogen atom, a hydroxyl group, $C_1$–$C_4$ alkoxy groups, an amino group, amino($C_1$–$C_4$ alkyl) groups, wherein at least one branch of said $R_6$ optionally forms at least one 3- to 6-membered ring;
  a phenyl group, optionally substituted with one or two groups chosen from $C_1$–$C_4$ alkyl groups, a trifluoromethyl group, a carboxyl group, $C_1$–$C_4$ alkoxycarbonyl groups, a halogen atom, a hydroxyl group, $C_1$–$C_4$ alkoxy groups, an amino group and amino($C_1$–$C_4$ alkyl) groups; and
  a benzyl group, optionally substituted with one or two oxy groups.

5. A composition for oxidation dyeing keratinous fibers comprising, in a medium suitable for dyeing:
(a) at least one oxidation base; and
(b) at least one coupler chosen from compounds of formula (I) and acid addition salts of any of the foregoing compounds:

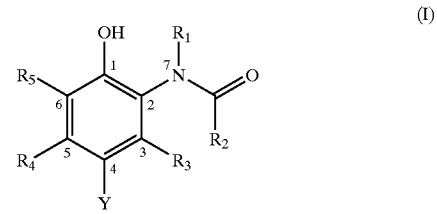

wherein:
  at least one of $R_1$, $R_2$, $R_3$, $R_4$, and $R_5$, as defined below, is chosen from a group Z, as defined below;
  $R_1$ is chosen from:
    (1) a hydrogen atom;
    (2) linear and branched, saturated and unsaturated groups containing from 1–15 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
      (i) said $R_1$ does not comprise a group chosen from a peroxide group, a diazo group, a nitro group, and a nitroso group, and
      (ii) said $SO_2$ group is not directly linked to the nitrogen atom at the 7-position of formula (I);
    (3) a group Z chosen from cationic groups of formula (II);

wherein:
  groups B are chosen from linear and branched, saturated and unsaturated groups containing from 1–15 carbon atoms, optionally substituted with at least one substituent chosen from a halogen atom and a group Z, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the proviso that:
    (i) said B does not comprise a group chosen from a peroxide group, a diazo group, a nitro group, and a nitroso group; and
  groups D are chosen from cationic groups of formulae (III) and (IV):

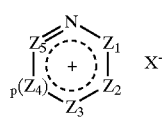

(III)

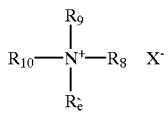

(IV)

wherein:
group $Z_1$, group $Z_2$, group $Z_3$, and group $Z_4$, which are identical or different, are each chosen from
1) an oxygen atom and a sulfur atom,
2) a nitrogen atom, optionally substituted with an $R_{11}$ group, as defined below, and
3) a carbon atom, optionally substituted with one or two $R_{11}$ groups, as defined below, which are identical or different;
group $Z_5$ is chosen from
1) a nitrogen atom and
2) a carbon atom, optionally substituted with an $R_{11}$ group, as defined below;
two of the adjacent groups $Z_1$, $Z_2$, $Z_3$, $Z_4$ and $Z_5$ may optionally form a 5- to 7-membered ring, wherein each member is chosen from
1) an oxygen atom and a sulfur atom,
2) a nitrogen atom, optionally substituted with an $R_{11}$ group, as defined below, and
3) a carbon atom, optionally substituted with one or two $R_{11}$ groups, as defined below, which are identical or different;
wherein:
said groups $R_{11}$ are chosen from:
a hydrogen atom;
a group Z as defined above;
linear and branched, saturated and unsaturated groups containing from 1 to 10 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the proviso that:
(i) said $R_{11}$ does not comprise a group chosen from a peroxide group, a diazo group, a nitro group, and a nitroso group,
$Z_6$ is chosen from said $R_{11}$ groups, provided that $Z_6$ is not a hydrogen atom;
$Z_1$ and $Z_6$, or $Z_5$ and $Z_6$, optionally form a 5- to 7-membered ring chosen from saturated rings and unsaturated rings, wherein said members are each optionally substituted with one or two said radicals $R_{11}$, which are identical or different;
$R_{\dot{e}}$, $R_8$, $R_9$, and $R_{10}$, which are identical or different, are each chosen from said groups $R_{11}$;
groups $R_{\dot{e}}$, $R_8$, and $R_9$ optionally form, in pairs with the quaternary nitrogen atom to which they are attached, at least one 5- to 7-membered saturated ring, wherein said members are each chosen from 1) an oxygen atom and a sulfur atom,
2) a nitrogen atom, optionally substituted with a said $R_{11}$ group, and
3) a carbon atom, optionally substituted with one or two said $R_{11}$ groups, which are identical or different;

$X^-$ is chosen from organic anions and inorganic anions;
said groups B are linked to said groups D by any one of the atoms of said group D;
n and p, independently of each other, are equal to 0 or 1;
when n=0, then said group $R_{10}$ is optionally a direct bond, wherein said cationic group of formula (IV) is linked directly to said compound of formula (I) by way of the nitrogen cation of said cationic group of formula (IV);
$R_2$ is chosen from:
(1) a hydrogen atom;
(2) a group Z as defined above;
(3) linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
(i) said $R_2$ does not comprise a group chosen from a peroxide group, a diazo group, a nitro group, and a nitroso group; and
(ii) $R_2$ is not a hydroxyl or a thio group;
said $R_1$ and said $R_2$, together with the atoms to which they are attached, optionally form a 5- to 7-membered ring chosen from saturated rings and unsaturated rings, wherein said members are each chosen from a carbon atom, a nitrogen atom, an oxygen atom, a sulfur atom, and a carbonyl group, and said members are optionally substituted with 1 or 2 groups R, wherein
R is chosen from linear and branched, saturated and unsaturated, $C_1$–$C_6$ alkyl groups, optionally substituted with at least one halogen atom, wherein at least one carbon atom is optionally and independently replaced by an oxygen atom, a nitrogen atom, a sulfur atom, or an $SO_2$ group, and at least one branch of said branched $C_1$–$C_6$ alkyl group optionally forms at least one ring chosen from saturated and unsaturated 3- to 6-membered rings; with the proviso that:
(i) said R does not comprise a group chosen from a peroxide group, a diazo group, a nitro group, and a nitroso group;
$R_3$ and $R_4$, which are identical or different, are each chosen from:
a hydrogen atom and halogen atoms;
a group Z as defined above;
linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally form at least one 3- to 7-membered ring comprising at least one carbon atom, with the provisos that:
(i) said $R_3$ and said $R_4$ do not comprise a group chosen from a peroxide group, a diazo group, a nitro group, and a nitroso group;

(ii) said $R_3$ and said $R_4$ are not a hydroxyl group; and
(iii) said $R_3$ and said $R_4$ are not directly linked to the benzene ring of formula (I) by an —NH—NH— group;

$R_5$ is chosen from:
  a hydrogen atom and halogen atoms;
  a group Z as defined above;
  a Group $A_1$, $A_4$, and $A_5$, as defined below,
  a Group $A_1$, $A_2$, $A_3$, $A_4$, and $A_5$, as defined below, wherein said groups are attached to the phenolic nucleus in formula (I) by way of an oxygen atom, a sulphur atom, an —NH— group, an —N($C_1$-$C_3$) alkyl- group, an —O(CO)— group, an —NH(CO)— group, an —N($C_1$-$C_3$)alkyl(CO)— group, an —NH [C=NH]— group, an —NH(CO)NH— group, an —NH(CO)N($C_1$-$C_3$)alkyl- group, and an —NH(CO)O— group; and
  wherein said Group $A_1$ is chosen from linear and branched $C_1$-$C_8$ alkyl groups optionally unsaturated and optionally substituted with at least one substituent chosen from:
    (i) a group $A_2$, $A_4$, or $A_5$ as defined below;
    (ii) one or two groups, which are identical or different, chosen from N—($C_1$-$C_3$)alkylamino, N—($C_1$-$C_3$)alkyl-N—($C_1$-$C_3$)alkylamino, ($C_1$-$C_6$)alkoxy, oxo, alkoxycarbonyl, acyloxy, amide, acylamino, ureyl, sulphoxy, sulphonyl, sulphonamido, sulphonylamino, bromo, cyano, and carboxyl; and
    (iii) at least one group chosen from a hydroxyl group, a fluoro group, and a chloro group;
  wherein said Group $A_2$ is an aromatic group chosen from a phenyl group, and a naphthyl group, wherein said aromatic group is optionally substituted with one to three groups, which are identical or different, chosen from methyl, trifluoromethyl, ethyl, isopropyl, butyl, pentyl, fluoro, chloro, bromo, methoxy, trifluoromethoxy, ethoxy, propyloxy, acetyloxy, acetyl, and cyano;
  wherein said Group $A_3$ is a heteroaromatic group chosen from furanyl, thiophenyl, pyrrolyl, imidazolyl, thiazolyl, oxazolyl, 1,2,3-triazolyl, 1,2,4-triazolyl, isoxazolyl, isothiazolyl, pyrazolyl, pyrazolotriazolyl, pyrazoloimidazolyl, pyrrolotriazolyl, pyrazolopyrimidyl, pyrazolopyridyl, pyridyl, pyrimidyl, benzoimidazolyl, benzoxazolyl, benzothiazolyl, indolyl, indolidinyl, isoindolyl, indazolyl, benzotriazolyl, quinolinyl, benzoimidazolyl and benzopyrimidyl, wherein said heteroaromatic group is optionally substituted with 1 to 3 groups chosen from linear and branched $C_1$-$C_4$ alkyl groups, a $C_1$-$C_4$ monohydroxyalkyl group, a $C_2$-$C_4$ polyhydroxyalkyl group, a carboxyl group, an alkoxycarbonyl group, an amido group, an amino group, a hydroxyl group, and a halogen atom;
  wherein said Group $A_4$ is chosen from $C_3$-$C_7$ cycloalkyl groups and a norbornyl group, wherein said $C_3$-$C_7$ cycloalkyl groups and said norbornyl group optionally comprise at least one double bond, and wherein said $C_3$-$C_7$ cycloalkyl groups and said norbornyl group are optionally substituted with 1 or 2 substituents chosen from linear and branched $C_1$-$C_4$ alkyl groups, $C_1$-$C_4$ monohydroxyalkyl groups, $C_2$-$C_4$ polyhydroxyalkyl groups, a carboxyl group, alkoxycarbonyl groups, an amido group, an amino group, a hydroxyl group, and halogen atoms;
  wherein said Group $A_5$ is heterocycle chosen from dihydrofuranyl; tetrahydrofuranyl; butyrolactonyl; dihydrothiophenyl; tetrahydrothiophenyl; tetrahydrothiophenonyl; iminothiolane; dihydropyrrolyl; pyrrolidinyl; pyrrolidinonyl; imidazolidinonyl; imidazolidinethionyl; oxazolidinyl; oxazolidinonyl; oxazolanethione; thiazolidinyl; isothiazolonyl; mercaptothiazolinyl; pyrazolidinonyl; iminothiolane; dioxolanyl; pentalactone; dioxanyl; dihydropyridinyl; piperidinyl; pentalactam; morpholinyl; pyrazoli(di)nyl; pyrimi(di)nyl; pyrazinyl; piperazinyl; and azepinyl;
  said $R_1$ and said $R_3$, together with the atoms to which they are attached, optionally form a 6- to 7-membered saturated ring, wherein said members are each chosen from a carbon atom, a nitrogen atom, an oxygen atom, a sulfur atom, and a carbonyl group, and said members are optionally substituted with 1 or 2 said groups R as defined above, with the proviso that:
    (i) said R does not comprise a group chosen from a peroxide group, a diazo group, a nitro group, and a nitroso group; and
  said $R_2$ and said $R_3$, together with the atoms to which they are attached, optionally form a 5- to 7-membered saturated ring, wherein said members are each chosen from a carbon atom, a nitrogen atom, an oxygen atom, a sulfur atom, and a carbonyl group, and said members are optionally substituted with 1 or 2 said groups R as defined above, with the proviso that:
    (i) said R does not comprise a group chosen from a peroxide group, a diazo group, a nitro group, and a nitroso group;
    (ii) when said $R_2$ and said $R_3$ form a 5- to 7-membered saturated ring, said $R_3$ optionally is a bond;
  Y is chosen from:
    a hydrogen atom and halogen atoms;
    groups —$OR_6$, —$SR_6$ and —NH—$SO_2R_6$, wherein $R_6$ is chosen from linear and branched $C_1$-$C_6$ alkyl groups, optionally substituted with at least one group chosen from a halogen atom, a hydroxyl group, $C_1$-$C_4$ alkoxy groups, an amino group, amino($C_1$-$C_4$ alkyl) groups, wherein at least one branch of said $R_6$ optionally forms at least one 3- to 6-membered ring;
    a phenyl group, optionally substituted with one or two groups chosen from $C_1$-$C_4$ alkyl groups, a trifluoromethyl group, a carboxyl group, $C_1$-$C_4$ alkoxycarbonyl groups, a halogen atom, a hydroxyl group, $C_1$-$C_4$ alkoxy groups, an amino group and amino ($C_1$-$C_4$ alkyl) groups; and
    a benzyl group, optionally substituted with one or two oxy groups.

6. A composition according to claim 1, wherein said $R_1$ is chosen from:
  (1) a hydrogen atom;
  (2) a group chosen from methyl, ethyl, isopropyl, allyl, phenyl, benzyl, fluorobenzyl, hydroxybenzyl, difluorobenzyl, trifluorobenzyl, chlorobenzyl, bromobenzyl, methoxybenzyl, dimethoxybenzyl, (trifluoromethoxy)benzyl, 3,4-methylenedioxybenzyl, 6-chloropiperonyl, 4-methylthiobenzyl, 4-methylsulfonylbenzyl, 4-acetylaminobenzyl, 4-carboxybenzyl, 1-naphthomethyl, and 2-naphthomethyl; and
  (3) a group chosen from 2-hydroxyethyl, 2-methoxyethyl and 2-ethoxyethyl.

7. A composition according to claim 6, wherein said $R_1$ is chosen from a hydrogen atom and a methyl group.

8. A composition according to claim 1, wherein $R_2$ is chosen from a group Z; a group (3) chosen from methyl, ethyl, propyl, isopropyl, butyl, isobutyl, tert-butyl, pentyl, isopentyl, neopentyl, hexyl; cyclopropyl, cyclobutyl, cyclopentyl, cyclopentyl-methyl, 3-cyclopentylpropyl, cyclohexyl, 2-cyclohexylethyl, norborn-2-yl, vinyl, 1-methylvinyl, 2-methylvinyl, 2,2-dimethylvinyl, allyl, 3-butenyl, phenyl, methylphenyl, dimethylphenyl, 2,4,6-trimethylphenyl, 4-ethylphenyl, (trifluoromethyl)phenyl, hydroxyphenyl, methoxyphenyl, ethoxyphenyl, acetoxyphenyl, (trifluoromethoxy)phenyl, aminophenyl, 4-dimethylaminophenyl, fluorophenyl, difluorophenyl, fluoro(trifluoromethyl)phenyl, chlorophenyl, dichlorophenyl, bromophenyl, naphth-1-yl, naphth-2-yl, (2-methoxy)naphth-1-yl, benzyl, 4'-methoxybenzyl, 2',5'-dimethoxybenzyl, 3',4'-dimethoxybenzyl, 4'-fluorobenzyl, 4'-chlorobenzyl, phenethyl, 2-phenylvinyl, (1-naphthyl)methyl, (2-naphthyl)methyl; tetrahydrofuran-2-yl, furan-2-yl, 5-methyl-2-(trifluoromethyl)furan-3-yl, 2-methyl-5-phenylfuran-3-yl, thiophen-2-yl, (thiophen-2-yl)methyl, 3-chlorothiophen-2-yl, 2,5-dichlorothiophen-3-yl, benzothiophen-2-yl, 3-chlorobenzothiophen-2-yl, isoxazol-5-yl, 5-methylisoxazol-3-yl, 3,5-dimethylisoxazol-4-yl, 1,3-dimethylpyrazol-5-yl, 1-ethyl-3-methylpyrazol-5-yl, 1-tert-butyl-3-methylpyrazol-5-yl, 3-tert-butyl-1-methylpyrazol-5-yl, 4-bromo-1-ethyl-3-methylpyrazol-5-yl, indol-3-ylcarboxyl, pyridinyl, chloropyridinyl, dichloropyridinyl, 5-(bromo)pyridin-3-yl, piperazin-2-yl, quinoxal-2-yl, fluoromethyl, difluoromethyl, trifluoromethyl, 1,1,2,2-tetrafluoroethyl, pentafluoroethyl, heptafluoropropyl, 1,1,2,2,3,3,4,4-octafluorobutyl, nonafluorobutyl, chloromethyl, chloroethyl, 1,1-dimethyl-2-chloroethyl, 1,2-dichloroethyl, 1-chloropropyl, 3-chloropropyl, 4-chlorobutyl, hydroxymethyl, methoxymethyl, phenoxymethyl, (4-chlorophenoxy)methyl, benzyloxymethyl, acetoxymethyl, 1,2-dihydroxyethyl, 1-phenoxyethyl, 1-acetoxyethyl, 2-(2-carboxyethoxy)ethyl, 1-phenoxyethyl, 1-acetoxyethyl, methoxycarbonyl, ethoxycarbonyl, (methoxycarbonyl)methyl, 2-carboxyethyl, 2-(methoxycarbonyl)ethyl, 2-carboxycyclopropyl, 2-carboxycyclohexane; methoxy, ethoxy, propoxy, isopropoxy, butoxy, isobutoxy, pentoxy, neopentoxy, hexyloxy, cyclopentyloxy, cyclohexyloxy, vinyloxy, allyloxy, propargyloxy, chloromethoxy, 1-chloroethoxy, 2-methoxyethoxy, 4-chlorobutoxy, phenoxy, 4-methylphenoxy, 4-fluorophenoxy, 4-bromophenoxy, 4-chlorophenoxy, 4-methoxyphenoxy, naphth-2-yloxy, benzyloxy; amino, methylamino, ethylamino, propylamino, isopropylamino, butylamino, cyclohexylamino, allylamino, 2-chloroethylamino, 3-chloropropylamino, carboxymethylamino, phenylamino, fluorophenylamino, (trifluoromethyl)phenylamino, chlorophenylamino, bromophenylamino, 4-acetylphenylamino, methoxyphenylamino, (trifluoromethoxy)phenylamino, naphth-1-ylamino, benzylamino, phenethylamino, pyrid-3-ylamino, dimethylamino, 1-pyrrolidinyl and 4-morpholinyl groups.

9. A composition according to claim 1, wherein said $R_1$ and said $R_2$ together with the atoms to which they are attached form a ring, wherein said ring is chosen from 2-pyrrolidinon-1-yl, methyl-2-pyrrolidinon-1-yl, 5-carboxy-2-pyrrolidinon-1-yl, 5-methoxycarbonyl-2-pyrrolidinon-1-yl, pyrazolinon-1-yl, succinimid-1-yl, 3,5-diketo-pyrazolidin-1-yl, oxindolin-1-yl, maleimid-1-yl, isoindole-1,3-dion-2-yl, 2-piperidinon-1-yl and glutarimid-1-yl.

10. A composition for oxidation dyeing keratinous fibers comprising, in a medium suitable for dyeing:
(a) at least one oxidation base; and
(b) at least one coupler chosen from compounds of formula (I) and acid addition salts of any of the foregoing compounds:

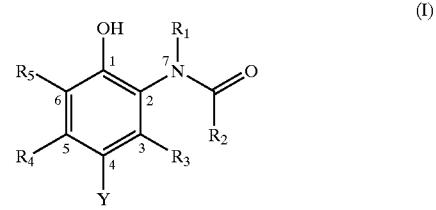

wherein:
at least one of $R_1$, $R_2$, $R_3$, $R_4$, and $R_5$, as defined below, is chosen from a cationic group, as defined below;
$R_1$ is chosen from:
(1) a hydrogen atom;
(2) linear and branched, saturated and unsaturated groups containing from 1–15 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
(i) said $R_1$ does not comprise a group chosen from a peroxide group, a diazo group, a nitro group, and a nitroso group, and
(ii) said $SO_2$ group is not directly linked to the nitrogen atom at the 7-position of formula (I);
(3) a group Z chosen from cationic groups of formula (II);

wherein:
groups B are chosen from linear and branched, saturated and unsaturated groups containing from 1–15 carbon atoms, optionally substituted with at least one substituent chosen from a halogen atom and a group Z, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the proviso that:
(i) said B does not comprise a group chosen from a peroxide group, a diazo group, a nitro group, and a nitroso group; and
groups D are chosen from cationic groups of formulae (III) and (IV):

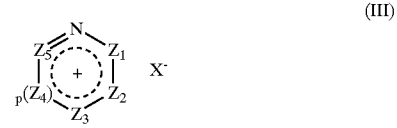

-continued

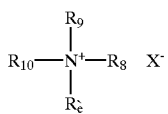
(IV)

wherein:
group $Z_1$, group $Z_2$, group $Z_3$, and group $Z_4$, which are identical or different, are each chosen from
  1) an oxygen atom and a sulfur atom,
  2) a nitrogen atom, optionally substituted with an $R_{11}$ group, as defined below, and
  3) a carbon atom, optionally substituted with one or two $R_{11}$ groups, as defined below, which are identical or different;
group $Z_5$ is chosen from
  1) a nitrogen atom and
  2) a carbon atom, optionally substituted with an $R_{11}$ group, as defined below;
two of the adjacent groups $Z_1$, $Z_2$, $Z_3$, $Z_4$ and $Z_5$ may optionally form a 5- to 7-membered ring, wherein each member is chosen from
  1) an oxygen atom and a sulfur atom,
  2) a nitrogen atom, optionally substituted with an $R_{11}$ group, as defined below, and
  3) a carbon atom, optionally substituted with one or two $R_{11}$ groups, as defined below, which are identical or different;
wherein:
said groups $R_{11}$ are chosen from:
  a hydrogen atom;
  a group Z as defined above;
  linear and branched, saturated and unsaturated groups containing from 1 to 10 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the proviso that:
  (i) said $R_{11}$ does not comprise a group chosen from a peroxide group, a diazo group, a nitro group, and a nitroso group,
$Z_6$ is chosen from said $R_{11}$ groups, provided that $Z_6$ is not a hydrogen atom;
$Z_1$ and $Z_6$, or $Z_5$ and $Z_6$, optionally form a 5- to 7-membered ring chosen from saturated rings and unsaturated rings, wherein said members are each optionally substituted with one or two said radicals $R_{11}$, which are identical or different;
$R_7$, $R_8$, $R_9$, and $R_{10}$, which are identical or different, are each chosen from said groups $R_{11}$;
groups $R_7$, $R_8$, and $R_9$ optionally form, in pairs with the quaternary nitrogen atom to which they are attached, at least one 5- to 7-membered saturated ring, wherein said members are each chosen from
  1) an oxygen atom and a sulfur atom,
  2) a nitrogen atom, optionally substituted with a said $R_{11}$ group, and
  3) a carbon atom, optionally substituted with one or two said $R_{11}$ groups, which are identical or different;

$X^-$ is chosen from organic anions and inorganic anions;
said groups B are linked to said groups D by any one of the atoms of said group D;
n and p, independently of each other, are equal to 0 or 1;
when n=0, then said group $R_{10}$ is optionally a direct bond, wherein said cationic group of formula (IV) is linked directly to said compound of formula (I) by way of the nitrogen cation of said cationic group of formula (IV);
$R_2$ is chosen from:
  (1) a group (G2) chosen from methyl, ethyl, propyl, allyl, phenyl, tetrahydrofuran-2-yl, furan-2-yl, thiophen-2-yl, pyridinyl, piperazin-2-yl, fluoromethyl, chloromethyl, 2-chloroethyl, methoxymethyl, acetoxymethyl, 1,2-dihydroxyethyl, methoxycarbonyl, 2-carboxyethyl, methoxy, ethoxy, propoxy, allyloxy, 2-chloroethoxy, 2-methoxyethoxy, amino, ethylamino, allylamino, 2-chloroethylamino, pyridylamino, dimethylamino, 1-pyrrolidinyl and 4-morpholinyl groups;
  (2) a group chosen from $—D_1$, $—E—D_1$, $—O—E—D_1$, and $—NH—E—D_1$, wherein $—E—$ is a group $—(CH_2)_q—$, q is an integer equal to 1 or 2, and $D_1$ is a group D' chosen from 3-methylimidazolidinium-1-yl, 3-(2-hydroxyethyl)imidazolidinium-1-yl, 1,2,4-triazolinium-1-yl, 1,2,4-triazolinium-4-yl, N—($C_1$–$C_4$)alkylpyridinium-2-yl, N—($C_1$–$C_4$)alkylpyridinium-3-yl, N—($C_1$–$C_4$)alkylpyridinium-4-yl, N-(2-hydroxyethyl)pyridinium-2-yl, N-(2-hydroxyethyl)pyridinium-3-yl, N-(2-hydroxyethyl)pyridinium-4-yl, pyridinium-1-yl, tri($C_1$–$C_4$)alkylammonium-N-yl, 1-methylpiperidinium-1-yl and 1,4-dimethylpiperazinium-1-yl;
said $R_1$ and said $R_2$, together with the atoms to which they are attached, optionally form a 5- to 7-membered ring chosen from saturated rings and unsaturated rings, wherein said members are each chosen from a carbon atom, a nitrogen atom, an oxygen atom, a sulfur atom, and a carbonyl group, and said members are optionally substituted with 1 or 2 groups R, wherein
R is chosen from linear and branched, saturated and unsaturated, $C_1$–$C_6$ alkyl groups, optionally substituted with at least one halogen atom, wherein at least one carbon atom is optionally and independently replaced by an oxygen atom, a nitrogen atom, a sulfur atom, or an $SO_2$ group, and at least one branch of said branched $C_1$–$C_6$ alkyl group optionally forms at least one ring chosen from saturated and unsaturated 3- to 6-membered rings; with the proviso that:
  (i) said R does not comprise a group chosen from a peroxide group, a diazo group, a nitro group, and a nitroso group;
$R_3$ and $R_4$, which are identical or different, are each chosen from:
  a hydrogen atom and halogen atoms;
  a group Z as defined above;
  linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally form at least one 3- to 7-membered ring comprising at least one carbon atom, with the provisos that:

(i) said R₃ and said R₄ do not comprise a group chosen from a peroxide group, a diazo group, a nitro group, and a nitroso group;
(ii) said R₃ and said R₄ are not a hydroxyl group; and
(iii) said R₃ and said R₄ are not directly linked to the benzene ring of formula (I) by an —NH—NH— group;

R₅ is chosen from:
  a hydrogen atom and halogen atoms;
  a group Z as defined above;
  linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an SO₂ group, and at least one branch of said branched groups optionally forms at least one 3- to 7-membered ring comprising at least one carbon atom, with the provisos that:
    (i) said R₅ does not comprise a group chosen from a peroxide group, a diazo group, a nitro group, and a nitroso group;
    (ii) said R₅ is chosen from a group other than a hydroxyl group, a thio group, an amino group, and an optionally substituted sulphonylamino group; and
    (iii) said R₅ is not directly linked to the benzene ring of formula (I) by a —NH—NH— group;

said R₁ and said R₃, together with the atoms to which they are attached, optionally form a 6- to 7-membered saturated ring, wherein said members are each chosen from a carbon atom, a nitrogen atom, an oxygen atom, a sulfur atom, and a carbonyl group, and said members are optionally substituted with 1 or 2 said groups R as defined above, with the proviso that:
  (i) said R does not comprise a group chosen from a peroxide group, a diazo group, a nitro group, and a nitroso group; and said R₂ and said R₃, together with the atoms to which they are attached, optionally form a 5- to 7-membered saturated ring, wherein said members are each chosen from a carbon atom, a nitrogen atom, an oxygen atom, a sulfur atom, and a carbonyl group, and said members are optionally substituted with 1 or 2 said groups R as defined above, with the proviso that:
  (i) said R does not comprise a group chosen from a peroxide group, a diazo group, a nitro group, and a nitroso group;
  (ii) when said R₂ and said R₃ form a 5- to 7-membered saturated ring, said R₃ optionally is a bond;

Y is chosen from:
  a hydrogen atom and halogen atoms;
  groups —OR₆, —SR₆ and —NH—SO₂R₆, wherein
    R₆ is chosen from linear and branched C₁–C₆ alkyl groups, optionally substituted with at least one group chosen from a halogen atom, a hydroxyl group, C₁–C₄ alkoxy groups, an amino group, amino(C₁–C₄ alkyl) groups, wherein at least one branch of said R₆ optionally forms at least one 3- to 6-membered ring;
  a phenyl group, optionally substituted with one or two groups chosen from C₁–C₄ alkyl groups, a trifluoromethyl group, a carboxyl group, C₁–C₄ alkoxycarbonyl groups, a halogen atom, a hydroxyl group, C₁–C₄ alkoxy groups, an amino group and amino (C₁–C₄ alkyl) groups; and
  a benzyl group, optionally substituted with one or two oxy groups.

11. A composition according to claim 10, wherein said R₂ is chosen from methyl, methoxymethyl, 2-carboxyethyl, methoxy, amino, ethylamino and 1-pyrrolidinyl groups; and said groups —D₁, —E—D₁, —O—E—D₁ and —NH—E—D₁.

12. A composition for oxidation dyeing keratinous fibers comprising, in a medium suitable for dyeing:
(a) at least one oxidation base; and
(b) at least one coupler chosen from compounds of formula (I) and acid addition salts of any of the foregoing compounds:

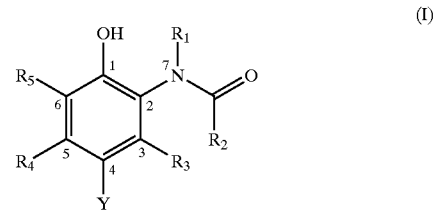

(I)

wherein:
  at least one of R₁, R₂, R₃, R₄, and R₅, as defined below, is chosen from a group Z, as defined below;
  R₁ is chosen from:
    (1) a hydrogen atom;
    (2) linear and branched, saturated and unsaturated groups containing from 1–15 carbon atoms, optionally substituted with at least one halogen atom, wherein at least one carbon atom is optionally and independently replaced by an oxygen atom, a nitrogen atom, a sulfur atom, or an SO₂ group, and at least one branch of said branched groups optionally forms at least one 3- to 7-membered ring comprising at least one carbon atom, with the provisos that:
      (i) said R₁ does not comprise a group chosen from a peroxide group, a diazo group, a nitro group, and a nitroso group, and
      (ii) said SO₂ group is not directly linked to the nitrogen atom at the 7-position of formula (I);
    (3) a group Z chosen from cationic groups of formula (II);

(II)

wherein:
  groups B are chosen from linear and branched, saturated and unsaturated groups containing from 1–15 carbon atoms, optionally substituted with at least one substituent chosen from a halogen atom and a group Z, wherein at least one carbon atom is optionally and independently replaced by an oxygen atom, a nitrogen atom, a sulfur atom, or an SO₂ group, and at least one branch of said branched groups optionally forms at least one 3- to 7-membered ring comprising at least one carbon atom, with the proviso that:
    (i) said B does not comprise a group chosen from a peroxide group, a diazo group, a nitro group, and a nitroso group; and
  groups D are chosen from cationic groups of formulae (III) and (IV):

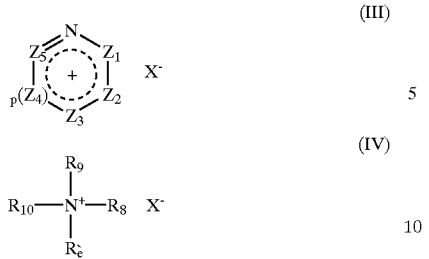

(III)

(IV)

wherein:
group $Z_1$, group $Z_2$, group $Z_3$, and group $Z_4$, which are identical or different, are each chosen from
1) an oxygen atom and a sulfur atom,
2) a nitrogen atom, optionally substituted with an $R_{11}$ group, as defined below, and
3) a carbon atom, optionally substituted with one or two $R_{11}$ groups, as defined below, which are identical or different;
group $Z_5$ is chosen from
1) a nitrogen atom and
2) a carbon atom, optionally substituted with an $R_{11}$ group, as defined below;
two of the adjacent groups $Z_1$, $Z_2$, $Z_3$, $Z_4$ and $Z_5$ may optionally form a 5- to 7-membered ring, wherein each member is chosen from
1) an oxygen atom and a sulfur atom,
2) a nitrogen atom, optionally substituted with an $R_{11}$ group, as defined below, and
3) a carbon atom, optionally substituted with one or two $R_{11}$ groups, as defined below, which are identical or different;
wherein:
said groups $R_{11}$ are chosen from:
a hydrogen atom;
a group Z as defined above;
linear and branched, saturated and unsaturated groups containing from 1 to 10 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the proviso that:
(i) said $R_{11}$ does not comprise a group chosen from a peroxide group, a diazo group, a nitro group, and a nitroso group,
$Z_6$ is chosen from said $R_{11}$ groups, provided that $Z_6$ is not a hydrogen atom;
$Z_1$ and $Z_6$, or $Z_5$ and $Z_6$, optionally form a 5- to 7-membered ring chosen from saturated rings and unsaturated rings, wherein said members are each optionally substituted with one or two said radicals $R_{11}$, which are identical or different;
$R_{\dot{e}}$, $R_8$, $R_9$, and $R_{10}$, which are identical or different, are each chosen from said groups $R_{11}$;
groups $R_{\dot{e}}$, $R_8$, and $R_9$ optionally form, in pairs with the quaternary nitrogen atom to which they are attached, at least one 5- to 7-membered saturated ring, wherein said members are each chosen from
1) an oxygen atom and a sulfur atom,
2) a nitrogen atom, optionally substituted with a said $R_{11}$ group, and
3) a carbon atom, optionally substituted with one or two said $R_{11}$ groups, which are identical or different;
$X^-$ is chosen from organic anions and inorganic anions;
said groups B are linked to said groups D by any one of the atoms of said group D;
n and p, independently of each other, are equal to 0 or 1;
when n=0, then said group $R_{10}$ is optionally a direct bond, wherein said cationic group of formula (IV) is linked directly to said compound of formula (I) by way of the nitrogen cation of said cationic group of formula (IV);
$R_2$ is chosen from:
(1) a hydrogen atom;
(2) a group Z as defined above;
(3) linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
(i) said $R_2$ does not comprise a group chosen from a peroxide group, a diazo group, a nitro group, and a nitroso group; and(ii) $R_2$ is not a hydroxyl or a thio group;
said $R_1$ and said $R_2$, together with the atoms to which they are attached, optionally form a 5- to 7-membered ring chosen from saturated rings and unsaturated rings, wherein said members are each chosen from a carbon atom, a nitrogen atom, an oxygen atom, a sulfur atom, and a carbonyl group, and said members are optionally substituted with 1 or 2 groups R, wherein
R is chosen from linear and branched, saturated and unsaturated, $C_1$–$C_6$ alkyl groups, optionally substituted with at least one halogen atom, wherein at least one carbon atom is optionally and independently replaced by an oxygen atom, a nitrogen atom, a sulfur atom, or an $SO_2$ group, and at least one branch of said branched $C_1$–$C_6$ alkyl group optionally forms at least one ring chosen from saturated and unsaturated 3- to 6-membered rings; with the proviso that:
(i) said R does not comprise a group chosen from a peroxide group, a diazo group, a nitro group, and a nitroso group;
$R_3$ is chosen from:
(1) a hydrogen atom and a chlorine atom;
(2) said group Z;
(3) a group chosen from methyl, hydroxymethyl, methoxymethyl, 1-hydroxyethyl, aminomethyl, methylaminomethyl, methoxy, acetoxy, amino, methylamino and 2-hydroxyethylamino;
(4) a group —NH(CO)$R_{12}$ wherein $R_{12}$ is a group (G1) chosen from methyl, ethyl, propyl, isopropyl, butyl, isobutyl, tert-butyl, pentyl, isopentyl, neopentyl, hexyl; cyclopropyl, cyclobutyl, cyclopentyl, cyclopentylmethyl, 3-cyclopentylpropyl, cyclohexyl, 2-cyclohexylethyl, norborn-2-yl, vinyl, 1-methylvinyl, 2-methylvinyl, 2,2-dimethylvinyl, allyl, 3-butenyl, phenyl, methylphenyl, dimethylphenyl, 2,4,6-trimethylphenyl, 4-ethylphenyl, (trifluoromethyl)phenyl, hydroxyphenyl, methoxyphenyl, ethoxyphenyl, acetoxyphenyl, (trifluoromethoxy)phenyl, aminophenyl, 4-dimethylaminophenyl, fluorophenyl, difluorophenyl, fluoro(trifluoromethyl)phenyl, chlorophenyl, dichlorophenyl, bromophenyl, naphth-1-yl, naphth-2-yl, (2-methoxy)naphth-1-yl, benzyl, 4'-methoxybenzyl, 2',5'-dimethoxybenzyl, 3',4'-dimethoxybenzyl, 4'-fluorobenzyl, 4'-chlorobenzyl, phenethyl, 2-phenylvinyl, (1-naphthyl)methyl, (2-naphthyl)methyl; tetrahydrofuran-2-yl, furan-2-yl, 5-methyl-2-(trifluoromethyl)furan-3-yl, 2-methyl-5-phenylfuran-3-yl, thiophen-2-yl, (thiophen-2-yl)methyl, 3-chlorothiophen-2-yl, 2,5-dichlorothiophen-3-yl, benzothiophen-2-yl, 3-chlorobenzothiophen-2-yl, isoxazol-5-yl, 5-methylisoxazol-3-yl, 3,5-dimethylisoxazol-4-yl, 1,3-dimethylpyrazol-5-yl, 1-ethyl-3-methylpyrazol-5-yl, 1-tert-butyl-3-methylpyrazol-5-yl, 3-tert-butyl-1-methylpyrazol-5-yl, 4-bromo-1-ethyl-3-methylpyrazol-5-yl, indol-3-ylcarboxyl, pyridinyl, chloropyridinyl, dichloropyridinyl, 5-(bromo)pyridin-3-yl, piperazin-2-yl, quinoxal-2-yl, fluoromethyl, difluoromethyl, trifluoromethyl, 1,1,2,2-tetrafluoro-ethyl, pentafluoroethyl, heptafluoropropyl, 1,1,2,2,3,3,4,4-octafluorobutyl, nonafluorobutyl, chloromethyl, chloroethyl 1,1-dimethyl-2-chloroethyl, 1,2-dichloroethyl, 1-chloropropyl, 3-chloropropyl, 4-chlorobutyl, hydroxymethyl, methoxymethyl, phenoxymethyl, (4-chlorophenoxy)methyl, benzyloxymethyl, acetoxymethyl, 1,2-dihydroxyethyl, 1-phenoxyethyl, 1-acetoxyethyl, 2-(2-carboxyethoxy)ethyl, 1-phenoxyethyl, 1-acetoxyethyl, methoxycarbonyl, ethoxycarbonyl, (methoxycarbonyl)methyl, 2-carboxyethyl, 2-(methoxycarbonyl)ethyl, 2-carboxycyclopropyl, 2-carboxycyclohexane; methoxy, ethoxy, propoxy, isopropoxy, butoxy, isobutoxy, pentoxy, neopentoxy, hexyloxy, cyclopentyloxy, cyclohexyloxy, vinyloxy, allyloxy, propargyloxy, chloromethoxy, 1-chloroethoxy, 2-methoxyethoxy, 4-chlorobutoxy, phenoxy, 4-methylphenoxy, 4-fluorophenoxy, 4-bromophenoxy, 4-chlorophenoxy, 4-methoxyphenoxy, naphth-2-yloxy, benzyloxy; amino, methylamino, ethylamino, propylamino, isopropylamino, butylamino, cyclohexylamino, allylamino, 2-chloroethylamino, 3-chloropropylamino, carboxymethylamino, phenylamino, fluorophenylamino, (trifluoromethyl)phenylamino, chlorophenylamino, bromophenylamino, 4-acetylphenylamino, methoxyphenylamino, (trifluoromethoxy)phenylamino, naphth-1-ylamino, benzylamino, phenethylamino, pyrid-3-ylamino, dimethylamino, 1-pyrrolidinyl and 4-morpholinyl; and (5) a group —NHSO$_2$R$_{13}$, in which R$_{13}$ is a group (G3) chosen from methyl, trifluoromethyl, ethyl, 2-chloroethyl, propyl, 3-chloropropyl, isopropyl, butyl, thiophen-2-yl, hydroxyl, ethoxy and dimethylamino;

R$_4$ is chosen from:
a hydrogen atom and halogen atoms;
a group Z as defined above;
linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an SO$_2$ group, and at least one branch of said branched groups optionally form at least one 3- to 7-membered ring comprising at least one carbon atom, with the provisos that:
(i) said R$_4$ does not comprise a group chosen from a peroxide group, a diazo group, a nitro group, and a nitroso group; and
(iii) said R$_4$ is not directly linked to the benzene ring of formula (I) by an —NH—NH— group;

R$_5$ is chosen from:
a hydrogen atom and halogen atoms;
a group Z as defined above;
linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an SO$_2$ group, and at least one branch of said branched groups optionally forms at least one 3- to 7-membered ring comprising at least one carbon atom, with the provisos that:
(i) said R$_5$ does not comprise a group chosen from a peroxide group, a diazo group, a nitro group, and a nitroso group;
(ii) said R$_5$ is chosen from a group other than a hydroxyl group, a thio group, an amino group, and an optionally substituted sulphonylamino group; and
(iii) said R$_5$ is not directly linked to the benzene ring of formula (I) by a —NH—NH— group;

said R$_1$ and said R$_3$, together with the atoms to which they are attached, optionally form a 6- to 7-membered saturated ring, wherein said members are each chosen from a carbon atom, a nitrogen atom, an oxygen atom, a sulfur atom, and a carbonyl group, and said members are optionally substituted with 1 or 2 said groups R as defined above, with the proviso that:
(i) said R does not comprise a group chosen from a peroxide group, a diazo group, a nitro group, and a nitroso group; and said R$_2$ and said R$_3$, together with the atoms to which they are attached, optionally form a 5- to 7-membered saturated ring, wherein said members are each chosen from a carbon atom, a nitrogen atom, an oxygen atom, a sulfur atom, and a carbonyl group, and said members are optionally substituted with 1 or 2 said groups R as defined above, with the proviso that:
(i) said R does not comprise a group chosen from a peroxide group, a diazo group, a nitro group, and a nitroso group;
(ii) when said R$_2$ and said R$_3$ form a 5- to 7-membered saturated ring, said R$_3$ optionally is a bond;

Y is chosen from:
a hydrogen atom and halogen atoms;
groups —OR$_6$, —SR$_6$ and —NH—SO$_2$R$_6$, wherein R$_6$ is chosen from linear and branched C$_1$–C$_6$ alkyl groups, optionally substituted with at least one group chosen from a halogen atom, a hydroxyl group, C$_1$–C$_4$ alkoxy groups, an amino group, amino(C$_1$–C$_4$ alkyl) groups, wherein at least one branch of said R$_6$ optionally forms at least one 3- to 6-membered ring;
a phenyl group, optionally substituted with one or two groups chosen from C$_1$–C$_4$ alkyl groups, a trifluoromethyl group, a carboxyl group, $C_1$–$C_4$ alkoxycarbonyl groups, a halogen atom, a hydroxyl group, $C_1$–$C_4$ alkoxy groups, an amino group and amino ($C_1$–$C_4$ alkyl) groups; and a benzyl group, optionally substituted with one or two oxy groups.

13. A composition according to claim 1, wherein said $R_1$ and said $R_3$ form a ring together with the nitrogen atom at the 7-position of the compounds of formula (I), wherein —$R_1R_3$— is —$CH_2CH_2CH_2$—.

14. A composition according to claim 1, wherein said $R_2$ and said $R_3$ form a ring together with the nitrogen atom at the 7-position of the compounds of formula (I), wherein —$R_2R_3$— is chosen from —$CH_2$—, —$C(CH_3)_2$—, and —$CH_2CH_2$—.

15. A composition according to claim 12, wherein said $R_3$ is chosen from:

(1) a hydrogen atom;

(2) a group chosen from methyl, hydroxymethyl, aminomethyl, hydroxyl, methoxy, amino, methylamino, methanesulfonylamino, ethanesulfonylamino, and dimethylaminosulfonylamino;

(3) a group —NH(CO)$R_{14}$ wherein $R_{14}$ is chosen from group (G2) chosen from methyl, ethyl, propyl, allyl, phenyl, tetrahydrofuran-2-yl, furan-2-yl, thiophen-2-yl, pyridinyl, piperazin-2-yl, fluoromethyl, chloromethyl, 2-chloroethyl, methoxymethyl, acetoxymethyl, 1,2-dihydroxyethyl, methoxycarbonyl, 2-carboxyethyl, methoxy, ethoxy, propoxy, allyloxy, 2-chloroethoxy, 2-methoxyethoxy, amino, ethylamino, allylamino, 2-chloroethylamino, pyridylamino, dimethylamino, 1-pyrrolidinyl and 4-morpholinyl; and (4) a group —O—E—$D_2$, —NH—E—$D_2$, —$CH_2$O—E—$D_2$, —$CH_2$NH—E—$D_2$, —$CH_2$NH(CO)—$D_2$, —NH(CO)—$D_2$, —NH(CO)—E—$D_2$, —NH(CO)O—E—$D_2$, —NH(CO)NH—E—$D_2$ and —NH(SO$_2$)—E—$D_2$, wherein —E— is a ($CH_2$)$_q$— group, q is an integer equal to 1 or 2, and $D_2$ is a group D' chosen from 3-methylimidazolidinium-1-yl, 3-(2-hydroxyethyl)imidazolidinium-1-yl, 1,2,4-triazolinium-1-yl, 1,2,4-triazolinium-4-yl, N—($C_1$–$C_4$)alkylpyridinium-2-yl, N—($C_1$–$C_4$)alkylpyridinium-3-yl, N—($C_1$–$C_4$)alkylpyridinium-4-yl, N-(2-hydroxyethyl)pyridinium-2-yl, N-(2-hydroxyethyl)pyridinium-3-yl, N-(2-hydroxyethyl)pyridinium-4-yl, pyridinium-1-yl, tri($C_1$–$C_4$)alkylammonium-N-yl, 1-methylpiperidinium-1-yl and 1,4-dimethylpiperazinium-1-yl.

16. A composition for oxidation dyeing keratinous fibers comprising, in a medium suitable for dyeing:
(a) at least one oxidation base; and
(b) at least one coupler chosen from compounds of formula (I) and acid addition salts of any of the foregoing compounds:

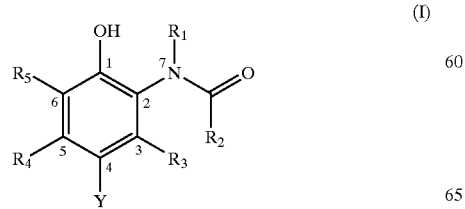

(I)

wherein:
at least one of $R_1$, $R_2$, $R_3$, $R_4$, and $R_5$, as defined below, is chosen from a group Z, as defined below;

$R_1$ is chosen from:
(1) a hydrogen atom;
(2) linear and branched, saturated and unsaturated groups containing from 1–15 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
(i) said $R_1$ does not comprise a group chosen from a peroxide group, a diazo group, a nitro group, and a nitroso group, and
(ii) said $SO_2$ group is not directly linked to the nitrogen atom at the 7-position of formula (I);
(3) a group Z chosen from cationic groups of formula (II);

(II)

wherein:
groups B are chosen from linear and branched, saturated and unsaturated groups containing from 1–15 carbon atoms, optionally substituted with at least one substituent chosen from a halogen atom and a group Z, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the proviso that:
(i) said B does not comprise a group chosen from a peroxide group, a diazo group, a nitro group, and a nitroso group; and
groups D are chosen from cationic groups of formulae (III) and (IV):

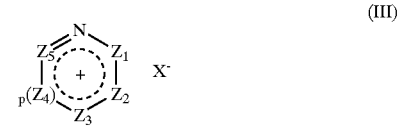

(III)

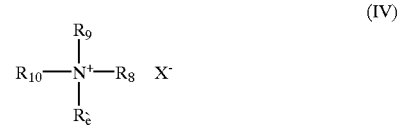

(IV)

wherein:
group $Z_1$, group $Z_2$, group $Z_3$, and group $Z_4$, which are identical or different, are each chosen from
1) an oxygen atom and a sulfur atom,
2) a nitrogen atom, optionally substituted with an $R_{11}$ group, as defined below, and
3) a carbon atom, optionally substituted with one or two $R_{11}$ groups, as defined below, which are identical or different;
group $Z_5$ is chosen from
1) a nitrogen atom and
2) a carbon atom, optionally substituted with an $R_{11}$ group, as defined below;

two of the adjacent groups $Z_1$, $Z_2$, $Z_3$, $Z_4$ and $Z_5$ may optionally form a 5- to 7-membered ring, wherein each member is chosen from
1) an oxygen atom and a sulfur atom,
2) a nitrogen atom, optionally substituted with an $R_{11}$ group, as defined below, and
3) a carbon atom, optionally substituted with one or two $R_{11}$ groups, as defined below, which are identical or different;

wherein:
said groups $R_{11}$ are chosen from:
a hydrogen atom;
a group Z as defined above;
linear and branched, saturated and unsaturated groups containing from 1 to 10 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the proviso that:
(i) said $R_{11}$ does not comprise a group chosen from a peroxide group, a diazo group, a nitro group, and a nitroso group, $Z_6$ is chosen from said $R_{11}$ groups, provided that $Z_6$ is not a hydrogen atom;

$Z_1$ and $Z_6$, or $Z_5$ and $Z_6$, optionally form a 5- to 7-membered ring chosen from saturated rings and unsaturated rings, wherein said members are each optionally substituted with one or two said radicals $R_{11}$, which are identical or different;

$R_{\dot{e}}$, $R_8$, $R_9$, and $R_{10}$, which are identical or different, are each chosen from said groups $R_{11}$;

groups $R_{\dot{e}}$, $R_8$, and $R_9$ optionally form, in pairs with the quaternary nitrogen atom to which they are attached, at least one 5- to 7-membered saturated ring, wherein said members are each chosen from
1) an oxygen atom and a sulfur atom,
2) a nitrogen atom, optionally substituted with a said $R_{11}$ group, and
3) a carbon atom, optionally substituted with one or two said $R_{11}$ groups, which are identical or different;

$X^-$ is chosen from organic anions and inorganic anions;

said groups B are linked to said groups D by any one of the atoms of said group D;

n and p, independently of each other, are equal to 0 or 1;

when n=0, then said group $R_{10}$ is optionally a direct bond, wherein said cationic group of formula (IV) is linked directly to said compound of formula (I) by way of the nitrogen cation of said cationic group of (IV);

$R_2$ is chosen from:
(1) a hydrogen atom;
(2) a group Z as defined above;
(3) linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
(i) said $R_2$ does not comprise a group chosen from a peroxide group, a diazo group, a nitro group, and a nitroso group; and
(ii) $R_2$ is not a hydroxyl or a thio group;

said $R_1$ and said $R_2$, together with the atoms to which they are attached, optionally form a 5- to 7-membered ring chosen from saturated rings and unsaturated rings, wherein said members are each chosen from a carbon atom, a nitrogen atom, an oxygen atom, a sulfur atom, and a carbonyl group, and said members are optionally substituted with 1 or 2 groups R, wherein R is chosen from linear and branched, saturated and unsaturated, $C_1$–$C_6$ alkyl groups, optionally substituted with at least one halogen atom, wherein at least one carbon atom is optionally and independently replaced by an oxygen atom, a nitrogen atom, a sulfur atom, or an $SO_2$ group, and at least one branch of said branched $C_1$–$C_6$ alkyl group optionally forms at least one ring chosen from saturated and unsaturated 3- to 6-membered rings; with the proviso that:
(i) said R does not comprise a group chosen from a peroxide group, a diazo group, a nitro group, and a nitroso group;

$R_3$ is chosen from:
a hydrogen atom and halogen atoms;
a group Z as defined above;
linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally form at least one 3- to 7-membered ring comprising at least one carbon atom, with the provisos that:
(i) said $R_3$ does not comprise a group chosen from a peroxide group, a diazo group, a nitro group, and a nitroso group;
(ii) said $R_3$ is not a hydroxyl group; and
(iii) said $R_3$ is not directly linked to the benzene ring of formula (I) by an —NH—NH— group;

$R_4$ is chosen from:
(1) a hydrogen atom and a chlorine atom;
(2) said group Z;
(3) a group chosen from methyl, ethyl, hydroxymethyl, methoxymethyl, aminomethyl, methylaminomethyl, hydroxyl, methoxy, acetoxy, amino, methylamino, N-piperidino and N-morpholino;
(4) a group —NH(CO)$R_{15}$ wherein $R_{15}$ is chosen from group (G1) chosen from methyl, ethyl, propyl, isopropyl, butyl, isobutyl, tert-butyl, pentyl, isopentyl, neopentyl, hexyl; cyclopropyl, cyclobutyl, cyclopentyl, cyclopentylmethyl, 3-cyclopentylpropyl, cyclohexyl, 2-cyclohexylethyl, norborn-2-yl, vinyl, 1-methylvinyl, 2-methylvinyl, 2,2-dimethylvinyl, allyl, 3-butenyl, phenyl, methylphenyl, dimethylphenyl, 2,4,6-trimethylphenyl, 4-ethylphenyl, (trifluoromethyl) phenyl, hydroxyphenyl, methoxyphenyl, ethoxyphenyl, acetoxyphenyl, (trifluoromethoxy) phenyl, aminophenyl, 4-dimethylaminophenyl, fluorophenyl, difluorophenyl, fluoro (trifluoromethyl)phenyl, chlorophenyl, dichlorophenyl, bromophenyl, naphth-1-yl, naphth-2-yl, (2-methoxy)naphth-1-yl, benzyl, 4'-methoxybenzyl, 2',5'-dimethoxybenzyl, 3',4'-dimethoxybenzyl, 4'-fluorobenzyl, 4'-chlorobenzyl, phenethyl, 2-phenylvinyl, (1-naphthyl)methyl, (2-naphthyl)methyl; tetrahydrofuran-2-yl, furan-2-yl, 5-methyl-2-(trifluoromethyl)furan-3-yl, 2-methyl-5-phenylfuran-3-yl, thiophen-2-yl, (thiophen-2-yl)methyl, 3-chlorothiophen-2-yl, 2,5-dichlorothiophen-3-yl, benzothiophen-2-yl, 3-chlorobenzothiophen-2-yl, isoxazol-5-yl, 5-methylisoxazol-3-yl, 3,5-dimethylisoxazol-4-yl, 1,3-dimethylpyrazol-5-yl, 1-ethyl-3-methylpyrazol-5-yl, 1-tert-butyl-3-methylpyrazol-5-yl, 3-tert-butyl-1-methylpyrazol-5-yl, 4-bromo-1-ethyl-3-methylpyrazol-5-yl, indol-3-ylcarboxyl, pyridinyl, chloropyridinyl, dichloropyridinyl, 5-(bromo)pyridin-3-yl, piperazin-2-yl, quinoxal-2-yl, fluoromethyl, difluoromethyl, trifluoromethyl, 1,1,2,2-tetrafluoro-ethyl, pentafluoroethyl, heptafluoropropyl, 1,1,2,2,3,3,4,4-octafluorobutyl, nonafluorobutyl, chloromethyl, chloroethyl, 1,1-dimethyl-2-chloroethyl, 1,2-dichloroethyl, 1-chloropropyl, 3-chloropropyl, 4-chlorobutyl, hydroxymethyl, methoxymethyl, phenoxymethyl, (4-chlorophenoxy)methyl, benzyloxymethyl, acetoxymethyl, 1,2-dihydroxyethyl, 1-phenoxyethyl, 1-acetoxyethyl, 2-(2-carboxyethoxy)ethyl, 1-phenoxyethyl, 1-acetoxyethyl, methoxycarbonyl, ethoxycarbonyl, (methoxycarbonyl)methyl, 2-carboxyethyl, 2-(methoxycarbonyl)ethyl, 2-carboxycyclopropyl, 2-carboxycyclohexane; methoxy, ethoxy, propoxy, isopropoxy, butoxy, isobutoxy, pentoxy, neopentoxy, hexyloxy, cyclopentyloxy, cyclohexyloxy, vinyloxy, allyloxy, propargyloxy, chloromethoxy, 1-chloroethoxy, 2-methoxyethoxy, 4-chlorobutoxy, phenoxy, 4-methylphenoxy, 4-fluorophenoxy, 4-bromophenoxy, 4-chlorophenoxy, 4-methoxyphenoxy, naphth-2-yloxy, benzyloxy; amino, methylamino, ethylamino, propylamino, isopropylamino, butylamino, cyclohexylamino, allylamino, 2-chloroethylamino, 3-chloropropylamino, carboxymethylamino, phenylamino, fluorophenylamino, (trifluoromethyl)phenylamino, chlorophenylamino, bromophenylamino, 4-acetylphenylamino, methoxyphenylamino, (trifluoromethoxy)phenylamino, naphth-1-ylamino, benzylamino, phenethylamino, pyrid-3-ylamino, dimethylamino, 1-pyrrolidinyl and 4-morpholinyl; and (5) a group —NHSO$_2$R$_{16}$ in which R$_{16}$ is chosen from group (G3) chosen from methyl, trifluoromethyl, ethyl, 2-chloroethyl, propyl, 3-chloropropyl, isopropyl, butyl, thiophen-2-yl, hydroxyl, ethoxy and dimethylamino;

R$_5$ is chosen from:
 a hydrogen atom and halogen atoms;
 a group Z as defined above;
 linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an SO$_2$ group, and at least one branch of said branched groups optionally forms at least one 3- to 7-membered ring comprising at least one carbon atom, with the provisos that:

(i) said R$_5$ does not comprise a group chosen from a peroxide group, a diazo group, a nitro group, and a nitroso group;
(ii) said R$_5$ is chosen from a group other than a hydroxyl group, a thio group, an amino group, and an optionally substituted sulphonylamino group; and
(iii) said R$_5$ is not directly linked to the benzene ring of formula (I) by a —NH—NH— group;

said R$_1$ and said R$_3$, together with the atoms to which they are attached, optionally form a 6- to 7-membered saturated ring, wherein said members are each chosen from a carbon atom, a nitrogen atom, an oxygen atom, a sulfur atom, and a carbonyl group, and said members are optionally substituted with 1 or 2 said groups R as defined above, with the proviso that:
(i) said R does not comprise a group chosen from a peroxide group, a diazo group, a nitro group, and a nitroso group; and said R$_2$ and said R$_3$, together with the atoms to which they are attached, optionally form a 5- to 7-membered saturated ring, wherein said members are each chosen from a carbon atom, a nitrogen atom, an oxygen atom, a sulfur atom, and a carbonyl group, and said members are optionally substituted with 1 or 2 said groups R as defined above, with the proviso that:
(i) said R does not comprise a group chosen from a peroxide group, a diazo group, a nitro group, and a nitroso group;
(ii) when said R$_2$ and said R$_3$ form a 5- to 7-membered saturated ring, said R$_3$ optionally is a bond;

Y is chosen from:
 a hydrogen atom and halogen atoms;
 groups —OR$_6$, —SR$_6$ and —NH—SO$_2$R$_6$, wherein
  R$_6$ is chosen from linear and branched C$_1$–C$_6$ alkyl groups, optionally substituted with at least one group chosen from a halogen atom, a hydroxyl group, C$_1$–C$_4$ alkoxy groups, an amino group, amino(C$_1$–C$_4$ alkyl) groups, wherein at least one branch of said R$_6$ optionally forms at least one 3- to 6-membered ring;
 a phenyl group, optionally substituted with one or two groups chosen from C$_1$–C$_4$ alkyl groups, a trifluoromethyl group, a carboxyl group, C$_1$–C$_4$ alkoxycarbonyl groups, a halogen atom, a hydroxyl group, C$_1$–C$_4$ alkoxy groups, an amino group and amino (C$_1$–C$_4$ alkyl) groups; and
 a benzyl group, optionally substituted with one or two oxy groups.

17. A composition for oxidation dyeing keratinous fibers comprising, in a medium suitable for dyeing:
(a) at least one oxidation base; and
(b) at least one coupler chosen from compounds of formula (I) and acid addition salts of any of the foregoing compounds:

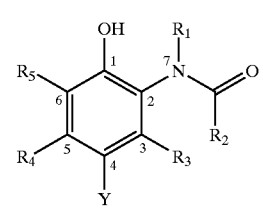

(I)

wherein:
at least one of $R_1$, $R_2$, $R_3$, $R_4$, and $R_5$, as defined below, is chosen from a cationic group, as defined below;

$R_1$ is chosen from:
(1) a hydrogen atom;
(2) linear and branched, saturated and unsaturated groups containing from 1–15 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
(i) said $R_1$ does not comprise a group chosen from a peroxide group, a diazo group, a nitro group, and a nitroso group, and
(ii) said $SO_2$ group is not directly linked to the nitrogen atom at the 7-position of formula (I);
(3) a group Z chosen from cationic groups of formula (II);

$$—[(B)_n—D]\quad\text{(II)}$$

wherein:
groups B are chosen from linear and branched, saturated and unsaturated groups containing from 1–15 carbon atoms, optionally substituted with at least one substituent chosen from a halogen atom and a group Z, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the proviso that:
(i) said B does not comprise a group chosen from a peroxide group, a diazo group, a nitro group, and a nitroso group; and
groups D are chosen from cationic groups of formulae (III) and (IV):

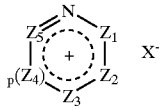
(III)

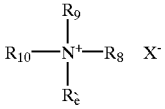
(IV)

wherein:
group $Z_1$, group $Z_2$, group $Z_3$, and group $Z_4$, which are identical or different, are each chosen from
1) an oxygen atom and a sulfur atom,
2) a nitrogen atom, optionally substituted with an $R_{11}$ group, as defined below, and
3) a carbon atom, optionally substituted with one or two $R_{11}$ groups, as defined below, which are identical or different;
group $Z_5$ is chosen from
1) a nitrogen atom and
2) a carbon atom, optionally substituted with an $R_{11}$ group, as defined below;

two of the adjacent groups $Z_1$, $Z_2$, $Z_3$, $Z_4$ and $Z_5$ may optionally form a 5 to 7-membered wherein member is chosen from
1) an oxygen atom and a sulfur atom,
2) a nitrogen atom, optionally substituted with an $R_{11}$ group, as defined below, and
3) a carbon atom, optionally substituted with one or two $R_{11}$ groups, as defined below, which are identical or different;
wherein:
said groups $R_{11}$ are chosen from:
a hydrogen atom;
a group Z as defined above;
linear and branched, saturated and unsaturated groups containing from 1 to 10 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the proviso that:
(i) said $R_{11}$ does not comprise a group chosen from a peroxide group, a diazo group, a nitro group, and a nitroso group,
$Z_6$ is chosen from said $R_{11}$ groups, provided that $Z_6$ is not a hydrogen atom;
$Z_1$ and $Z_6$, or $Z_5$ and $Z_6$, optionally form a 5- to 7-membered ring chosen from saturated rings and unsaturated rings, wherein said members are each optionally substituted with one or two said radicals $R_{11}$, which are identical or different;
$R_{\dot e}$, $R_8$, $R_9$, and $R_{10}$, which are identical or different, are each chosen from said groups $R_{11}$;
groups $R_{\dot e}$, $R_8$, and $R_9$ optionally form, in pairs with the quaternary nitrogen atom to which they are attached, at least one 5- to 7-membered saturated ring, wherein said members are each chosen from
1) an oxygen atom and a sulfur atom,
2) a nitrogen atom, optionally substituted with a said $R_{11}$ group, and
3) a carbon atom, optionally substituted with one or two said $R_{11}$ groups, which are identical or different;
$X^-$ is chosen from organic anions and inorganic anions;
said groups B are linked to said groups D by any one of the atoms of said group D;
n and p, independently of each other, are equal to 0 or 1;
when n=0, then said group $R_{10}$ is optionally a direct bond, wherein said cationic group of formula (IV) is linked directly to said compound of formula (I) by way of the nitrogen cation of said cationic group of formula (IV);

$R_2$ is chosen from:
(1) a hydrogen atom;
(2) a group Z as defined above;
(3) linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
  (i) said $R_2$ does not comprise a group chosen from a peroxide group, a diazo group, a nitro group, and a nitroso group; and
  (ii) $R_2$ is not a hydroxyl or a thio group;

said $R_1$ and said $R_2$, together with the atoms to which they are attached, optionally form a 5- to 7-membered ring chosen from saturated rings and unsaturated rings, wherein said members are each chosen from a carbon atom, a nitrogen atom, an oxygen atom, a sulfur atom, and a carbonyl group, and said members are optionally substituted with 1 or 2 groups R, wherein R is chosen from linear and branched, saturated and unsaturated, $C_1$–$C_6$ alkyl groups, optionally substituted with at least one halogen atom, wherein at least one carbon atom is optionally and independently replaced by an oxygen atom, a nitrogen atom, a sulfur atom, or an $SO_2$ group, and at least one branch of said branched $C_1$–$C_6$ alkyl group optionally forms at least one ring chosen from saturated and unsaturated 3- to 6-membered rings; with the proviso that:
  (i) said R does not comprise a group chosen from a peroxide group, a diazo group, a nitro group, and a nitroso group;

$R_3$ is chosen from:
  a hydrogen atom and halogen atoms;
  a group Z as defined above;
  linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally form at least one 3- to 7-membered ring comprising at least one carbon atom, with the provisos that:
    (i) said $R_3$ does not comprise a group chosen from a peroxide group, a diazo group, a nitro group, and a nitroso group;
    (ii) said $R_3$ is not a hydroxyl group; and
    (iii) said $R_3$ is not directly linked to the benzene ring of formula (I) by an —NH—NH— group;

$R_4$ is chosen from:
  (1) a hydrogen atom and a chlorine atom;
  (2) a group chosen from methyl, hydroxymethyl, aminomethyl, hydroxyl, methoxy, amino, methylamino, methanesulfonylamino, ethanesulfonylamino, and dimethylaminosulfonylamino; a group —NH(CO)$R_{17}$ wherein $R_{17}$ is chosen from a group (G2) chosen from methyl, ethyl, propyl, allyl, phenyl, tetrahydrofuran-2-yl, furan-2-yl, thiophen-2-yl, pyridinyl, piperazin-2-yl, fluoromethyl, chloromethyl, 2-chloroethyl, methoxymethyl, acetoxymethyl, 1,2-dihydroxyethyl, methoxycarbonyl, 2-carboxyethyl, methoxy, ethoxy, propoxy, allyloxy, 2-chloroethoxy, 2-methoxyethoxy, amino, ethylamino, allylamino, 2-chloroethylamino, pyridylamino, dimethylamino, 1-pyrrolidinyl and 4-morpholinyl, and
  (3) a group —O—E—$D_3$, —NH—E—$D_3$, —$CH_2$O—E—$D_3$, —$CH_2$NH—E—$D_3$, —$CH_2$NH(CO)—$D_3$, —NH(CO)—$D_3$, —NH(CO)—E—$D_3$, —NH(CO)O—E—$D_3$, —NH(CO)NH—E—$D_3$ or —NH($SO_2$)—E—$D_3$, wherein —E— is a —$(CH_2)_q$— group, q is an integer equal to 1 or 2, and $D_3$ is a group D' chosen from 3-methylimidazolidinium-1-yl, 3-(2-hydroxyethyl)imidazolidinium-1-yl, 1,2,4-triazolinium-1-yl, 1,2,4-triazolinium-4-yl, N—($C_1$–$C_4$)alkylpyridinium-2-yl, N—($C_1$–$C_4$) alkylpyridinium-3-yl, N—($C_1$–$C_4$)alkylpyridinium-4-yl, N-(2-hydroxyethyl)pyridinium-2-yl, N-(2-hydroxyethyl)pyridinium-3-yl, N-(2-hydroxyethyl) pyridinium-4-yl, pyridinium-1-yl, tri($C_1$–$C_4$) alkylammonium-N-yl, 1-methylpiperidinium-1-yl and 1,4-dimethylpiperazinium-1-yl;

$R_5$ is chosen from:
  a hydrogen atom and halogen atoms;
  a group Z as defined above;
  linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
    (i) said $R_5$ does not comprise a group chosen from a peroxide group, a diazo group, a nitro group, and a nitroso group;
    (ii) said $R_5$ is chosen from a group other than a hydroxyl group, a thio group, an amino group, and an optionally substituted sulphonylamino group; and
    (iii) said $R_5$ is not directly linked to the benzene ring of formula (I) by a —NH—NH— group;

said $R_1$ and said $R_3$, together with the atoms to which they are attached, optionally form a 6- to 7-membered saturated ring, wherein said members are each chosen from a carbon atom, a nitrogen atom, an oxygen atom, a sulfur atom, and a carbonyl group, and said members are optionally substituted with 1 or 2 said groups R as defined above, with the proviso that:
  (i) said R does not comprise a group chosen from a peroxide group, a diazo group, a nitro group, and a nitroso group; and said $R_2$ and said $R_3$, together with the atoms to which they are attached, optionally form a 5- to 7-membered saturated ring, wherein said members are each chosen from a carbon atom, a nitrogen atom, an oxygen atom, a sulfur atom, and a carbonyl group, and said members are optionally substituted with 1 or 2 said groups R as defined above, with the proviso that:
  (i) said R does not comprise a group chosen from a peroxide group, a diazo group, a nitro group, and a nitroso group;
  (ii) when said $R_2$ and said $R_3$ form a 5- to 7-membered saturated ring, said $R_3$ optionally is a bond;

Y is chosen from:
  a hydrogen atom and halogen atoms;
  groups —$OR_6$, —$SR_6$ and —NH—$SO_2R_6$, wherein
    $R_6$ is chosen from linear and branched $C_1$–$C_6$ alkyl groups, optionally substituted with at least one group chosen from a halogen atom, a hydroxyl group, $C_1$–$C_4$ alkoxy groups, an amino group, amino($C_1$–$C_4$ alkyl) groups, wherein at least one branch of said $R_6$ optionally forms at least one 3- to 6-membered ring;
  a phenyl group, optionally substituted with one or two groups chosen from $C_1$–$C_4$ alkyl groups, a trifluoromethyl group, a carboxyl group, $C_1$–$C_4$ alkoxycarbonyl groups, a halogen atom, a hydroxyl group, $C_1$–$C_4$ alkoxy groups, an amino group and amino ($C_1$–$C_4$ alkyl) groups; and a benzyl group, optionally substituted with one or two oxy groups.

18. A composition for oxidation dyeing keratinous fibers comprising, in a medium suitable for dyeing:
(a) at least one oxidation base; and
(b) at least one coupler chosen from compounds of formula (I) and acid addition salts of any of the foregoing compounds:

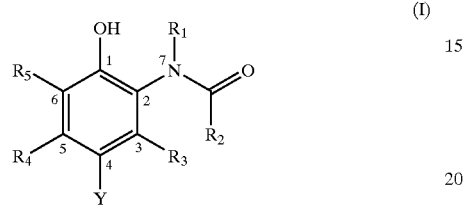

wherein:
at least one of $R_1$, $R_2$, $R_3$, $R_4$, and $R_5$, as defined below, is chosen from a group Z, as defined below;
$R_1$ is chosen from:
(1) a hydrogen atom;
(2) linear and branched, saturated and unsaturated groups containing from 1–15 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
(i) said $R_1$ does not comprise a group chosen from a peroxide group, a diazo group, a nitro group, and a nitroso group, and
(ii) said $SO_2$ group is not directly linked to the nitrogen atom at the 7-position of formula (I);
(3) a group Z chosen from cationic groups of formula (II);

wherein:
groups B are chosen from linear and branched, saturated and unsaturated groups containing from 1–15 carbon atoms, optionally substituted with at least one substituent chosen from a halogen atom and a group Z, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the proviso that:
(i) said B does not comprise a group chosen from a peroxide group, a diazo group, a nitro group, and a nitroso group; and
groups D are chosen from cationic groups of formulae (III) and (IV):

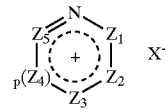

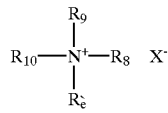

wherein:
group $Z_1$, group $Z_2$, group $Z_3$, and group $Z_4$, which are identical or different, are each chosen from
1) an oxygen atom and a sulfur atom,
2) a nitrogen atom, optionally substituted with an $R_{11}$ group, as defined below, and
3) a carbon atom, optionally substituted with one or two $R_{11}$ groups, as defined below, which are identical or different;
group $Z_5$ is chosen from
1) a nitrogen atom and
2) a carbon atom, optionally substituted with an $R_{11}$ group, as defined below;
two of the adjacent groups $Z_1$, $Z_2$, $Z_3$, $Z_4$ and $Z_5$ may optionally form a 5- to 7-membered ring, wherein each member is chosen from
1) an oxygen atom and a sulfur atom,
2) a nitrogen atom, optionally substituted with an $R_{11}$ group, as defined below, and
3) a carbon atom, optionally substituted with one or two $R_{11}$ groups, as defined below, which are identical or different;
wherein:
said groups $R_{11}$ are chosen from:
a hydrogen atom;
a group Z as defined above;
linear and branched, saturated and unsaturated groups containing from 1 to 10 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the proviso that:
(i) said $R_{11}$ does not comprise a group chosen from a peroxide group, a diazo group, a nitro group, and a nitroso group,
$Z_6$ is chosen from said $R_{11}$ groups, provided that $Z_6$ is not a hydrogen atom;
$Z_1$ and $Z_6$, or $Z_5$ and $Z_6$, optionally form a 5- to 7-membered ring chosen from saturated rings and unsaturated rings, wherein said members are each optionally substituted with one or two said radicals $R_{11}$, which are identical or different;
$R_{\dot{8}}$, $R_8$, $R_9$, and $R_{10}$, which are identical or different, are each chosen from said groups $R_{11}$;
groups $R_{\dot{8}}$, $R_8$, and $R_9$ optionally form, in pairs with the quaternary nitrogen atom to which they are attached, at least one 5- to 7-membered saturated ring, wherein said members are each chosen from 1) an oxygen atom and a sulfur atom,
2) a nitrogen atom, optionally substituted with a said $R_{11}$ group, and
3) a carbon atom, optionally substituted with one or two said $R_{11}$ groups, which are identical or different;

$X^-$ is chosen from organic anions and inorganic anions;

said groups B are linked to said groups D by any one of the atoms of said group D;

n and p, independently of each other, are equal to 0 or 1;

when n=0, then said group Rio is optionally a direct bond, wherein said cationic group of formula (IV) is linked directly to said compound of formula (I) by way of the nitrogen cation of said cationic group of formula (IV);

$R_2$ is chosen from:
(1) a hydrogen atom;
(2) a group Z as defined above;
(3) linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
  (i) said $R_2$ does not comprise a group chosen from a peroxide group, a diazo group, a nitro group, and a nitroso group; and
  (ii) $R_2$ is not a hydroxyl or a thio group;

said $R_1$ and said $R_2$, together with the atoms to which they are attached, optionally form a 5- to 7-membered ring chosen from saturated rings and unsaturated rings, wherein said members are each chosen from a carbon atom, a nitrogen atom, an oxygen atom, a sulfur atom, and a carbonyl group, and said members are optionally substituted with 1 or 2 groups R, wherein
  R is chosen from linear and branched, saturated and unsaturated, $C_1$–$C_6$ alkyl groups, optionally substituted with at least one halogen atom, wherein at least one carbon atom is optionally and independently replaced by an oxygen atom, a nitrogen atom, a sulfur atom, or an $SO_2$ group, and at least one branch of said branched $C_{1-6}$ alkyl group optionally forms at least one ring chosen from saturated and unsaturated 3- to 6-membered rings; with the proviso that:
    (i) said R does not comprise a group chosen from a peroxide group, a diazo group, a nitro group, and a nitroso group;

$R_3$ and $R_4$, which are identical or different, are each chosen from:
  a hydrogen atom and halogen atoms;
  a group Z as defined above;
  linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally form at least one 3- to 7-membered ring comprising at least one carbon atom, with the provisos that:
    (i) said $R_3$ and said $R_4$ do not comprise a group chosen from a peroxide group, a diazo group, a nitro group, and a nitroso group;
    (ii) said $R_3$ and said $R_4$ are not a hydroxyl group; and
    (iii) said $R_3$ and said $R_4$ are not directly linked to the benzene ring of formula (I) by an —NH—NH— group;

$R_5$ is chosen from:
(1) a hydrogen atom, a chlorine atom, a fluorine atom, and a bromine atom;
(2) said group Z;
(3) a group chosen from methyl, trifluoromethyl, allyl, hydroxymethyl, methoxymethyl, 1-hydroxyethyl, aminomethyl, methylaminomethyl, methoxy, acetoxy and methylamino groups; and a group —NH(CO)$R_{18}$ in which $R_{18}$ is a group (G1) chosen from methyl, ethyl, propyl, isopropyl, butyl, isobutyl, tert-butyl, pentyl, isopentyl, neopentyl, hexyl; cyclopropyl, cyclobutyl, cyclopentyl, cyclopentylmethyl, 3-cyclopentylpropyl, cyclohexyl, 2-cyclohexylethyl, norborn-2-yl, vinyl, 1-methylvinyl, 2-methylvinyl, 2,2-dimethylvinyl, allyl, 3-butenyl, phenyl, methylphenyl, dimethylphenyl, 2,4,6-trimethylphenyl, 4-ethylphenyl, (trifluoromethyl)phenyl, hydroxyphenyl, methoxyphenyl, ethoxyphenyl, acetoxyphenyl, (trifluoromethoxy)phenyl, aminophenyl, 4-dimethylaminophenyl, fluorophenyl, difluorophenyl, fluoro(trifluoromethyl)phenyl, chlorophenyl, dichlorophenyl, bromophenyl, naphth-1-yl, naphth-2-yl, (2-methoxy)naphth-1-yl, benzyl, 4'-methoxybenzyl, 2',5'-dimethoxybenzyl, 3',4'-dimethoxybenzyl, 4'-fluorobenzyl, 4'-chlorobenzyl, phenethyl, 2-phenylvinyl, (1-naphthyl)methyl, (2-naphthyl)methyl; tetrahydrofuran-2-yl, furan-2-yl, 5-methyl-2-(trifluoromethyl)furan-3-yl, 2-methyl-5-phenylfuran-3-yl, thiophen-2-yl, (thiophen-2-yl)methyl, 3-chlorothiophen-2-yl, 2,5-dichlorothiophen-3-yl, benzothiophen-2-yl, 3-chlorobenzothiophen-2-yl, isoxazol-5-yl, 5-methylisoxazol-3-yl, 3,5-dimethylisoxazol-4-yl, 1,3-dimethylpyrazol-5-yl, 1-ethyl-3-methylpyrazol-5-yl, 1-tert-butyl-3-methylpyrazol-5-yl, 3-tert-butyl-1-methylpyrazol-5-yl, 4-bromo-1-ethyl-3-methylpyrazol-5-yl, indol-3-ylcarboxyl, pyridinyl, chloropyridinyl, dichloropyridinyl, 5-(bromo)pyridin-3-yl, piperazin-2-yl, quinoxal-2-yl, fluoromethyl, difluoromethyl, trifluoromethyl, 1,1,2,2-tetrafluoroethyl, pentafluoroethyl, heptafluoropropyl, 1,1,2,2,3,3,4,4-octafluorobutyl, nonafluorobutyl, chloromethyl, chloroethyl, 1,1-dimethyl-2-chloroethyl, 1,2-dichloroethyl, 1-chloropropyl, 3-chloropropyl, 4-chlorobutyl, hydroxymethyl, methoxymethyl, phenoxymethyl, (4-chlorophenoxy)methyl, benzyloxymethyl, acetoxymethyl, 1,2-dihydroxyethyl, 1-phenoxyethyl, 1-acetoxyethyl, 2-(2-carboxyethoxy)ethyl, 1-phenoxyethyl, 1-acetoxyethyl, methoxycarbonyl, ethoxycarbonyl, (methoxycarbonyl)methyl, 2-carboxyethyl, 2-(methoxycarbonyl)ethyl, 2-carboxycyclopropyl, 2-carboxycyclohexane; methoxy, ethoxy, propoxy, isopropoxy, butoxy, isobutoxy, pentoxy, neopentoxy, hexyloxy, cyclopentyloxy, cyclohexyloxy, vinyloxy, allyloxy, propargyloxy, chloromethoxy, 1-chloroethoxy, 2-methoxyethoxy, 4-chlorobutoxy, phenoxy, 4-methylphenoxy, 4-fluorophenoxy, 4-bromophenoxy, 4-chlorophenoxy, 4-methoxyphenoxy, naphth-2-yloxy, benzyloxy; amino, methylamino, ethylamino, propylamino, isopropylamino, butylamino, cyclohexylamino, allylamino, 2-chloroethylamino, 3-chloropropylamino, carboxymethylamino, phenylamino, fluorophenylamino, (trifluoromethyl)phenylamino, chlorophenylamino, bromophenylamino, 4-acetylphenylamino, methoxyphenylamino, (trifluoromethoxy)phenylamino, naphth-1-ylamino, benzylamino, phenethylamino, pyrid-3-ylamino, dimethylamino, 1-pyrrolidinyl and 4-morpholinyl;

said $R_1$ and said $R_3$, together with the atoms to which they are attached, optionally form a 6- to 7-membered saturated ring, wherein said members are each chosen from a carbon atom, a nitrogen atom, an oxygen atom, a sulfur atom, and a carbonyl group, and said members are optionally substituted with 1 or 2 said groups R as defined above, with the proviso that:
 (i) said R does not comprise a group chosen from a peroxide group, a diazo group, a nitro group, and a nitroso group; and said $R_2$ and said $R_3$, together with the atoms to which they are attached, optionally form a 5- to 7-membered saturated ring, wherein said members are each chosen from a carbon atom, a nitrogen atom, an oxygen atom, a sulfur atom, and a carbonyl group, and said members are optionally substituted with 1 or 2 said groups R as defined above, with the proviso that:
 (i) said R does not comprise a group chosen from a peroxide group, a diazo group, a nitro group, and a nitroso group;
 (ii) when said $R_2$ and said $R_3$ form a 5- to 7-membered saturated ring, said $R_3$ optionally is a bond;

Y is chosen from:
 a hydrogen atom and halogen atoms;
 groups —$OR_6$, —$SR_6$ and —NH—$SO_2R_6$, wherein
  $R_6$ is chosen from linear and branched $C_1$–$C_6$ alkyl groups, optionally substituted with at least one group chosen from a halogen atom, a hydroxyl group, $C_1$–$C_4$ alkoxy groups, an amino group, amino($C_1$–$C_4$ alkyl) groups, wherein at least one branch of said $R_6$ optionally forms at least one 3- to 6-membered ring;
 a phenyl group, optionally substituted with one or two groups chosen from $C_1$–$C_4$ alkyl groups, a trifluoromethyl group, a carboxyl group, $C_1$–$C_4$ alkoxycarbonyl groups, a halogen atom, a hydroxyl group, $C_1$–$C_4$ alkoxy groups, an amino group and amino($C_1$–$C_4$ alkyl) groups; and
 a benzyl group, optionally substituted with one or two oxy groups.

19. A composition for oxidation dyeing keratinous fibers comprising, in a medium suitable for dyeing:
(a) at least one oxidation base; and
(b) at least one coupler chosen from compounds of formula (I) and acid addition salts of any of the foregoing compounds:

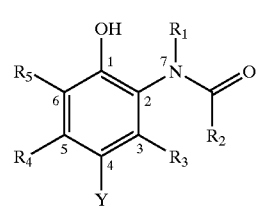

wherein:
 at least one of $R_1$, $R_2$, $R_3$, $R_4$, and $R_5$, as defined below, is chosen from a cationic group, as defined below;
 $R_1$ is chosen from:
  (1) a hydrogen atom;
  (2) linear and branched, saturated and unsaturated groups containing from 1–15 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
   (i) said $R_1$ does not comprise a group chosen from a peroxide group, a diazo group, a nitro group, and a nitroso group, and
   (ii) said $SO_2$ group is not directly linked to the nitrogen atom at the 7-position of formula (I);
  (3) a group Z chosen from cationic groups of formula (II);

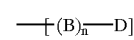

wherein:
 groups B are chosen from linear and branched, saturated and unsaturated groups containing from 1–15 carbon atoms, optionally substituted with at least one substituent chosen from a halogen atom and a group Z, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the proviso that:
  (i) said B does not comprise a group chosen from a peroxide group, a diazo group, a nitro group, and a nitroso group; and
 groups D are chosen from cationic groups of formulae (III) and (IV):

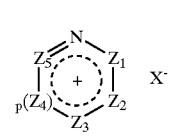

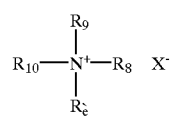

wherein:
group $Z_1$, group $Z_2$, group $Z_3$, and group $Z_4$, which are identical or different, are each chosen from
  1) an oxygen atom and a sulfur atom,
  2) a nitrogen atom, optionally substituted with an $R_{11}$ group, as defined below, and
  3) a carbon atom, optionally substituted with one or two $R_{11}$ groups, as defined below, which are identical or different;
group $Z_5$ is chosen from
  1) a nitrogen atom and
  2) a carbon atom, optionally substituted with an $R_{11}$ group, as defined below;
two of the adjacent groups $Z_1$, $Z_2$, $Z_3$, $Z_4$ and $Z_5$ may optionally form a 5- to 7-membered ring, wherein each member is chosen from
  1) an oxygen atom and a sulfur atom,
  2) a nitrogen atom, optionally substituted with an $R_{11}$ group, as defined below, and
  3) a carbon atom, optionally substituted with one or two $R_{11}$ groups, as defined below, which are identical or different;
wherein:
said groups $R_{11}$ are chosen from:
  a hydrogen atom;
  a group Z as defined above;
  linear and branched, saturated and unsaturated groups containing from 1 to 10 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the proviso that:
(i) said $R_{11}$ does not comprise a group chosen from a peroxide group, a diazo group, a nitro group, and a nitroso group,
  $Z_6$ is chosen from said $R_{11}$ groups, provided that $Z_6$ is not a hydrogen atom;
  $Z_1$ and $Z_6$, or $Z_5$ and $Z_6$, optionally form a 5- to 7-membered ring chosen from saturated rings and unsaturated rings, wherein said members are each optionally substituted with one or two said radicals $R_{11}$, which are identical or different;
$R_7$, $R_8$, $R_9$, and $R_{10}$, which are identical or different, are each chosen from said groups $R_{11}$;
groups $R_7$, $R_8$, and $R_9$ optionally form, in pairs with the quaternary nitrogen atom to which they are attached, at least one 5- to 7-membered saturated ring, wherein said members are each chosen from
  1) an oxygen atom and a sulfur atom,
  2) a nitrogen atom, optionally substituted with a said $R_{11}$ group, and
  3) a carbon atom, optionally substituted with one or two said $R_{11}$ groups, which are identical or different;
$X^-$ is chosen from organic anions and inorganic anions;
said groups B are linked to said groups D by any one of the atoms of said group D;
n and p, independently of each other, are equal to 0 or 1;

when n=0, then said group $R_{10}$ is optionally a direct bond, wherein said cationic group of formula (IV) is linked directly to said compound of formula (I) by way of the nitrogen cation of said cationic group of formula (IV);
$R_2$ is chosen from:
(1) a hydrogen atom;
(2) a group Z as defined above;
(3) linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
(i) said $R_2$ does not comprise a group chosen from a peroxide group, a diazo group, a nitro group, and a nitroso group; and
(ii) $R_2$ is not a hydroxyl or a thio group;
said $R_1$ and said $R_2$, together with the atoms to which they are attached, optionally form a 5- to 7-membered ring chosen from saturated rings and unsaturated rings, wherein said members are each chosen from a carbon atom, a nitrogen atom, an oxygen atom, a sulfur atom, and a carbonyl group, and said members are optionally substituted with 1 or 2 groups R, wherein
R is chosen from linear and branched, saturated and unsaturated, $C_1$–$C_6$ alkyl groups, optionally substituted with at least one halogen atom, wherein at least one carbon atom is optionally and independently replaced by an oxygen atom, a nitrogen atom, a sulfur atom, or an $SO_2$ group, and at least one branch of said branched $C_1$–$C_6$ alkyl group optionally forms at least one ring chosen from saturated and unsaturated 3- to 6-membered rings; with the proviso that:
(i) said R does not comprise a group chosen from a peroxide group, a diazo group, a nitro group, and a nitroso group;
$R_3$ and $R_4$, which are identical or different, are each chosen from:
a hydrogen atom and halogen atoms;
a group Z as defined above;
linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally form at least one 3- to 7-membered ring comprising at least one carbon atom, with the provisos that:
(i) said $R_3$ and said $R_4$ do not comprise a group chosen from a peroxide group, a diazo group, a nitro group, and a nitroso group;
(ii) said $R_3$ and said $R_4$ are not a hydroxyl group; and
(iii) said $R_3$ and said $R_4$ are not directly linked to the benzene ring of formula (I) by an —NH—NH— group;
$R_5$ is chosen from:
(1) a hydrogen atom, a chlorine atom, and a fluorine atom;
(2) a group chosen from methyl, hydroxymethyl, aminomethyl, methoxy and methylamino;
(3) a group —NH(CO)$R_{19}$ in which $R_{19}$ is a group (G2) chosen from methyl, ethyl, propyl, allyl, phenyl, tetrahydrofuran-2-yl, furan-2-yl, thiophen-2-yl, pyridinyl, piperazin-2-yl, fluoromethyl, chloromethyl, 2-chloroethyl, methoxymethyl, acetoxymethyl, 1,2-dihydroxyethyl, methoxycarbonyl, 2-carboxyethyl, methoxy, ethoxy, propoxy, allyloxy, 2-chloroethoxy, 2-methoxyethoxy, amino, ethylamino, allylamino, 2-chloroethylamino, pyridylamino, dimethylamino, 1-pyrrolidinyl and 4-morpholinyl; and (4) a group —O—E—$D_4$, —NH—E—$D_4$, —$CH_2$O—E—$D_4$, —$CH_2$NH—E—$D_4$, —$CH_2$NH(CO)—$D_4$, —NH(CO)—$D_4$, —NH(CO)—E—$D_4$, —NH(CO)O—E—$D_4$, and —NH(CO)NH—E—$D_4$, wherein —E— is a —$(CH_2)_q$— group, q is an integer equal to 1 or 2, and $D_4$ is a group D' chosen from 3-methylimidazolidinium-1-yl, 3-(2-hydroxyethyl)imidazolidinium-1-yl, 1,2,4-triazolinium-1-yl, 1,2,4-triazolinium-4-yl, N—($C_1$–$C_4$)alkypyridinium-2-yl, N—($C_1$–$C_4$)alkylpyridinium-3-yl, N—($C_1$–$C_4$)alkylpyridinium-4-yl, N-(2-hydroxyethyl)pyridinium-2-yl, N-(2-hydroxyethyl)pyridinium-3-yl, N-(2-hydroxyethyl)pyridinium-4-yl, pyridinium-1-yl, tri($C_1$–$C_4$)alkylammonium-N-yl, 1-methylpiperidinium-1-yl and 1,4-dimethylpiperazinium-1-yl;

said $R_1$ and said $R_3$, together with the atoms to which they are attached, optionally form a 6- to 7-membered saturated ring, wherein said members are each chosen from a carbon atom, a nitrogen atom, an oxygen atom, a sulfur atom, and a carbonyl group, and said members are optionally substituted with 1 or 2 said groups R as defined above, with the proviso that:

(i) said R does not comprise a group chosen from a peroxide group, a diazo group, a nitro group, and a nitroso group; and said $R_2$ and said $R_3$, together with the atoms to which they are attached, optionally form a 5- to 7-membered saturated ring, wherein said members are each chosen from a carbon atom, a nitrogen atom, an oxygen atom, a sulfur atom, and a carbonyl group, and said members are optionally substituted with 1 or 2 said groups R as defined above, with the proviso that:

(i) said R does not comprise a group chosen from a peroxide group, a diazo group, a nitro group, and a nitroso group;

(ii) when said $R_2$ and said $R_3$ form a 5- to 7-membered saturated ring, said $R_3$ optionally is a bond;

Y is chosen from:
a hydrogen atom and halogen atoms;
groups —$OR_6$, —$SR_6$ and —NH—$SO_2R_6$, wherein $R_6$ is chosen from linear and branched $C_1$–$C_6$ alkyl groups, optionally substituted with at least one group chosen from a halogen atom, a hydroxyl group, $C_1$–$C_4$ alkoxy groups, an amino group, amino($C_1$–$C_4$ alkyl) groups, wherein at least one branch of said $R_6$ optionally forms at least one 3- to 6-membered ring;
a phenyl group, optionally substituted with one or two groups chosen from $C_1$–$C_4$ alkyl groups, a trifluoromethyl group, a carboxyl group, $C_1$–$C_4$ alkoxycarbonyl groups, a halogen atom, a hydroxyl group, $C_1$–$C_4$ alkoxy groups, an amino group and amino ($C_1$–$C_4$ alkyl) groups; and
a benzyl group, optionally substituted with one or two oxy groups.

20. A composition according to claim 1, wherein Y is a moiety chosen from an atom chosen from a hydrogen atom, a chlorine atom, a fluorine atom, and a bromine atom; and a group chosen from methoxy, ethoxy, propoxy, benzyloxy, phenoxy, —$OCH_2CH_2OCH_3$, —$OCH_2CH_2N(CH_3)_2$, —$OCH_2(CO)OH$, —$OCH_2(CO)OCH_3$, —$OCH_2(CO)OC_2H_5$, —$SCH_2CH_2CO_2H$ and —$NHSO_2CH_3$;
provided that Y is not —$NHSO_2CH_3$ when $R_3$ is a hydroxyl group.

21. A composition according to claim 20, wherein Y is chosen from a hydrogen atom, a chlorine atom, a methoxy group, an —$OCH_2(CO)OH$ group, and an —$OCH_2(CO)OCH_3$ group.

22. A composition according to claim 1 wherein D is a group chosen from imidazolinium, thiazolinium, oxazolinium, pyrrolinium, 1,2,3-triazolinium, 1,2,4-triazoliniurm, isoxazolinium, isothiazolinium, imidazolidinium, thiazolidinium, pyrazolinium, pyrazolidinium, oxazolidinium, pyrazoltriazolinium, pyrazoloimidazolinium, pyrrolotriazolinium, pyrazolopyrimidinium, pyrazolopyridinium, pyridinium, pyrimidinium, pyrazinium, triazinium, benzoimidazolinium, benzoxazolinium, benzothiazolinium, indolinium, indolidinium, isoindolinium, indazolinium, benzotriazolinium, quinolinium, tetrahydroquinolinium, benzoimidazolidinium, benzopyrimidinium, tetra($C_1$–$C_4$)alkylammonium, polyhydroxytetra($C_1$–$C_4$)alkylammonium, dialkylpiperidinium, dialkylpyrrolidinium, dialkylmorpholinium, dialkylthiomorpholinium, dialkylpiperazinium, azepinium and 1,4-diazabicyclo[2.2.2]octanium.

23. A composition according to claim 22, wherein D is a group chosen from 3-methylimidazolidinium-1-yl, 3-(2-hydroxyethyl)imidazolidinium-1-yl, 1,2,4-triazolinium-1-yl, 1,2,4-triazolinium4-yl, N—($C_1$–$C_4$)alkylpyridin-2-yl, N—($C_1$–$C_4$)alkylpyridin-3-yl, N—($C_1$–$C_4$)alkylpyridin-4-yl, N-(2-hydroxyethyl)pyridin-2-yl, N-(2-hydroxyethyl)pyridin-3-yl, N-(2-hydroxyethyl)pyridin-4-yl, pyridin-1-yl, tri($C_1$–$C_4$)alkylammonium-N-yl, 1-methylpiperidinium-1-yl, thiazolinium-3-yl and 1,4-dimethylpiperazinium-1-yl.

24. A composition according to claim 1, wherein said at least one coupler is chosen from Groups (i), (ii), (iii), and (iv) wherein:

(i)
$R_1$ is a hydrogen atom;
$R_2$ is a group Z chosen from —$D_1$, —E—$D_1$, —O—E—$D_1$, and —NH—E—$D_1$, in which —E— is a —$(CH_2)_q$— group, q is equal 1 or 2 and $D_1$ is a group D' chosen from 3-methylimidazolidinium-1-yl, 3-(2-hydroxyethyl)imidazolidinium-1-yl, 1,2,4-triazolinium-1-yl, 1,2,4-triazolinium-4-yl, N—($C_1$–$C_4$)alkylpyridinium-2-yl, N—($C_1$–$C_4$)alkylpyridinium-3-yl, N—($C_1$–$C_4$)alkylpyridinium4-yl, N-(2-hydroxyethyl)pyridinium-2-yl, N-(2-hydroxyethyl)pyridinium-3-yl, N-(2-hydroxyethyl)pyridinium4-yl, pyridinium-1-yl, tri($C_1$–$C_4$)alkylammonium-N-yl, 1-methylpiperidinium-1-yl and 1,4-dimethylpiperazinium-1-yl groups; and $R_2$ is further chosen from a group (G4) chosen from methyl, methoxymethyl, 2-carboxyethyl, methoxy, amino, ethylamino and 1-pyrrolidinyl;
$R_3$ is chosen from a hydroxyl group, an amino group, and a methylamino group; a group —$NH(CO)R_{20}$ in which $R_{20}$ is a group (G4) as defined above; a methanesulfonylamino group, an ethanesulfonylamino group, and a dimethylaminosulfonylamino group; and a group Z chosen from —O—E—$D_2$, —NH—E—$D_2$, and —NH($SO_2$)—E—$D_2$, and groups —NH(CO)—$D_2$, —NH(CO)—E—$D_2$, —NH(CO)O—E—$D_2$, and —NH(CO)

NH—E—$D_2$, wherein E is defined above and $D_2$ is a group chosen from D', also defined above;

$R_4$ is chosen from a hydrogen atom, a chlorine atom, and a methyl group;

$R_5$ is chosen from a hydrogen atom, a chlorine atom, a fluorine atom, and a methyl group; and Y is chosen from a hydrogen atom, a chlorine atom, a methoxy group, and a —$OCH_2(CO)OCH_3$ group; and provided that at least one of said groups $R_2$ and $R_3$ is chosen from a group Z, wherein $R_2$ is chosen from —$D_1$, —E—$D_1$, —O—E—$D_1$, and —NH—E—$D_1$ and $R_3$ is chosen from —O—E—$D_2$, —NH—E—$D_2$, and —NH($SO_2$)—E—$D_2$;

(ii)

$R_1$ is a hydrogen atom;

$R_2$ is a group Z chosen from —$D_1$, —E—$D_1$, —O—E—$D_1$ and —NH—E—$D_1$, as defined above; and a group (G4) as defined above;

$R_3$ is chosen from a hydrogen atom; and a methyl group;

$R_4$ is chosen from a hydroxyl group, an amino group, a methylamino group, a methanesulfonylamino group, an ethanesulfonylamino group, and a dimethylaminosulfonylamino group; groups —NH(CO)$R_{21}$ in which $R_{21}$ is chosen from a group (G4) as defined above; and a group Z chosen from —O—E—$D_3$, —NH—E—$D_3$, and —NH($SO_2$)—E—$D_3$, and groups —NH(CO)—$D_3$, —NH(CO)—E—$D_3$, —NH(CO)O—E—$D_3$, and —NH(CO)NH—E—$D_3$; wherein E is as defined above and $D_3$ is a group chosen from D', also defined above;

$R_5$ is chosen from a hydrogen atom, a chlorine atom, a fluorine atom, a methyl group, a methoxy group, and a methylamino group; and Y is chosen from a hydrogen atom, a chlorine atom, a methoxy group, and a —$OCH_2(CO)OCH_3$ group; and provided that at least one of the groups $R_2$ and $R_4$ is chosen from a group Z, wherein $R_2$ is chosen from —$D_1$, —E—$D_1$, —O—E—$D_1$ and —NH—E—$D_1$ and $R_4$ is chosen from —O—E—$D_3$, —NH—E—$D_3$, and —NH($SO_2$)—E—$D_3$;

(iii)

$R_1$ is a hydrogen atom;

$R_2$ is chosen from a group (G4) defined above; and a group Z chosen from —$D_1$, —E—$D_1$, —O—E—$D_1$, and —NH—E—$D_1$, as defined above;

$R_3$ is chosen from a hydrogen atom, and a methyl group;

$R_4$ is chosen from a hydrogen atom, a chlorine atom, a methyl group, a methoxy group, and a methylamino group;

$R_5$ is chosen from a group —NH(CO)$R_{22}$ in which $R_{22}$ is chosen from groups of group (G4) defined above; and Z groups chosen from —O—E—$D_4$, and —NH—E—$D_4$, and groups —NH(CO)—$D_4$, —NH(CO)—E—$D_4$, —NH(CO)O—E—$D_4$ and —NH(CO)NH—E—$D_4$, wherein E is as defined above and $D_4$ is a group chosen from D', also defined above; and Y is chosen from a hydrogen atom, a chlorine atom, a methoxy group, and a —$OCH_2(CO)OCH_3$group; and provided that at least one of the groups $R_2$ and $R_5$ is chosen from groups Z, wherein $R_2$ is chosen from —$D_1$, —E—$D_1$, —O—E—$D_1$ and —NH—E—$D_1$ and $R_5$ is chosen from —O—E—$D_4$, and —NH—E—$D_4$;

iv)

$R_1$ is chosen from a hydrogen atom;

$R_2$ is a group Z chosen from —$D_1$, —E—$D_1$, —O—E—$D_1$ and —NH—E—$D_1$, as defined above;

$R_3$ is chosen from a hydrogen atom and a methyl group;

$R_4$ is chosen from a hydrogen atom, a chlorine atom, and a methyl group;

$R_5$ is chosen from a hydrogen atom, a chlorine atom, a fluorine atom, and a methyl group; and Y is chosen from a hydrogen atom, a chlorine atom, a methoxy group, and a —$OCH_2(CO)OCH_3$ group.

25. A composition for oxidation dyeing keratinous fibers comprising, in a medium suitable for dyeing:

(a) at least one oxidation base; and (b) at least one coupler chosen from:

3-[(2-Hydroxyphenylcarbamoyl)methyl]-1-methyl-3H-imidazol-1-ium chloride;

3-[(2-Hydroxy-3-(2-(3-methyl-1H-imidazol-3-ium-1-yl)acetylamino)phenylcarbamoyl)methyl]-1-methyl-3H-imidazol-1-ium dichloride;

3-[(2-Hydroxy-4-(2-(3-methyl-1H-imidazol-3-ium-1-yl)acetylamino)phenylcarbamoyl)methyl]-1-methyl-3H-imidazol-1-ium dichloride;

3-[(2-Hydroxy-4-methylphenylcarbamoyl)methyl]-1-methyl-3H-imidazol-1-ium chloride;

3-[(2-Hydroxy-4-aminophenylcarbamoyl)methyl]-1-methyl-3H-imidazol-1-ium chloride;

3-[(2-Hydroxy-4-acetylaminophenylcarbamoyl)methyl]-1-methyl-3H-imidazol-1-ium chloride;

3-[(2-Hydroxy-4-methoxycarbonylaminophenylcarbamoyl)methyl]-1-methyl-3H-imidazol-1-ium chloride;

3-[(3-Hydroxy-4-acetylaminophenylcarbamoyl)methyl]-1-methyl-3H-imidazol-1-ium chloride;

3-[(3-Hydroxy-4-methoxycarbonylaminophenylcarbamoyl)methyl]-1-methyl-3H-imidazol-1-ium chloride;

3-[(2-Hydroxy-5-chlorophenylcarbamoyl)methyl]-1-methyl-3H-imidazol-1-ium chloride;

3-[(2-Hydroxy-4-methyl-5-chlorophenylcarbamoyl)methyl]-1-methyl-3H-imidazol-1-ium chloride;

3-[(2-Hydroxy-4-amino-5-chlorophenylcarbamoyl)methyl]-1-methyl-3H-imidazol-1-ium chloride;

3-[(2-Hydroxy-4-acetylamino-5-chlorophenylcarbamoyl)methyl]-1-methyl-3H-imidazol-1-ium chloride;

3-[(2-Hydroxy-4-methoxycarbonylamino-5-chlorophenylcarbamoyl)methyl]-1-methyl-3H-imidazol-1-ium chloride;

3-[(3-Hydroxy-4-acetylamino-5-chlorophenylcarbamoyl)methyl]-1-methyl-3H-imidazol-1-ium chloride;

3-[(3-Hydroxy-4-methoxycarbonylamino-6-chlorophenylcarbamoyl)methyl]-1-methyl-3H-imidazol-1-ium chloride;

3-[(2-Hydroxy-5-methoxyphenylcarbamoyl)methyl]-1-methyl-3H-imidazol-1-ium chloride;

3-[(2-Hydroxy-4-methyl-5-methoxyphenylcarbamoyl)methyl]-1-methyl-3H-imidazol-1-ium chloride;

3-[(2-Hydroxy-4-amino-5-methoxyphenylcarbamoyl)methyl]-1-methyl-3H-imidazol-1-ium chloride;

3-[(2-Hydroxy-4-acetylamino-5-methoxyphenylcarbamoyl)methyl]-1-methyl-3H-imidazol-1-ium chloride;

3-[(2-Hydroxy-4-methoxycarbonylamino-5-methoxyphenylcarbamoyl)methyl]-1-methyl-3H-imidazol-1-ium chloride;

3-[(3-Hydroxy-4-acetylamino-6-methoxyphenylcarbamoyl)methyl]-1-methyl-3H-imidazol-1-ium chloride;

3-[(3-Hydroxy-4-methoxycarbonylamino-6-methoxyphenylcarbamoyl)methyl]-1-methyl-3H-imidazol-1-ium chloride;

3-[(2-Hydroxy-6-aminophenylcarbamoyl)methyl]-1-methyl-3H-imidazol-1-ium chloride;

3-[(2-Hydroxy-6-acetylaminophenylcarbamoyl)methyl]-1-methyl-3H-imidazol-1-ium chloride;

3-[(2-Hydroxy-4,6-diaminophenylcarbamoyl)methyl]-1-methyl-3H-imidazol-1-ium chloride;
3-[(2-Hydroxy-4-acetylamino-6-aminophenylcarbamoyl)methyl]-1-methyl-3H-imidazol-1-ium chloride;
3-[(2-Hydroxy-3,5-dichloro-4-methylphenylcarbamoyl)methyl]-1-methyl-3H-imidazol-1-ium chloride;
3-[(2-Hydroxy-3,5-dichloro-4-aminophenylcarbamoyl)methyl]-1-methyl-3H-imidazol-1-ium chloride;
3-[(2-Hydroxy-3,5-dichloro-4-acetylaminophenylcarbamoyl)methyl]-1-methyl-3H-imidazol-1-ium chloride;
3-[(2-Hydroxy-3,5-dichloro-4-methoxycarbonylaminophenylcarbamoyl)methyl]-1-methyl-3H-imidazol-1-ium chloride;
3-[(2-Hydroxy-3-acetylaminophenylcarbamoyl)methyl]-1-methyl-3H-imidazol-1-ium chloride;
1-[(2-Hydroxyphenylcarbamoyl)methyl]pyridinium chloride;
1-[(2-Hydroxy-3-(2-(pyridinium-1-yl)acetylamino)phenylcarbamoyl)methyl]pyridinium dichloride;
1-[(2-Hydroxy-4-(2-(pyridinium-1-yl)acetylamino)phenylcarbamoyl)methyl]pyridinium dichloride;
1-[(2-Hydroxy-4-methylphenylcarbamoyl)methyl]pyridinium chloride;
1-[(2-Hydroxy-4-aminophenylcarbamoyl)methyl]pyridinium chloride;
1-[(2-Hydroxy-4-acetylaminophenylcarbamoyl)methyl]pyridinium chloride;
1-[(2-Hydroxy-4-methoxycarbonylaminophenylcarbamoyl)methyl]pyridinium chloride;
1-[(3-Hydroxy-4-acetylaminophenylcarbamoyl)methyl]pyridinium chloride;
1-[(3-Hydroxy-4-methoxycarbonylaminophenylcarbamoyl)methyl]pyridinium chloride;
1-[(2-Hydroxy-5-chlorophenylcarbamoyl)methyl]pyridinium chloride;
1-[(2-Hydroxy-4-methyl-5-chlorophenylcarbamoyl)methyl]pyridinium chloride;
1-[(2-Hydroxy-4-amino-5-chlorophenylcarbamoyl)methyl]pyridinium chloride;
1-[(2-Hydroxy-4-acetylamino-5-chlorophenylcarbamoyl)methyl]pyridinium chloride;
1-[(2-Hydroxy-4-methoxycarbonylamino-5-chlorophenylcarbamoyl)methyl]pyridinium chloride;
1-[(3-Hydroxy-4-acetylamino-6-chlorophenylcarbamoyl)methyl]pyridinium chloride;
1-[(3-Hydroxy-4-methoxycarbonylamino-6-chlorophenylcarbamoyl)methyl]pyridinium chloride;
1-[(2-Hydroxy-5-methoxyphenylcarbamoyl)methyl]pyridinium chloride;
1-[(2-Hydroxy-4-methyl-5-methoxyphenylcarbamoyl)methyl]pyridinium chloride;
1-[(2-Hydroxy-4-amino-5-methoxyphenylcarbamoyl)methyl]pyridinium chloride;
1-[(2-Hydroxy-4-acetylamino-5-methoxyphenylcarbamoyl)methyl]pyridinium chloride;
1-[(2-Hydroxy-4-methoxycarbonylamino-5-methoxyphenylcarbamoyl)methyl]pyridinium chloride;
1-[(3-Hydroxy-4-acetylamino-6-methoxyphenylcarbamoyl)methyl]pyridinium chloride;
1-[(3-Hydroxy-4-methoxycarbonylamino-6-methoxyphenylcarbamoyl)methyl]pyridinium chloride;
1-[(2-Hydroxy-6-aminophenylcarbamoyl)methyl]pyridinium chloride;
1-[(2-Hydroxy-6-acetylaminophenylcarbamoyl)methyl]pyridinium chloride;
1-[(2-Hydroxy-4,6-diaminophenylcarbamoyl)methyl]pyridinium chloride;
1-[(2-Hydroxy-4-acetylamino-6-aminophenylcarbamoyl)methyl]pyridinium chloride;
1-[(2-Hydroxy-3,5-dichloro-4-methylphenylcarbamoyl)methyl]pyridinium chloride;
1-[(2-Hydroxy-3,5-dichloro-4-aminophenylcarbamoyl)methyl]pyridinium chloride;
1-[(2-Hydroxy-3,5-dichloro-4-acetylaminophenylcarbamoyl)methyl]pyridinium chloride;
1-[(2-Hydroxy-3,5-dichloro-4-methoxycarbonylaminophenylcarbamoyl)methyl]pyridinium chloride;
1-[(2-Hydroxy-3-acetylaminophenylcarbamoyl)methyl]pyridinium chloride;
1-[(2-Hydroxyphenylcarbamoyl)methyl]-1,4-dimethylpiperazin-1-ium chloride;
1-[(2-Hydroxy-3-(2-(1,4-dimethylpiperazin-1-ium-1-yl)acetyl)aminophenylcarbamoyl)methyl]-1,4-dimethylpiperazin-1-ium dichloride;
1-[(2-Hydroxy-4-(2-(1,4-dimethylpiperazin-1-ium-1-yl)acetyl)aminophenylcarbamoyl)methyl]-1,4-dimethylpiperazin-1-ium dichloride;
1-[(2-Hydroxy-4-methylphenylcarbamoyl)methyl]-1,4-dimethylpiperazin-1-ium chloride;
1-[(2-Hydroxy-4-aminophenylcarbamoyl)methyl]-1,4-dimethylpiperazin-1-ium chloride;
1-[(2-Hydroxy-4-acetylaminophenylcarbamoyl)methyl]-1,4-dimethylpiperazin-1-ium chloride;
1-[(2-Hydroxy-4-methoxycarbonylaminophenylcarbarnoyl)methyl]-1,4-dimethylpiperazin-1-ium chloride;
1-[(3-Hydroxy-4-acetylaminophenylcarbamoyl)methyl]-1,4-dimethylpiperazin-1-ium chloride;
1-[(3-Hydroxy-4-methoxycarbonylaminophenylcarbamoyl)methyl]-1,4-dimethylpiperazin-1-ium chloride;
1-[(2-Hydroxy-5-chlorophenylcarbamoyl)methyl]-1,4-dimethylpiperazin-1-ium chloride;
1-[(2-Hydroxy-4-methyl-5-chlorophenylcarbamoyl)methyl]-1,4-dimethylpiperazin-1-ium chloride;
1-[(2-Hydroxy-4-amino-5-chlorophenylcarbamoyl)methyl]-1,4-dimethylpiperazin-1-ium chloride;
1-[(2-Hydroxy-4-acetylamino-5-chlorophenylcarbamoyl)methyl]-1,4-dimethylpiperazin-1-ium chloride;
1-[(2-Hydroxy-4-methoxycarbonylamino-5-chlorophenylcarbamoyl)methyl]-1,4-dimethylpiperazin-1-ium chloride;
1-[(3-Hydroxy-4-acetylamino-6-chlorophenylcarbamoyl)methyl]-1,4-dimethylpiperazin-1-ium chloride;
1-[(3-Hydroxy-4-methoxycarbonylamino-6-chlorophenylcarbamoyl)methyl]-1,4-dimethylpiperazin-1-ium chloride;
1-[(2-Hydroxy-5-methoxyphenylcarbamoyl)methyl]-1,4-dimethylpiperazin-1-ium chloride;
1-[(2-Hydroxy-4-methyl-5-methoxyphenylcarbamoyl)methyl]-1,4-dimethylpiperazin-1-ium chloride;
1-[(2-Hydroxy-4-amino-5-methoxyphenylcarbamoyl)methyl]-1,4-dimethylpiperazin-1-ium chloride;
1-[(2-Hydroxy-4-acetylamino-5-methoxyphenylcarbamoyl)methyl]-1,4-dimethylpiperazin-1-ium chloride;
1-[(2-Hydroxy-4-methoxycarbonylamino-5-methoxyphenylcarbamoyl)methyl]-1,4-dimethylpiperazin-1-ium chloride;
1-[(3-Hydroxy-4-acetylamino-6-methoxyphenylcarbamoyl)methyl]-1,4-dimethylpiperazin-1-ium chloride;
1-[(3-Hydroxy-4-methoxycarbonylamino-6-methoxyphenylcarbamoyl)methyl]-1,4-dimethylpiperazin-1-ium chloride;
1-[(2-Hydroxy-6-aminophenylcarbamoyl)methyl]-1,4-dimethylpiperazin-1-ium chloride;

1-[(2-Hydroxy-6-acetylaminophenylcarbamoyl)methyl]-1,4-dimethylpiperazin-1-ium chloride;
1-[(2-Hydroxy-4,6-diaminophenylcarbamoyl)methyl]-1,4-dimethylpiperazin-1-ium chloride;
1-[(2-Hydroxy-4-acetylamino-6-aminophenylcarbamoyl)methyl]-1,4-dimethylpiperazin-1-ium chloride;
1-[(2-Hydroxy-3,5-dichloro-4-methylphenylcarbamoyl)methyl]-1,4-dimethylpiperazin-1-ium chloride;
1-[(2-Hydroxy-3,5-dichloro-4-aminophenylcarbamoyl)methyl]-1,4-dimethylpiperazin-1-ium chloride;
1-[(2-Hydroxy-3,5-dichloro-4-acetylaminophenylcarbamoyl)methyl]-1,4-dimethylpiperazin-1-ium chloride;
1-[(2-Hydroxy-3,5-dichloro-4-methoxycarbonylaminophenylcarbamoyl)methyl]-1,4-dimethylpiperazin-1-ium chloride;
1-[(2-Hydroxy-3-acetylaminophenylcarbamoyl)methyl]-1,4-dimethylpiperazin-1-ium chloride;
and acid addition salts of any of the foregoing compounds.

26. A composition according to claim 1, wherein said at least one coupler is present in an amount ranging from 0.0005% to 12% by weight relative to the total weight of the dyeing composition.

27. A composition according to claim 26, wherein said at least one coupler is present in an amount ranging from 0.005% to 6% by weight relative to the total weight of the dyeing composition.

28. A composition according to claim 1, wherein said at least one oxidation base is chosen from para-phenylenediamines, bisphenylalkylenediamines, para-aminophenols, ortho-aminophenols and heterocyclic bases, and acid addition salts of any of the foregoing compounds.

29. A composition according to claim 28, wherein said para-phenylenediamines are chosen from para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, and acid addition salts of any of the foregoing compounds.

30. A composition according to claim 29, wherein said para-phenylenediamines are chosen from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and acid addition salts of any of the foregoing compounds.

31. A composition according to claim 28, wherein said bisphenylalkylenediamines are chosen from N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,5-dioxaoctane, and acid addition salts of any of the foregoing compounds.

32. A composition according to claim 28, wherein said para-aminophenols are chosen from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and acid addition salts of any of the foregoing compounds.

33. A composition according to claim 28, wherein said ortho-aminophenols are chosen from 2-aminophenol, 2-amino-5-methylphenol, 2-amino-6-methylphenol, 5-acetamido-2-aminophenol, and acid addition salts of any of the foregoing compounds.

34. A composition according to claim 28, wherein said heterocyclic bases are chosen from pyridine derivatives, pyrimidine derivatives and pyrazole derivatives.

35. A composition according to claim 34, wherein said pyridine derivatives are chosen from 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and acid addition salts of any of the foregoing compounds.

36. A composition according to claim 34, wherein said pyrimidine derivatives are chosen from 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and pyrazolopyrimidine derivatives.

37. A composition according to claim 36, wherein said pyrazolopyrimidine derivatives are chosen from pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)-(2-hydroxyethyl)amino]ethanol, 5,6-dimethylpyrazolo[1,5-a]pyrimidin-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, 3-amino-5-methyl-7-imidazolylpropylaminopyrazolo[1,5-a]pyrimidine, their tautomeric forms, when a tautomeric equilibrium exists, and acid addition salts of any of the foregoing compounds.

38. A composition according to claim 34, wherein said pyrazole derivatives are chosen from 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1- methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and acid addition salts of any of the foregoing compounds.

39. A composition according to claim 1 further comprising at least one compound chosen from para-phenylenediamines and heterocyclic oxidation bases.

40. A composition according to claim 1, wherein said at least one oxidation base is present in an amount ranging from 0.0005% to 12% by weight relative to the total weight of the dyeing composition.

41. A composition according to claim 40, wherein said at least one oxidation base is present in an amount ranging from 0.005% to 6% by weight relative to the total weight of the dyeing composition.

42. A composition according to claim 1 further comprising at least one compound chosen from couplers and acid addition salts of any of said couplers, other than couplers of formula (I) and acid addition salts of any of said couplers of formula (I).

43. A composition according to claim 42, wherein said at least one compound, other than couplers of formula (I), is chosen from meta-phenylenediamines, meta-aminophenols, meta-diphenols and heterocyclic couplers.

44. A composition according to claim 43, wherein said heterocyclic couplers are chosen from indole derivatives, indoline derivatives, pyridine derivatives and pyrazolones, and acid addition salts of any of the foregoing compounds.

45. A composition according to claim 42, wherein said at least one compound, other than couplers of formula (I), is chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one, 1-phenyl-3-methylpyrazol-5-one, and acid addition salts of any of the foregoing compounds.

46. A composition according to claim 42, wherein said at least one compound, other than couplers of formula (I), is present in an amount ranging from 0.0001% to 10% by weight relative to the total weight of the dyeing composition.

47. A composition according to claim 46, wherein said at least one compound, other than couplers of formula (I), is present in an amount ranging from 0.005% to 5% by weight relative to the total weight of the dyeing composition.

48. A composition according to claim 1, wherein said acid addition salts are chosen from hydrochlorides, hydrobromides, sulfates, citrates, succinates, tartrates, lactates, and acetates.

49. A composition according to claim 42, wherein said acid addition salts are chosen from hydrochlorides, hydrobromides, sulfates, citrates, succinates, tartrates, lactates, and acetates.

50. A composition according to claim 28, wherein said acid addition salts are chosen from hydrochlorides, hydrobromides, sulfates, citrates, succinates, tartrates, lactates, and acetates.

51. A composition according to claim 1, wherein said medium suitable for dying is chosen from media comprising water and media comprising water and at least one organic solvent.

52. A composition according to claim 51, wherein said at least one organic solvent is chosen from $C_1$–$C_4$ alkanols, glycerol, glycols, glycol ethers, and aromatic alcohols.

53. A composition according to claim 52, wherein said $C_1$–$C_4$ alkanols are chosen from ethanol and isopropanol.

54. A composition according to claim 53, wherein said glycols and glycol ethers are chosen from 2-butoxyethenol, propylene glycol, monomethyl ether of propylene glycol, monoethyl ether of diethylene glycol and monomethyl ether of diethylene glycol.

55. A composition according to claim 52, wherein said aromatic alcohols are chosen from benzyl alcohol and phenoxyethanol.

56. A composition according to claim 51, wherein said at least one organic solvent is present in an amount ranging from 1% to 40% by weight relative to the total weight of th dyeing composition.

57. A composition according to claim 56, wherein said at least one organic solvent is present in an amount ranging from 5% to 30% by weight relative to the total weight of the dyeing composition.

58. A composition according to claim 1, wherein said dyeing composition has a pH ranging from 3 to 12.

59. A composition according to claim 58, wherein said dyeing composition has a pH ranging from 5 to 11.

60. A composition according to claim 58 wherein said pH is adjusted with at least one agent chosen from acidifying agents and alkalinizing agents.

61. A composition according to claim 60, wherein said acidifying agents are chosen from inorganic acids and organic acids.

62. A composition according to claim 61, wherein said inorganic acids and said organic acids are chosen from hydrochloric acid, orthophosphoric acid, sulfuric acid, and carboxylic acids.

63. A composition according to claim 62, wherein said carboxylic acids are chosen from acetic acid, tartaric acid, citric acid, lactic acid, and sulfonic acid.

64. A composition according to claim 60, wherein said alkalinizing agents are chosen from aqueous ammonia, alkali metal carbonates, alkanolamines, sodium hydroxide, potassium hydroxide, and compounds of formula (V):

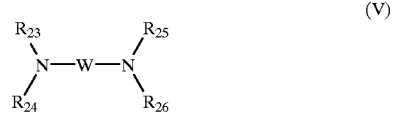

wherein W is a propylene residue, optionally substituted with a group chosen from a hydroxyl group and $C_1$–$C_6$ alkyl groups, and wherein $R_{23}$, $R_{24}$, $R_{25}$ and $R_{26}$, which are identical or different, are each chosen from a hydrogen atom, $C_1$–$C_6$ alkyl groups, and $C_1$–$C_6$ hydroxyalkyl groups.

65. A composition according to claim 64, wherein said alkanolamines are chosen from mono-, di-, and triethanolamine, and derivatives thereof.

66. A composition according to claim 1 further comprising at least one direct dye.

67. A composition according to claim 1 further comprising at least one adjuvant.

68. A composition according to claim 67, wherein said at least one adjuvant is chosen from anionic, cationic, nonionic, amphoteric and zwitterionic surfactants, anionic, cationic, nonionic, amphoteric and zwitterionic polymers, inorganic and organic thickeners, antioxidants, penetrating agents, sequestering agents, perfumes, buffers, dispersing agents, and conditioning agents.

69. A composition according to claim 68, wherein said conditioning agents are chosen from, modified and unmodified, volatile and nonvolatile silicones, film-forming agents, ceramides, preservatives, and opacifying agents.

70. A liquid, a cream, or a gel for oxidation dyeing keratinous fibers comprising, in a medium suitable for dyeing:
(a) at least one oxidation base; and
(b) at least one coupler chosen from compounds of formula (I) and acid addition salts of any of the foregoing compounds:

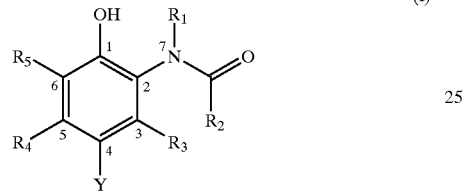

(I)

wherein:
at least one of $R_1$, $R_2$, $R_3$, $R_4$, and $R_5$, as defined below, is chosen from a group Z, as defined below;
$R_1$ is chosen from:
(1) a hydrogen atom;
(2) linear and branched, saturated and unsaturated groups containing from 1–15 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
(i) said $R_1$ does not comprise a group chosen from a peroxide group, a diazo group, a nitro group, and a nitroso group, and
(ii) said $SO_2$ group is not directly linked to the nitrogen atom at the 7-position of formula (I);
(3) a group Z chosen from cationic groups of formula (II);

(II)

wherein:
groups B are chosen from linear and branched, saturated and unsaturated groups containing from 1–15 carbon atoms, optionally substituted with at least one substituent chosen from a halogen atom and a group Z, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the proviso that:

(i) said B does not comprise a group chosen from a peroxide group, a diazo group, a nitro group, and a nitroso group; and
groups D are chosen from cationic groups of formulae (III) and (IV):

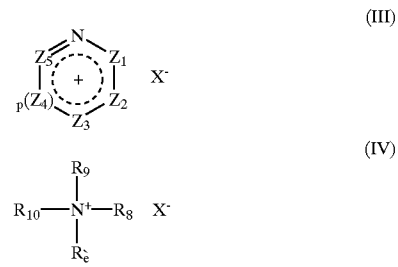

wherein:
group $Z_1$, group $Z_2$, group $Z_3$, and group $Z_4$, which are identical or different, are each chosen from
1) an oxygen atom and a sulfur atom,
2) a nitrogen atom, optionally substituted with an $R_{11}$ group, as defined below, and
3) a carbon atom, optionally substituted with one or two $R_{11}$ groups, as defined below, which are identical or different;
group $Z_5$ is chosen from
1) a nitrogen atom and
2) a carbon atom, optionally substituted with an $R_{11}$ group, as defined below;
two of the adjacent groups $Z_1$, $Z_2$, $Z_3$, $Z_4$ and $Z_5$ may optionally form a 5- to 7-membered ring, wherein each member is chosen from
1) an oxygen atom and a sulfur atom,
2) a nitrogen atom, optionally substituted with an $R_{11}$ group, as defined below, and
3) a carbon atom, optionally substituted with one or two $R_{11}$ groups, as defined below, which are identical or different;
wherein:
said groups $R_{11}$ are chosen from:
a hydrogen atom;
a group Z as defined above;
linear and branched, saturated and unsaturated groups containing from 1 to 10 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the proviso that:
(i) said $R_{11}$ does not comprise a group chosen from a peroxide group, a diazo group, a nitro group, and a nitroso group,
$Z_6$ is chosen from said $R_{11}$ groups, provided that $Z_6$ is not a hydrogen atom;
$Z_1$ and $Z_6$, or $Z_5$ and $Z_6$, optionally form a 5- to 7-membered ring chosen from saturated rings and unsaturated rings, wherein said members are each optionally substituted with one or two said radicals $R_{11}$, which are identical or different;
$R_e$, $R_8$, $R_9$, and $R_{10}$, which are identical or different, are each chosen from said groups $R_{11}$;

groups $R_7$, $R_8$, and $R_9$ optionally form, in pairs with the quaternary nitrogen atom to which they are attached, at least one 5- to 7-membered saturated ring, wherein said members are each chosen from
1) an oxygen atom and a sulfur atom,
2) a nitrogen atom, optionally substituted with a said $R_{11}$ group, and
3) a carbon atom, optionally substituted with one or two said $R_{11}$ groups, which are identical or different;

$X^-$ is chosen from organic anions and inorganic anions;

said groups B are linked to said groups D by any one of the atoms of said group D;

n and p, independently of each other, are equal to 0 or 1;

when n=0, then said group $R_{10}$ is optionally a direct bond, wherein said cationic group of formula (IV) is linked directly to said compound of formula (I) by way of the nitrogen cation of said cationic group of formula (IV);

$R_2$ is chosen from:
(1) a hydrogen atom;
(2) a group Z as defined above;
(3) linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
  (i) said $R_2$ does not comprise a group chosen from a peroxide group, a diazo group, a nitro group, and a nitroso group; and
  (ii) $R_2$ is not a hydroxyl or a thio group;

said $R_1$ and said $R_2$, together with the atoms to which they are attached, optionally form a 5- to 7-membered ring chosen from saturated rings and unsaturated rings, wherein said members are each chosen from a carbon atom, a nitrogen atom, an oxygen atom, a sulfur atom, and a carbonyl group, and said members are optionally substituted with 1 or 2 groups R, wherein
R is chosen from linear and branched, saturated and unsaturated, $C_1$–$C_6$ alkyl groups, optionally substituted with at least one halogen atom, wherein at least one carbon atom is optionally and independently replaced by an oxygen atom, a nitrogen atom, a sulfur atom, or an $SO_2$ group, and at least one branch of said branched $C_1$–$C_6$ alkyl group optionally forms at least one ring chosen from saturated and unsaturated 3- to 6-membered rings; with the proviso that:
  (i) said R does not comprise a group chosen from a peroxide group, a diazo group, a nitro group, and a nitroso group;

$R_3$ and $R_4$, which are identical or different, are each chosen from:
a hydrogen atom and halogen atoms;
a group Z as defined above;
linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally form at least one 3- to 7-membered ring comprising at least one carbon atom, with the provisos that:
  (i) said $R_3$ and said $R_4$ do not comprise a group chosen from a peroxide group, a diazo group, a nitro group, and a nitroso group;
  (ii) said $R_3$ and said $R_4$ are not a hydroxyl group; and
  (iii) said $R_3$ and said $R_4$ are not directly linked to the benzene ring of formula (I) by an —NH—NH— group;

$R_5$ is chosen from:
a hydrogen atom and halogen atoms;
a group Z as defined above;
linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
  (i) said $R_5$ does not comprise a group chosen from a peroxide group, a diazo group, a nitro group, and a nitroso group;
  (ii) said $R_5$ is chosen from a group other than a hydroxyl group, a thio group, an amino group, and an optionally substituted sulphonylamino group; and
  (iii) said $R_5$ is not directly linked to the benzene ring of formula (I) by a —NH—NH— group;

said $R_1$ and said $R_3$, together with the atoms to which they are attached, optionally form a 6- to 7-membered saturated ring, wherein said members are each chosen from a carbon atom, a nitrogen atom, an oxygen atom, a sulfur atom, and a carbonyl group, and said members are optionally substituted with 1 or 2 said groups R as defined above, with the proviso that:
  (i) said R does not comprise a group chosen from a peroxide group, a diazo group, a nitro group, and a nitroso group; and said $R_2$ and said $R_3$, together with the atoms to which they are attached, optionally form a 5- to 7-membered saturated ring, wherein said members are each chosen from a carbon atom, a nitrogen atom, an oxygen atom, a sulfur atom, and a carbonyl group, and said members are optionally substituted with 1 or 2 said groups R as defined above, with the proviso that:
  (i) said R does not comprise a group chosen from a peroxide group, a diazo group, a nitro group, and a nitroso group;
  (ii) when said $R_2$ and said $R_3$ form a 5- to 7-membered saturated ring, said $R_3$ optionally is a bond;

Y is chosen from:
a hydrogen atom and halogen atoms;
groups —$OR_6$, —$SR_6$ and —NH—$SO_2R_6$, wherein
  $R_6$ is chosen from linear and branched $C_1$–$C_6$ alkyl groups, optionally substituted with at least one group chosen from a halogen atom, a hydroxyl group, $C_1$–$C_4$ alkoxy groups, an amino group, amino($C_1$–$C_4$ alkyl) groups, wherein at least one branch of said $R_6$ optionally forms at least one 3- to 6-membered ring;
a phenyl group, optionally substituted with one or two groups chosen from $C_1$–$C_4$ alkyl groups, a trifluoromethyl group, a carboxyl group, $C_1$–$C_4$ alkoxycarbonyl groups, a halogen atom, a hydroxyl group, $C_1$–$C_4$ alkoxy groups, an amino group and amino ($C_1$–$C_4$ alkyl) groups; and a benzyl group, optionally substituted with one or two oxy groups.

71. A liquid, a cream, or a gel for oxidation dyeing keratinous fibers according to claim 70, wherein said keratinous fibers are human hair.

72. A process for oxidation dyeing keratinous fibers comprising (A) applying to said fibers at least one composition comprising, in a medium suitable for dyeing:

(a) at least one oxidation base; and (b) at least one coupler chosen from compounds of formula (I) and acid addition salts of any of the foregoing compounds:

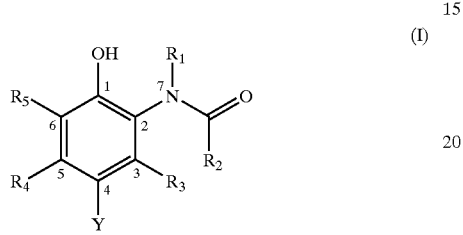

(I)

wherein:

at least one of $R_1$, $R_2$, $R_3$, $R_4$, and $R_5$, as defined below, is chosen from a group Z, as defined below;

$R_1$ is chosen from:

(1) a hydrogen atom;

(2) linear and branched, saturated and unsaturated groups containing from 1–15 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:

(i) said $R_1$ does not comprise a group chosen from a peroxide group, a diazo group, a nitro group, and a nitroso group, and (ii) said $SO_2$ group is not directly linked to the nitrogen atom at the 7-position of formula (I);

(3) a group Z chosen from cationic groups of formula (II);

(II)

wherein:

groups B are chosen from linear and branched, saturated and unsaturated groups containing from 1–15 carbon atoms, optionally substituted with at least one substituent chosen from a halogen atom and a group Z, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the proviso that:

(i) said B does not comprise a group chosen from a peroxide group, a diazo group, a nitro group, and a nitroso group; and groups D are chosen from cationic groups of formulae (III) and (IV):

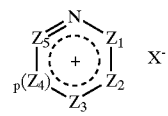

(III)

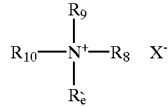

(IV)

wherein:

group $Z_1$, group $Z_2$, group $Z_3$, and group $Z_4$, which are identical or different, are each chosen from 1) an oxygen atom and a sulfur atom, 2) a nitrogen atom, optionally substituted with an $R_{11}$ group, as defined below, and 3) a carbon atom, optionally substituted with one or two $R_{11}$ groups, as defined below, which are identical or different;

group $Z_5$ is chosen from 1) a nitrogen atom and 2) a carbon atom, optionally substituted with an $R_{11}$ group, as defined below;

two of the adjacent groups $Z_1$, $Z_2$, $Z_3$, $Z_4$ and $Z_5$ may optionally form a 5- to 7-membered ring, wherein each member is chosen from 1) an oxygen atom and a sulfur atom, 2) a nitrogen atom, optionally substituted with an $R_{11}$ group, as defined below, and 3) a carbon atom, optionally substituted with one or two $R_{11}$ groups, as defined below, which are identical or different;

wherein:

said groups $R_{11}$ are chosen from:

a hydrogen atom;

a group Z as defined above;

linear and branched, saturated and unsaturated groups containing from 1 to 10 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the proviso that:

(i) said $R_{11}$ does not comprise a group chosen from a peroxide group, a diazo group, a nitro group, and a nitroso group, $Z_6$ is chosen from said $R_{11}$ groups, provided that $Z_6$ is not a hydrogen atom;

$Z_1$ and $Z_6$, or $Z_5$ and $Z_6$, optionally form a 5- to 7-membered ring chosen from saturated rings and unsaturated rings, wherein said members are each optionally substituted with one or two said radicals $R_{11}$, which are identical or different;

$R_{\dot{e}}$, $R_8$, $R_9$, and $R_{10}$, which are identical or different, are each chosen from said groups $R_{11}$;

groups $R_{\dot{e}}$, $R_8$, and $R_9$ optionally form, in pairs with the quaternary nitrogen atom to which they are attached, at least one 5- to 7-membered saturated ring, wherein said members are each chosen from 1) an oxygen atom and a sulfur atom,
2) a nitrogen atom, optionally substituted with a said $R_{11}$ group, and
3) a carbon atom, optionally substituted with one or two said $R_{11}$ groups, which are identical or different;

$X^-$ is chosen from organic anions and inorganic anions;

said groups B are linked to said groups D by any one of the atoms of said group D;

n and p, independently of each other, are equal to 0 or 1;

when n=0, then said group $R_{10}$ is optionally a direct bond, wherein said cationic group of formula (IV) is linked directly to said compound of formula (I) by way of the nitrogen cation of said cationic group of formula (IV);

$R_2$ is chosen from:
  (1) a hydrogen atom;
  (2) a group Z as defined above;
  (3) linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
    (i) said $R_2$ does not comprise a group chosen from a peroxide group, a diazo group, a nitro group, and a nitroso group; and
    (ii) $R_2$ is not a hydroxyl or a thio group;

said $R_1$ and said $R_2$, together with the atoms to which they are attached, optionally form a 5- to 7-membered ring chosen from saturated rings and unsaturated rings, wherein said members are each chosen from a carbon atom, a nitrogen atom, an oxygen atom, a sulfur atom, and a carbonyl group, and said members are optionally substituted with 1 or 2 groups R, wherein
  R is chosen from linear and branched, saturated and unsaturated, $C_1$–$C_6$ alkyl groups, optionally substituted with at least one halogen atom, wherein at least one carbon atom is optionally and independently replaced by an oxygen atom, a nitrogen atom, a sulfur atom, or an $SO_2$ group, and at least one branch of said branched $C_1$–$C_6$ alkyl group optionally forms at least one ring chosen from saturated and unsaturated 3- to 6-membered rings; with the proviso that:
    (i) said R does not comprise a group chosen from a peroxide group, a diazo group, a nitro group, and a nitroso group;

$R_3$ and $R_4$, which are identical or different, are each chosen from:
  a hydrogen atom and halogen atoms;
  a group Z as defined above;
  linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally form at least one 3- to 7-membered ring comprising at least one carbon atom, with the provisos that:
    (i) said $R_3$ and said $R_4$ do not comprise a group chosen from a peroxide group, a diazo group, a nitro group, and a nitroso group;
    (ii) said $R_3$ and said $R_4$ are not a hydroxyl group; and
    (iii) said $R_3$ and said $R_4$ are not directly linked to the benzene ring of formula (I) by an —NH—NH— group;

$R_5$ is chosen from:
  a hydrogen atom and halogen atoms;
  a group Z as defined above;
  linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
    (i) said $R_5$ does not comprise a group chosen from a peroxide group, a diazo group, a nitro group, and a nitroso group;
    (ii) said $R_5$ is chosen from a group other than a hydroxyl group, a thio group, an amino group, and an optionally substituted sulphonylamino group; and
    (iii) said $R_5$ is not directly linked to the benzene ring of formula (I) by a —NH—NH— group;

said $R_1$ and said $R_3$, together with the atoms to which they are attached, optionally form a 6- to 7-membered saturated ring, wherein said members are each chosen from a carbon atom, a nitrogen atom, an oxygen atom, a sulfur atom, and a carbonyl group, and said members are optionally substituted with 1 or 2 said groups R as defined above, with the proviso that:
  (i) said R does not comprise a group chosen from a peroxide group, a diazo group, a nitro group, and a nitroso group; and said $R_2$ and said $R_3$, together with the atoms to which they are attached, optionally form a 5- to 7-membered saturated ring, wherein said members are each chosen from a carbon atom, a nitrogen atom, an oxygen atom, a sulfur atom, and a carbonyl group, and said members are optionally substituted with 1 or 2 said groups R as defined above, with the proviso that:
  (i) said R does not comprise a group chosen from a peroxide group, a diazo group, a nitro group, and a nitroso group;
  (ii) when said $R_2$ and said $R_3$ form a 5- to 7-membered saturated ring, said $R_3$ optionally is a bond;

Y is chosen from:
  a hydrogen atom and halogen atoms;
  groups —$OR_6$, —$SR_6$ and —NH—$SO_2R_6$, wherein
    $R_6$ is chosen from linear and branched $C_1$–$C_6$ alkyl groups, optionally substituted with at least one group chosen from a halogen atom, a hydroxyl group, $C_1$–$C_4$ alkoxy groups, an amino group, amino($C_1$–$C_4$ alkyl) groups, wherein at least one branch of said $R_6$ optionally forms at least one 3- to 6-membered ring;
  a phenyl group, optionally substituted with one or two groups chosen from $C_1$–$C_4$ alkyl groups, a trifluoromethyl group, a carboxyl group, $C_1$–$C_4$ alkoxycarbonyl groups, a halogen atom, a hydroxyl group, $C_1$–$C_4$ alkoxy groups, an amino group and amino($C_1$–$C_4$ alkyl) groups; and
  a benzyl group, optionally substituted with one or two oxy groups, and (B) developing a color with at least one oxidizing agent, wherein said oxidizing agent is combined at the time of use with said at least one dyeing composition or said at least one oxidizing agent is applied simultaneously or sequentially to said at least one dyeing composition.

73. A process according to claim 72, wherein said at least one oxidizing agent is chosen from hydrogen peroxide, urea peroxide, alkali metal bromates, persalts and enzymes.

74. A process for oxidation dyeing keratinous fibers comprising:

(A) applying to said fibers at least one dyeing composition comprising, in a medium suitable for dyeing:
  (a) at least one oxidation base; and
  (b) at least one coupler chosen from compounds of formula (I) and acid addition salts of any of the foregoing compounds:

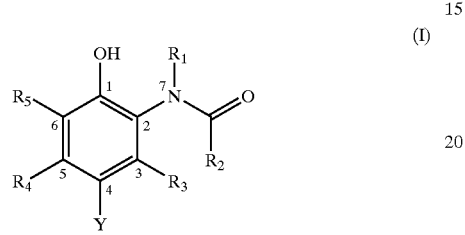

(I)

wherein:
at least one of $R_1$, $R_2$, $R_3$, $R_4$, and $R_5$, as defined below, is chosen from a group Z, as defined below;
$R_1$ is chosen from:
  (1) a hydrogen atom;
  (2) linear and branched, saturated and unsaturated groups containing from 1–15 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
    (i) said $R_1$ does not comprise a group chosen from a peroxide group, a diazo group, a nitro group, and a nitroso group, and
    (ii) said $SO_2$ group is not directly linked to the nitrogen atom at the 7-position of formula (I);
  (3) a group Z chosen from cationic groups of formula (II);

(II)

wherein:
groups B are chosen from linear and branched, saturated and unsaturated groups containing from 1–15 carbon atoms, optionally substituted with at least one substituent chosen from a halogen atom and a group Z, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the proviso that:
  (i) said B does not comprise a group chosen from a peroxide group, a diazo group, a nitro group, and a nitroso group; and
groups D are chosen from cationic groups of formulae (III) and (IV):

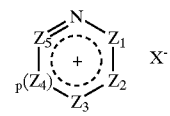

(III)

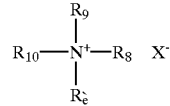

(IV)

wherein:
group $Z_1$, group $Z_2$, group $Z_3$, and group $Z_4$, which are identical or different, are each chosen from
  1) an oxygen atom and a sulfur atom,
  2) a nitrogen atom, optionally substituted with an $R_{11}$ group, as defined below, and
  3) a carbon atom, optionally substituted with one or two $R_{11}$ groups, as defined below, which are identical or different;
group $Z_5$ is chosen from
  1) a nitrogen atom and
  2) a carbon atom, optionally substituted with an $R_{11}$ group, as defined below;
two of the adjacent groups $Z_1$, $Z_2$, $Z_3$, $Z_4$ and $Z_5$ may optionally form a 5- to 7-membered ring, wherein each member is chosen from
  1) an oxygen atom and a sulfur atom,
  2) a nitrogen atom, optionally substituted with an $R_{11}$ group, as defined below, and
  3) a carbon atom, optionally substituted with one or two $R_{11}$ groups, as defined below, which are identical or different;
wherein:
said groups $R_{11}$ are chosen from:
  a hydrogen atom;
  a group Z as defined above;
  linear and branched, saturated and unsaturated groups containing from 1 to 10 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the proviso that:
(i) said $R_{11}$ does not comprise a group chosen from a peroxide group, a diazo group, a nitro group, and a nitroso group,
$Z_6$ is chosen from said $R_{11}$ groups, provided that $Z_6$ is not a hydrogen atom;
$Z_1$ and $Z_6$, or $Z_5$ and $Z_6$, optionally form a 5- to 7-membered ring chosen from saturated rings and unsaturated rings, wherein said members are each optionally substituted with one or two said radicals $R_{11}$, which are identical or different;
$R_8'$, $R_8$, $R_9$, and $R_{10}$, which are identical or different, are each chosen from said groups $R_{11}$;
groups $R_8'$, $R_8$, and $R_9$ optionally form, in pairs with the quaternary nitrogen atom to which they are attached, at least one 5- to 7-membered saturated ring, wherein said members are each chosen 1) an oxygen atom and a sulfur atom,
2) a nitrogen atom, optionally substituted with a said $R_{11}$ group, and
3) a carbon atom, optionally substituted with one or two said $R_{11}$ groups, which are identical or different;

$X^-$ is chosen from organic anions and inorganic anions;

said groups B are linked to said groups D by any one of the atoms of said group D;

n and p, independently of each other, are equal to 0 or 1;

when n=0, then said group $R_{10}$ is optionally a direct bond, wherein said cationic group of formula (IV) is linked directly to said compound of formula (I) by way of the nitrogen cation of said cationic group of formula (IV);

$R_2$ is chosen from:
(1) a hydrogen atom;
(2) a group Z as defined above;
(3) linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
  (i) said $R_2$ does not comprise a group chosen from a peroxide group, a diazo group, a nitro group, and a nitroso group; and
  (ii) $R_2$ is not a hydroxyl or a thio group;

said $R_1$ and said $R_2$, together with the atoms to which they are attached, optionally form a 5- to 7-membered ring chosen from saturated rings and unsaturated rings, wherein said members are each chosen from a carbon atom, a nitrogen atom, an oxygen atom, a sulfur atom, and a carbonyl group, and said members are optionally substituted with 1 or 2 groups R, wherein
  R is chosen from linear and branched, saturated and unsaturated, $C_1$–$C_6$ alkyl groups, optionally substituted with at least one halogen atom, wherein at least one carbon atom is optionally and independently replaced by an oxygen atom, a nitrogen atom, a sulfur atom, or an $SO_2$ group, and at least one branch of said branched $C_1$–$C_6$ alkyl group optionally forms at least one ring chosen from saturated and unsaturated 3- to 6-membered rings; with the proviso that:
    (i) said R does not comprise a group chosen from a peroxide group, a diazo group, a nitro group, and a nitroso group;

$R_3$ and $R_4$, which are identical or different, are each chosen from:
  a hydrogen atom and halogen atoms;
  a group Z as defined above;
  linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally form at least one 3- to 7-membered ring comprising at least one carbon atom, with the provisos that:
    (i) said $R_3$ and said $R_4$ do not comprise a group chosen from a peroxide group, a diazo group, a nitro group, and a nitroso group;
    (ii) said $R_3$ and said $R_4$ are not a hydroxyl group; and
    (iii) said $R_3$ and said $R_4$ are not directly linked to the benzene ring of formula (I) by an —NH—NH— group;

$R_5$ is chosen from:
  a hydrogen atom and halogen atoms;
  a group Z as defined above;
  linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
    (i) said $R_5$ does not comprise a group chosen from a peroxide group, a diazo group, a nitro group, and a nitroso group;
    (ii) said $R_5$ is chosen from a group other than a hydroxyl group, a thio group, an amino group, and an optionally substituted sulphonylamino group; and
    (iii) said $R_5$ is not directly linked to the benzene ring of formula (I) by a —NH—NH— group;

said $R_1$ and said $R_3$, together with the atoms to which they are attached, optionally form a 6- to 7-membered saturated ring, wherein said members are each chosen from a carbon atom, a nitrogen atom, an oxygen atom, a sulfur atom, and a carbonyl group, and said members are optionally substituted with 1 or 2 said groups R as defined above, with the proviso that:
  (i) said R does not comprise a group chosen from a peroxide group, a diazo group, a nitro group, and a nitroso group; and said $R_2$ and said $R_3$, together with the atoms to which they are attached, optionally form a 5- to 7-membered saturated ring, wherein said members are each chosen from a carbon atom, a nitrogen atom, an oxygen atom, a sulfur atom, and a carbonyl group, and said members are optionally substituted with 1 or 2 said groups R as defined above, with the proviso that:
  (i) said R does not comprise a group chosen from a peroxide group, a diazo group, a nitro group, and a nitroso group;
  (ii) when said $R_2$ and said $R_3$ form a 5- to 7-membered saturated ring, said $R_3$ optionally is a bond;

Y is chosen from:
  a hydrogen atom and halogen atoms;
  groups —$OR_6$, —$SR_6$ and —NH—$SO_2R_6$, wherein
    $R_6$ is chosen from linear and branched $C_1$–$C_6$ alkyl groups, optionally substituted with at least one group chosen from a halogen atom, a hydroxyl group, $C_1$–$C_4$ alkoxy groups, an amino group, amino($C_1$–$C_4$ alkyl) groups, wherein at least one branch of said $R_6$ optionally forms at least one 3- to 6-membered ring;
  a phenyl group, optionally substituted with one or two groups chosen from $C_1$–$C_4$ alkyl groups, a trifluoromethyl group, a carboxyl group, $C_1$–$C_4$ alkoxycarbonyl groups, a halogen atom, a hydroxyl group, $C_1$–$C_4$ alkoxy groups, an amino group and amino($C_1$–$C_4$ alkyl) groups; and
  a benzyl group, optionally substituted with one or two oxy groups, and (B) developing a color with at least one oxidizing composition comprising, in a medium suitable for dyeing, at least one oxidizing agent present in an amount sufficient to develop a color, wherein said at least one oxidizing composition is combined at the time of use with said at least one dyeing composition, (C) leaving said combination to act for a time ranging from 3 to 50 minutes, and (D) rinsing said keratinous fibers, shampooing said keratinous fibers after said shampooing, and drying said keratinous fibers.

75. A process according to claim 74, wherein said at least one oxidizing agent is chosen from hydrogen peroxide, urea peroxide, alkali metal bromates, persalts and enzymes.

76. A kit comprising two compartments, wherein:

(A) a first compartment comprises at least one dyeing composition comprising, in a medium suitable for dyeing:
(a) at least one oxidation base; and
(b) at least one coupler chosen from compounds of formula (I) and acid addition salts of any of the foregoing compounds:

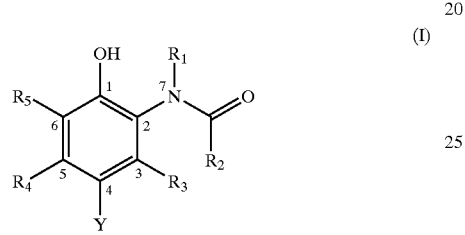

wherein:
at least one of $R_1$, $R_2$, $R_3$, $R_4$, and $R_5$, as defined below, is chosen from a group Z, as defined below;

$R_1$ is chosen from:
(1) a hydrogen atom;
(2) linear and branched, saturated and unsaturated groups containing from 1–15 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
  (i) said $R_1$ does not comprise a group chosen from a peroxide group, a diazo group, a nitro group, and a nitroso group, and
  (ii) said $SO_2$ group is not directly linked to the nitrogen atom at the 7-position of formula (I);
(3) a group Z chosen from cationic groups of formula (II);

wherein:
groups B are chosen from linear and branched, saturated and unsaturated groups containing from 1–15 carbon atoms, optionally substituted with at least one substituent chosen from a halogen atom and a group Z, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the proviso that:

(i) said B does not comprise a group chosen from a peroxide group, a diazo group, a nitro group, and a nitroso group; and groups D are chosen from cationic groups of formulae (III) and (IV):

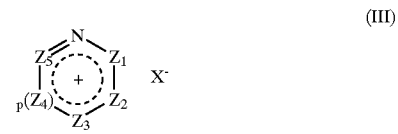

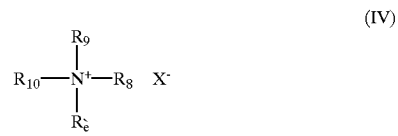

wherein:
group $Z_1$, group $Z_2$, group $Z_3$, and group $Z_4$, which are identical or different, are each chosen from
  1) an oxygen atom and a sulfur atom,
  2) a nitrogen atom, optionally substituted with an $R_{11}$ group, as defined below, and
  3) a carbon atom, optionally substituted with one or two $R_{11}$ groups, as defined below, which are identical or different;
group $Z_5$ is chosen from
  1) a nitrogen atom and
  2) a carbon atom, optionally substituted with an $R_{11}$ group, as defined below;
two of the adjacent groups $Z_1$, $Z_2$, $Z_3$, $Z_4$ and $Z_5$ may optionally form a 5- to 7-membered ring, wherein each member is chosen from
  1) an oxygen atom and a sulfur atom,
  2) a nitrogen atom, optionally substituted with an $R_{11}$ group, as defined below, and
  3) a carbon atom, optionally substituted with one or two $R_{11}$ groups, as defined below, which are identical or different;
wherein:
said groups $R_{11}$ are chosen from:
  a hydrogen atom;
  a group Z as defined above;
  linear and branched, saturated and unsaturated groups containing from 1 to 10 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the proviso that:
(i) said $R_{11}$ does not comprise a group chosen from a peroxide group, a diazo group, a nitro group, and a nitroso group,
$Z_6$ is chosen from said $R_{11}$ groups, provided that $Z_6$ is not a hydrogen atom;
$Z_1$ and $Z_6$, or $Z_5$ and $Z_6$, optionally form a 5- to 7-membered ring chosen from saturated rings and unsaturated rings, wherein said members are each optionally substituted with one or two said radicals $R_{11}$, which are identical or different;
$R_e$, $R_8$, $R_9$, and $R_{10}$, which are identical or different, are each chosen from said groups $R_{11}$;

groups $R_7$, $R_8$, and $R_9$ optionally form, in pairs with the quaternary nitrogen atom to which they are attached, at least one 5- to 7-membered saturated ring, wherein said members are each chosen from
1) an oxygen atom and a sulfur atom,
2) a nitrogen atom, optionally substituted with a said $R_{11}$ group, and
3) a carbon atom, optionally substituted with one or two said $R_{11}$ groups, which are identical or different;

$X^-$ is chosen from organic anions and inorganic anions;

said groups B are linked to said groups D by any one of the atoms of said group D;

n and p, independently of each other, are equal to 0 or 1;

when n=0, then said group $R_{10}$ is optionally a direct bond, wherein said cationic group of formula (IV) is linked directly to said compound of formula (I) by way of the nitrogen cation of said cationic group of formula (IV);

$R_2$ is chosen from:
(1) a hydrogen atom;
(2) a group Z as defined above;
(3) linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
 (i) said $R_2$ does not comprise a group chosen from a peroxide group, a diazo group, a nitro group, and a nitroso group; and
 (ii) $R_2$ is not a hydroxyl or a thio group;

said $R_1$ and said $R_2$, together with the atoms to which they are attached, optionally form a 5- to 7-membered ring chosen from saturated rings and unsaturated rings, wherein said members are each chosen from a carbon atom, a nitrogen atom, an oxygen atom, a sulfur atom, and a carbonyl group, and said members are optionally substituted with 1 or 2 groups R, wherein
 R is chosen from linear and branched, saturated and unsaturated, $C_1$–$C_6$ alkyl groups, optionally substituted with at least one halogen atom, wherein at least one carbon atom is optionally and independently replaced by an oxygen atom, a nitrogen atom, a sulfur atom, or an $SO_2$ group, and at least one branch of said branched $C_1$–$C_6$ alkyl group optionally forms at least one ring chosen from saturated and unsaturated 3- to 6-membered rings; with the proviso that:
  (i) said R does not comprise a group chosen from a peroxide group, a diazo group, a nitro group, and a nitroso group;

$R_3$ and $R_4$, which are identical or different, are each chosen from:
 a hydrogen atom and halogen atoms;
 a group Z as defined above;
 linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally form at least one 3- to 7-membered ring comprising at least one carbon atom, with the provisos that:
  (i) said $R_3$ and said $R_4$ do not comprise a group chosen from a peroxide group, a diazo group, a nitro group, and a nitroso group;
  (ii) said $R_3$ and said $R_4$ are not a hydroxyl group; and
  (iii) said $R_3$ and said $R_4$ are not directly linked to the benzene ring of formula (I) by an —NH—NH— group;

$R_5$ is chosen from:
 a hydrogen atom and halogen atoms;
 a group Z as defined above;
 linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
  (i) said $R_5$ does not comprise a group chosen from a peroxide group, a diazo group, a nitro group, and a nitroso group;
  (ii) said $R_5$ is chosen from a group other than a hydroxyl group, a thio group, an amino group, and an optionally substituted sulphonylamino group; and
  (iii) said $R_5$ is not directly linked to the benzene ring of formula (I) by a —NH—NH— group;

said $R_1$ and said $R_3$, together with the atoms to which they are attached, optionally form a 6- to 7-membered saturated ring, wherein said members are each chosen from a carbon atom, a nitrogen atom, an oxygen atom, a sulfur atom, and a carbonyl group, and said members are optionally substituted with 1 or 2 said groups R as defined above, with the proviso that:
 (i) said R does not comprise a group chosen from a peroxide group, a diazo group, a nitro group, and a nitroso group; and said $R_2$ and said $R_3$, together with the atoms to which they are attached, optionally form a 5- to 7-membered saturated ring, wherein said members are each chosen from a carbon atom, a nitrogen atom, an oxygen atom, a sulfur atom, and a carbonyl group, and said members are optionally substituted with 1 or 2 said groups R as defined above, with the proviso that:
 (i) said R does not comprise a group chosen from a peroxide group, a diazo group, a nitro group, and a nitroso group;
 (ii) when said $R_2$ and said $R_3$ form a 5- to 7-membered saturated ring, said $R_3$ optionally is a bond;

Y is chosen from:
 a hydrogen atom and halogen atoms;
 groups —$OR_6$, —$SR_6$ and —NH—$SO_2R_6$, wherein
  $R_6$ is chosen from linear and branched $C_1$–$C_6$ alkyl groups, optionally substituted with at least one group chosen from a halogen atom, a hydroxyl group, $C_1$–$C_4$ alkoxy groups, an amino group, amino($C_1$–$C_4$ alkyl) groups, wherein at least one branch of said $R_6$ optionally forms at least one 3- to 6-membered ring;
  a phenyl group, optionally substituted with one or two groups chosen from $C_1$–$C_4$ alkyl groups, a trifluoromethyl group, a carboxyl group, $C_1$–$C_4$ alkoxycarbonyl groups, a halogen atom, a hydroxyl group, $C_1$–$C_4$ alkoxy groups, an amino group and amino($C_1$–$C_4$ alkyl) groups; and a benzyl group, optionally substituted with one or two oxy groups, and (B) a second compartment comprises at least one oxidizing composition.

77. A compound of formula (I') or an acid addition salt thereof:

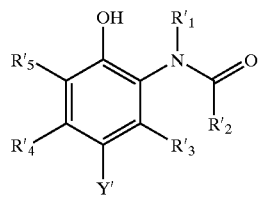

(I')

wherein at least one of said groups $R'_1$, $R'_2$, $R'_3$, $R'_4$, and $R'_5$, as defined below, is a group Z', as defined below, and wherein:

$R'_1$ is chosen from:
(1) a hydrogen atom;
(2) linear and branched, saturated and unsaturated groups containing from 1–15 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
  (i) said $R'_1$ does not comprise a group chosen from a peroxide group, a diazo group, a nitro group, and a nitroso group, and
  (ii) said $SO_2$ group is not directly linked to the nitrogen atom at the 7-position of formula (I);
(3) a group Z' chosen from cationic groups of formula (II);

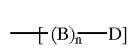

(II)

wherein:
groups B are chosen from linear and branched, saturated and unsaturated groups containing from 1–15 carbon atoms, optionally substituted with at least one substituent chosen from a halogen atom and a group Z, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the proviso that:
  (i) said B does not comprise a group chosen from a peroxide group, a diazo group, a nitro group, and a nitroso group; and
groups D are chosen from cationic groups of formulae (III) and (IV):

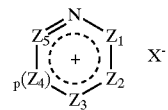

(III)

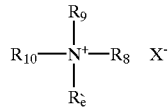

(IV)

wherein:
group $Z_1$, group $Z_2$, group $Z_3$, and group $Z_4$, which are identical or different, are each chosen from
  1) an oxygen atom and a sulfur atom,
  2) a nitrogen atom, optionally substituted with an $R_{11}$ group, as defined below, and
  3) a carbon atom, optionally substituted with one or two $R_{11}$ groups, as defined below, which are identical or different;
group $Z_5$ is chosen from
  1) a nitrogen atom and
  2) a carbon atom, optionally substituted with an $R_{11}$ group, as defined below;
two of the adjacent groups $Z_1$, $Z_2$, $Z_3$, $Z_4$ and $Z_5$ may optionally form a 5- to 7-membered ring, wherein each member is chosen from
  1) an oxygen atom and a sulfur atom,
  2) a nitrogen atom, optionally substituted with an $R_{11}$ group, as defined below, and
  3) a carbon atom, optionally substituted with one or two $R_{11}$ groups, as defined below, which are identical or different;
wherein:
said groups $R_{11}$ are chosen from:
  a hydrogen atom;
  a group Z' as defined above;
  linear and branched, saturated and unsaturated groups containing from 1 to 10 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the proviso that:
(i) said $R_{11}$ does not comprise a group chosen from a peroxide group, a diazo group, a nitro group, and a nitroso group,
$Z_6$ is chosen from said $R_{11}$ groups, provided that $Z_6$ is not a hydrogen atom;
$Z_1$ and $Z_6$, or $Z_5$ and $Z_6$, optionally form a 5- to 7-membered ring chosen from saturated rings and unsaturated rings, wherein said members are each optionally substituted with one or two said radicals $R_{11}$, which are identical or different;
$R_{\dot{e}}$, $R_8$, $R_9$, and $R_{10}$, which are identical or different, are each chosen from said groups $R_{11}$;
groups $R_{\dot{e}}$, $R_8$, and $R_9$ optionally form, in pairs with the quaternary nitrogen atom to which they are attached, at least one 5- to 7-membered saturated ring, wherein said members are each chosen from 1) an oxygen atom and a sulfur atom,
2) a nitrogen atom, optionally substituted with a said $R_{11}$ group, and
3) a carbon atom, optionally substituted with one or two said $R_{11}$ groups, which are identical or different;

$X^-$ is chosen from organic anions and inorganic anions;

said groups B are linked to said groups D by any one of the atoms of said group D;

n and p, independently of each other, are equal to 0 or 1;

when n=0, then said group $R_{10}$ is optionally a direct bond, wherein said cationic group of formula (IV) is linked directly to said compound of formula (I) by way of the nitrogen cation of said cationic group of formula (IV);

$R'_2$ is chosen from:
(1) a hydrogen atom;
(2) a group Z' as defined above;
(3) linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
(i) said $R'_2$ does not comprise a group chosen from a peroxide group, a diazo group, a nitro group, and a nitroso group; and
(ii) $R'_2$ is not a hydroxyl or a thio group;

said $R'_1$ and said $R'_2$, together with the atoms to which they are attached, optionally form a 5- to 7-membered ring chosen from saturated rings and unsaturated rings, wherein said members are each chosen from a carbon atom, a nitrogen atom, an oxygen atom, a sulfur atom, and a carbonyl group, and said members are optionally substituted with 1 or 2 groups R, wherein R is chosen from linear and branched, saturated and unsaturated, $C_1$–$C_6$ alkyl groups, optionally substituted with at least one halogen atom, wherein at least one carbon atom is optionally and independently replaced by an oxygen atom, a nitrogen atom, a sulfur atom, or an $SO_2$ group, and at least one branch of said branched $C_1$–$C_6$ alkyl group optionally forms at least one ring chosen from saturated and unsaturated 3- to 6-membered rings; with the proviso that:
(i) said R does not comprise a group chosen from a peroxide group, a diazo group, a nitro group, and a nitroso group;

$R'_3$ and $R'_4$, which are identical or different, are each chosen from:
a hydrogen atom and halogen atoms;
a group Z' as defined above;
linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally form at least one 3- to 7-membered ring comprising at least one carbon atom, with the provisos that:
(i) said $R'_3$ and said $R'_4$ do not comprise a group chosen from a peroxide group, a diazo group, a nitro group, and a nitroso group;
(ii) said $R'_3$ and said $R'_4$ are not a hydroxyl group; and
(iii) said $R'_3$ and said $R'_4$ are not directly linked to the benzene ring of formula (I) by an —NH—NH— group;

$R'_5$ is chosen from:
a hydrogen atom and halogen atoms;
a group Z' as defined above;
linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
(i) said $R'_5$ does not comprise a group chosen from a peroxide group, a diazo group, a nitro group, and a nitroso group;
(ii) said $R'_5$ is chosen from a group other than a hydroxyl group, a thio group, an amino group, and an optionally substituted sulphonylamino group; and
(iii) said $R'_5$ is not directly linked to the benzene ring of formula (I) by a —NH—NH— group;

said $R'_1$ and said $R'_3$, together with the atoms to which they are attached, optionally form a 6- to 7-membered saturated ring, wherein said members are each chosen from a carbon atom, a nitrogen atom, an oxygen atom, a sulfur atom, and a carbonyl group, and said members are optionally substituted with 1 or 2 said groups R as defined above, with the proviso that:
(i) said R does not comprise a group chosen from a peroxide group, a diazo group, a nitro group, and a nitroso group; and said $R'_2$ and said $R'_3$, together with the atoms to which they are attached, optionally form a 5- to 7-membered saturated ring, wherein said members are each chosen from a carbon atom, a nitrogen atom, an oxygen atom, a sulfur atom, and a carbonyl group, and said members are optionally substituted with 1 or 2 said groups R as defined above, with the proviso that:
(i) said R does not comprise a group chosen from a peroxide group, a diazo group, a nitro group, and a nitroso group;
(ii) when said $R'_2$ and said $R'_3$ form a 5- to 7-membered saturated ring, said $R'_3$ optionally is a bond;

Y' is chosen from:
a hydrogen atom and halogen atoms;
groups —$OR_6$, —$SR_6$ and —NH—$SO_2R_6$, wherein
$R_6$ is chosen from linear and branched $C_1$–$C_6$ alkyl groups, optionally substituted with at least one group chosen from a halogen atom, a hydroxyl group, $C_1$–$C_4$ alkoxy groups, an amino group, amino($C_1$–$C_4$ alkyl) groups, wherein at least one branch of said $R_6$ optionally forms at least one 3- to 6-membered ring;
a phenyl group, optionally substituted with one or two groups chosen from $C_1$–$C_4$ alkyl groups, a trifluoromethyl group, a carboxyl group, $C_1$–$C_4$ alkoxycarbonyl groups, a halogen atom, a hydroxyl group, $C_1$–$C_4$ alkoxy groups, an amino group and amino($C_1$–$C_4$ alkyl) groups; and
a benzyl group, optionally substituted with one or two oxy groups, and further provided that said compound of formula (I') is not one of the following compounds:

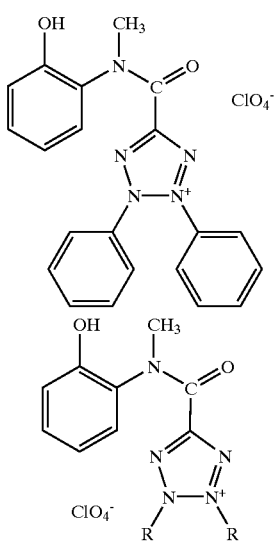

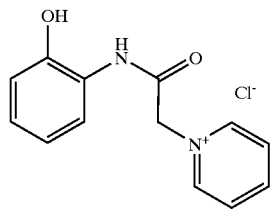

wherein R is chosen from
4-methyl-C$_6$H$_4$, 4-chloro-C$_6$H$_4$ and
2-ethoxy-C$_6$H$_4$ groups

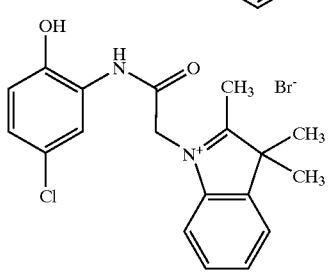

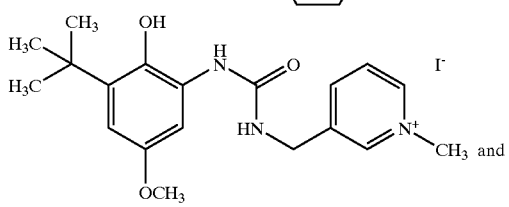

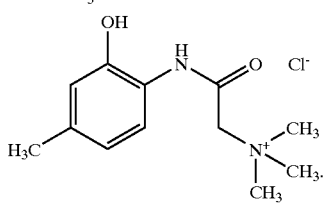

78. A compound chosen from:
3-[(2-Hydroxyphenylcarbamoyl)methyl]-1-methyl-3H-imidazol-1-ium chloride;
3-[(2-Hydroxy-3-(2-(3-methyl-1H-imidazol-3-ium-1-yl)acetylamino)phenylcarbamoyl)methyl]-1-methyl-3H-imidazol-1-ium dichloride;
3-[(2-Hydroxy-4-(2-(3-methyl-1H-imidazol-3-ium-1-yl)acetylamino)phenylcarbamoyl)methyl]-1-methyl-3H-imidazol-1-ium dichloride;
3-[(2-Hydroxy-4-methylphenylcarbamoyl)methyl]-1-methyl-3H-imidazol-1-ium chloride;
3-[(2-Hydroxy-4-aminophenylcarbamoyl)methyl]-1-methyl-3H-imidazol-1-ium chloride;
3-[(2-Hydroxy-4-acetylaminophenylcarbamoyl)methyl]-1-methyl-3H-imidazol-1-ium chloride;
3-[(2-Hydroxy-4-methoxycarbonylaminophenylcarbamoyl)methyl]-1-methyl-3H-imidazol-1-ium chloride;
3-[(3-Hydroxy-4-acetylaminophenylcarbamoyl)methyl]-1-methyl-3H-imidazol-1-ium chloride;
3-[(3-Hydroxy-4-methoxycarbonylaminophenylcarbamoyl)methyl]-1-methyl-3H-imidazol-1-ium chloride;
3-[(2-Hydroxy-5-chlorophenylcarbamoyl)methyl]-1-methyl-3H-imidazol-1-ium chloride;
3-[(2-Hydroxy-4-methyl-5-chlorophenylcarbamoyl)methyl]-1-methyl-3H-imidazol-1-ium chloride;
3-[(2-Hydroxy-4-amino-5-chlorophenylcarbamoyl)methyl]-1-methyl-3H-imidazol-1-ium chloride;
3-[(2-Hydroxy-4-acetylamino-5-chlorophenylcarbamoyl)methyl]-1-methyl-3H-imidazol-1-ium chloride;
3-[(2-Hydroxy-4-methoxycarbonylamino-5-chlorophenylcarbamoyl)methyl]-1-methyl-3H-imidazol-1-ium chloride;
3-[(3-Hydroxy-4-acetylamino-5-chlorophenylcarbamoyl)methyl]-1-methyl-3H-imidazol-1-ium chloride;
3-[(3-Hydroxy-4-methoxycarbonylamino-6-chlorophenylcarbamoyl)methyl]-1-methyl-3H-imidazol-1-ium chloride;
3-[(2-Hydroxy-5-methoxyphenylcarbamoyl)methyl]-1-methyl-3H-imidazol-1-ium chloride;
3-[(2-Hydroxy-4-methyl-5-methoxyphenylcarbamoyl)methyl]-1-methyl-3H-imidazol-1-ium chloride;
3-[(2-Hydroxy-4-amino-5-methoxyphenylcarbamoyl)methyl]-1-methyl-3H-imidazol-1-ium chloride;
3-[(2-Hydroxy-4-acetylamino-5-methoxyphenylcarbamoyl)methyl]-1-methyl-3H-imidazol-1-ium chloride;
3-[(2-Hydroxy-4-methoxycarbonylamino-5-methoxyphenylcarbamoyl)methyl]-1-methyl-3H-imidazol-1-ium chloride;
3-[(3-Hydroxy-4-acetylamino-6-methoxyphenylcarbamoyl)methyl]-1-methyl-3H-imidazol-1-ium chloride;
3-[(3-Hydroxy-4-methoxycarbonylamino-6-methoxyphenylcarbamoyl)methyl]-1-methyl-3H-imidazol-1-ium chloride;
3-[(2-Hydroxy-6-aminophenylcarbamoyl)methyl]-1-methyl-3H-imidazol-1-ium chloride;
3-[(2-Hydroxy-6-acetylaminophenylcarbamoyl)methyl]-1-methyl-3H-imidazol-1-ium chloride;
3-[(2-Hydroxy-4,6-diaminophenylcarbamoyl)methyl]-1-methyl-3H-imidazol-1-ium chloride;
3-[(2-Hydroxy-4-acetylamino-6-aminophenylcarbamoyl)methyl]-1-methyl-3H-imidazol-1-ium chloride;
3-[(2-Hydroxy-3,5-dichloro-4-methylphenylcarbamoyl)methyl]-1-methyl-3H-imidazol-1-ium chloride;
3-[(2-Hydroxy-3,5-dichloro-4-aminophenylcarbamoyl)methyl]-1-methyl-3H-imidazol-1-ium chloride;
3-[(2-Hydroxy-3,5-dichloro-4-acetylaminophenylcarbamoyl)methyl]-1-methyl-3H-imidazol-1-ium chloride;
3-[(2-Hydroxy-3,5-dichloro-4-methoxycarbonylaminophenylcarbamoyl)methyl]-1-methyl-3H-imidazol-1-ium chloride;
3-[(2-Hydroxy-3-acetylaminophenylcarbamoyl)methyl]-1-methyl-3H-imidazol-1-ium chloride;
1-[(2-Hydroxyphenylcarbamoyl)methyl]pyridinium chloride;
1-[(2-Hydroxy-3-(2-(pyridinium-1-yl)acetylamino)phenylcarbamoyl)methyl]pyridinium dichloride;

1-[(2-Hydroxy-4-(2-(pyridinium-1-yl)acetylamino) phenylcarbamoyl)methyl]pyridinium dichloride;
1-[(2-Hydroxy-4-methylphenylcarbamoyl)methyl] pyridinium chloride;
1-[(2-Hydroxy-4-aminophenylcarbamoyl)methyl] pyridinium chloride;
1-[(2-Hydroxy-4-acetylaminophenylcarbamoyl)methyl] pyridinium chloride;
1-[(2-Hydroxy-4-methoxycarbonylaminophenylcarbamoyl) methyl]pyridinium chloride;
1-[(3-Hydroxy-4-acetylaminophenylcarbamoyl)methyl] pyridinium chloride;
1-[(3-Hydroxy-4-methoxycarbonylaminophenylcarbamoyl) methyl]pyridinium chloride;
1-[(2-Hydroxy-5-chlorophenylcarbamoyl)methyl] pyridinium chloride;
1-[(2-Hydroxy-4-methyl-5-chlorophenylcarbamoyl)methyl] pyridinium chloride;
1-[(2-Hydroxy-4-amino-5-chlorophenylcarbamoyl)methyl] pyridinium chloride;
1-[(2-Hydroxy-4-acetylamino-5-chlorophenylcarbamoyl) methyl]pyridinium chloride;
1-[(2-Hydroxy-4-methoxycarbonylamino-5-chlorophenylcarbamoyl)methyl]pyridinium chloride;
1-[(3-Hydroxy-4-acetylamino-6-chlorophenylcarbamoyl) methyl]pyridinium chloride;
1-[(3-Hydroxy-4-methoxycarbonylamino-6-chlorophenylcarbamoyl)methyl]pyridinium chloride;
1-[(2-Hydroxy-5-methoxyphenylcarbamoyl)methyl] pyridinium chloride;
1-[(2-Hydroxy-4-methyl-5-methoxyphenylcarbamoyl) methyl]pyridinium chloride;
1-[(2-Hydroxy-4-amino-5-methoxyphenylcarbamoyl) methyl]pyridinium chloride;
1-[(2-Hydroxy-4-acetylamino-5-methoxyphenylcarbamoyl) methyl]pyridinium chloride;
1-[(2-Hydroxy-4-methoxycarbonylamino-5-methoxyphenylcarbamoyl)methyl]pyridinium chloride;
1-[(3-Hydroxy-4-acetylamino-6-methoxyphenylcarbamoyl) methyl]pyridinium chloride;
1-[(3-Hydroxy-4-methoxycarbonylamino-6-methoxyphenylcarbamoyl)methyl]pyridinium chloride;
1-[(2-Hydroxy-6-aminophenylcarbamoyl)methyl] pyridinium chloride;
1-[(2-Hydroxy-6-acetylaminophenylcarbamoyl)methyl] pyrdinium chloride;
1-[(2-Hydroxy-4,6-diaminophenylcarbamoyl)methyl] pyridinium chloride;
1-[(2-Hydroxy-4-acetylamino-6-aminophenylcarbamoyl) methyl]pyridinium chloride;
1-[(2-Hydroxy-3,5-dichloro-4-methylphenylcarbamoyl) methyl]pyridinium chloride;
1-[(2-Hydroxy-3,5-dichloro-4-aminophenylcarbamoyl) methyl]pyridinium chloride;
1-[(2-Hydroxy-3,5-dichloro-4-acetylaminophenylcarbamoyl)methyl]pyridinium chloride;
1-[(2-Hydroxy-3,5-dichloro-4-methoxycarbonylaminophenylcarbamoyl)methyl]pyridinium chloride;
1-[(2-Hydroxy-3-acetylaminophenylcarbamoyl)methyl] pyridinium chloride;
1-[(2-Hydroxyphenylcarbamoyl)methyl]-1,4-dimethylpiperazin-1-ium chloride;
1-[(2-Hydroxy-3-(2-(1,4-dimethylpiperazin-1-ium-1-yl) acetyl)aminophenylcarbamoyl)methyl]-1,4-dimethylpiperazin-1-ium dichloride;
1-[(2-Hydroxy-4-(2-(1,4-dimethylpiperazin-1-ium-1-yl) acetyl)aminophenylcarbamoyl)methyl]-1,4-dimethylpiperazin-1-ium dichloride;
1-[(2-Hydroxy-4-methylphenylcarbamoyl)methyl]-1,4-dimethylpiperazin-1-ium chloride;
1-[(2-Hydroxy-4-aminophenylcarbamoyl)methyl]-1,4-dimethylpiperazin-1-ium chloride;
1-[(2-Hydroxy-4-acetylaminophenylcarbamoyl)methyl]-1,4-dimethylpiperazin-1-ium chloride;
1-[(2-Hydroxy-4-methoxycarbonylaminophenylcarbamoyl) methyl]-1,4-dimethylpiperazin-1-ium chloride;
1-[(3-Hydroxy-4-acetylaminophenylcarbamoyl)methyl]-1,4-dimethylpiperazin-1-ium chloride;
1-[(3-Hydroxy-4-methoxycarbonylaminophenylcarbamoyl) methyl]-1,4-dimethylpiperazin-1-ium chloride;
1-[(2-Hydroxy-5-chlorophenylcarbamoyl)methyl]-1,4-dimethylpiperazin-1-ium chloride;
1-[(2-Hydroxy-4-methyl-5-chlorophenylcarbamoyl) methyl]-1,4-dimethylpiperazin-1-ium chloride;
1-[(2-Hydroxy-4-amino-5-chlorophenylcarbamoyl)methyl]-1,4-dimethylpiperazin-1-ium chloride;
1-[(2-Hydroxy-4-acetylamino-5-chlorophenylcarbamoyl) methyl]-1,4-dimethylpiperazin-1-ium chloride;
1-[(2-Hydroxy-4-methoxycarbonylamino-5-chlorophenylcarbamoyl)methyl]-1,4-dimethylpiperazin-1-ium chloride;
1-[(3-Hydroxy-4-acetylamino-6-chlorophenylcarbamoyl) methyl]-1,4-dimethylpiperazin-1-ium chloride;
1-[(3-Hydroxy-4-methoxycarbonylamino-6-chlorophenylcarbamoyl)methyl]-1,4-dimethylpiperazin-1-ium chloride;
1-[(2-Hydroxy-5-methoxyphenylcarbamoyl)methyl]-1,4-dimethylpiperazin-1-ium chloride;
1-[(2-Hydroxy-4-methyl-5-methoxyphenylcarbamoyl) methyl]-1,4-dimethylpiperazin-1-ium chloride;
1-[(2-Hydroxy-4-amino-5-methoxyphenylcarbamoyl) methyl]-1,4-dimethylpiperazin-1-ium chloride;
1-[(2-Hydroxy-4-acetylamino-5-methoxyphenylcarbamoyl) methyl]-1,4-dimethylpiperazin-1-ium chloride;
1-[(2-Hydroxy-4-methoxycarbonylamino-5-methoxyphenylcarbamoyl)methyl]-1,4-dimethylpiperazin-1-ium chloride;
1-[(3-Hydroxy-4-acetylamino-6-methoxyphenylcarbamoyl) methyl]-1,4-dimethylpiperazin-1-ium chloride;
1-[(3-Hydroxy-4-methoxycarbonylamino-6-methoxyphenylcarbamoyl)methyl]-1,4-dimethylpiperazin-1-ium chloride;
1-[(2-Hydroxy-6-aminophenylcarbamoyl)methyl]-1,4-dimethylpiperazin-1-ium chloride;
1-[(2-Hydroxy-6-acetylaminophenylcarbamoyl)methyl]-1,4-dimethylpiperazin-1-ium chloride;
1-[(2-Hydroxy-4,6-diaminophenylcarbamoyl)methyl]-1,4-dimethylpiperazin-1-ium chloride;
1-[(2-Hydroxy-4-acetylamino-6-aminophenylcarbamoyl) methyl]-1,4-dimethylpiperazin-1-ium chloride;
1-[(2-Hydroxy-3,5-dichloro-4-methylphenylcarbamoyl) methyl]-1,4-dimethylpiperazin-1-ium chloride;
1-[(2-Hydroxy-3,5-dichloro-4-aminophenylcarbamoyl) methyl]-1,4-dimethylpiperazin-1-ium chloride;
1-[(2-Hydroxy-3,5-dichloro-4-acetylaminophenylcarbamoyl)methyl]-1,4-dimethylpiperazin-1-ium chloride;
1-[(2-Hydroxy-3,5-dichloro-4-methoxycarbonylaminophenylcarbamoyl)methyl]-1,4-dimethylpiperazin-1-ium chloride;
1-[(2-Hydroxy-3-acetylaminophenylcarbamoyl)methyl]-1,4-dimethylpiperazin-1-ium chloride;
or an acid addition salt of any of the foregoing compounds.

79. A process for oxidation dyeing keratinous fibers comprising applying to said keratinous fibres at least one coupler chosen from compounds of formula (I') and acid addition salts of any of the foregoing compounds:

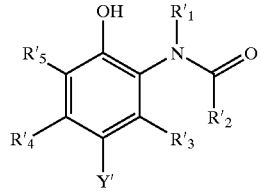

(I')

wherein
at least one of said groups $R'_1$, $R'_2$, $R'_3$, $R'_4$, and $R'_5$, as defined below, is a group Z', as defined below, and wherein:

$R'_1$ is chosen from:
(1) a hydrogen atom;
(2) linear and branched, saturated and unsaturated groups containing from 1–15 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
   (i) said $R'_1$ does not comprise a group chosen from a peroxide group, a diazo group, a nitro group, and a nitroso group, and
   (ii) said $SO_2$ group is not directly linked to the nitrogen atom at the 7-position of formula (I);
(3) a group Z' chosen from cationic groups of formula (II);

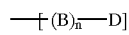

(II)

wherein:
groups B are chosen from linear and branched, saturated and unsaturated groups containing from 1–15 carbon atoms, optionally substituted with at least one substituent chosen from a halogen atom and a group Z, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the proviso that:
   (i) said B does not comprise a group chosen from a peroxide group, a diazo group, a nitro group, and a nitroso group; and
groups D are chosen from cationic groups of formulae (III) and (IV):

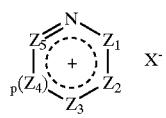

(III)

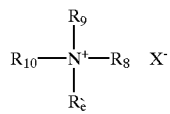

(IV)

wherein:
group $Z_1$, group $Z_2$, group $Z_3$, and group $Z_4$, which are identical or different, are each chosen from
   1) an oxygen atom and a sulfur atom,
   2) a nitrogen atom, optionally substituted with an $R_{11}$ group, as defined below, and
   3) a carbon atom, optionally substituted with one or two $R_{11}$ groups, as defined below, which are identical or different;
group $Z_5$ is chosen from
   1) a nitrogen atom and
   2) a carbon atom, optionally substituted with an $R_{11}$ group, as defined below;
two of the adjacent groups $Z_1$, $Z_2$, $Z_3$, $Z_4$ and $Z_5$ may optionally form a 5- to 7-membered ring, wherein each member is chosen from
   1) an oxygen atom and a sulfur atom,
   2) a nitrogen atom, optionally substituted with an $R_{11}$ group, as defined below, and
   3) a carbon atom, optionally substituted with one or two $R_{11}$ groups, as defined below, which are identical or different;
wherein:
said groups $R_{11}$ are chosen from:
   a hydrogen atom;
   a group Z' as defined above;
   linear and branched, saturated and unsaturated groups containing from 1 to 10 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the proviso that:
   (i) said $R_{11}$ does not comprise a group chosen from a peroxide group, a diazo group, a nitro group, and a nitroso group,
$Z_6$ is chosen from said $R_{11}$ groups, provided that $Z_6$ is not a hydrogen atom;
$Z_1$ and $Z_6$, or $Z_5$ and $Z_6$, optionally form a 5- to 7-membered ring chosen from saturated rings and unsaturated rings, wherein said members are each optionally substituted with one or two said radicals $R_{11}$, which are identical or different;
$R_{\dot{e}}$, $R_8$, $R_9$, and $R_{10}$, which are identical or different, are each chosen from said groups $R_{11}$;
groups $R_{\dot{e}}$, $R_8$, and $R_9$ optionally form, in pairs with the quaternary nitrogen atom to which they are attached, at least one 5- to 7-membered saturated ring, wherein said members are each chosen from
   1) an oxygen atom and a sulfur atom,
   2) a nitrogen atom, optionally substituted with a said $R_{11}$ group, and
   3) a carbon atom, optionally substituted with one or two said $R_{11}$ groups, which are identical or different;

X⁻ is chosen from organic anions and inorganic anions;

said groups B are linked to said groups D by any one of the atoms of said group D;

n and p, independently of each other, are equal to 0 or 1;

when n=0, then said group $R_{10}$ is optionally a direct bond, wherein said cationic group of formula (IV) is linked directly to said compound of formula (I) by way of the nitrogen cation of said cationic group of formula (IV);

$R'_2$ is chosen from:
(1) a hydrogen atom;
(2) a group Z' as defined above;
(3) linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
  (i) said $R'_2$ does not comprise a group chosen from a peroxide group, a diazo group, a nitro group, and a nitroso group; and
  (ii) $R'_2$ is not a hydroxyl or a thio group;

said $R'_1$ and said $R'_2$, together with the atoms to which they are attached, optionally form a 5- to 7-membered ring chosen from saturated rings and unsaturated rings, wherein said members are each chosen from a carbon atom, a nitrogen atom, an oxygen atom, a sulfur atom, and a carbonyl group, and said members are optionally substituted with 1 or 2 groups R, wherein
  R is chosen from linear and branched, saturated and unsaturated, $C_1$–$C_6$ alkyl groups, optionally substituted with at least one halogen atom, wherein at least one carbon atom is optionally and independently replaced by an oxygen atom, a nitrogen atom, a sulfur atom, or an $SO_2$ group, and at least one branch of said branched $C_1$–$C_6$ alkyl group optionally forms at least one ring chosen from saturated and unsaturated 3- to 6-membered rings; with the proviso that:
  (i) said R does not comprise a group chosen from a peroxide group, a diazo group, a nitro group, and a nitroso group;

$R'_3$ and $R'_4$, which are identical or different, are each chosen from:
a hydrogen atom and halogen atoms;
a group Z' as defined above;
linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally form at least one 3- to 7-membered ring comprising at least one carbon atom, with the provisos that:
  (i) said $R'_3$ and said $R'_4$ do not comprise a group chosen from a peroxide group, a diazo group, a nitro group, and a nitroso group;
  (ii) said $R'_3$ and said $R'_4$ are not a hydroxyl group; and
  (iii) said $R'_3$ and said $R'_4$ are not directly linked to the benzene ring of formula (I) by an —NH—NH— group;

$R'_5$ is chosen from:
a hydrogen atom and halogen atoms;
a group Z' as defined above;
linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
  (i) said $R'_5$ does not comprise a group chosen from a peroxide group, a diazo group, a nitro group, and a nitroso group;
  (ii) said $R'_5$ is chosen from a group other than a hydroxyl group, a thio group, an amino group, and an optionally substituted sulphonylamino group; and
  (iii) said $R'_5$ is not directly linked to the benzene ring of formula (I) by a —NH—NH— group;

said $R'_1$ and said $R'_3$, together with the atoms to which they are attached, optionally form a 6- to 7-membered saturated ring, wherein said members are each chosen from a carbon atom, a nitrogen atom, an oxygen atom, a sulfur atom, and a carbonyl group, and said members are optionally substituted with 1 or 2 said groups R as defined above, with the proviso that:
  (i) said R does not comprise a group chosen from a peroxide group, a diazo group, a nitro group, and a nitroso group; and said $R'_2$ and said $R'_3$, together with the atoms to which they are attached, optionally form a 5- to 7-membered saturated ring, wherein said members are each chosen from a carbon atom, a nitrogen atom, an oxygen atom, a sulfur atom, and a carbonyl group, and said members are optionally substituted with 1 or 2 said groups R as defined above, with the proviso that:
  (i) said R does not comprise a group chosen from a peroxide group, a diazo group, a nitro group, and a nitroso group;
  (ii) when said $R'_2$ and said $R'_3$ form a 5- to 7-membered saturated ring, said $R'_3$ optionally is a bond;

Y' is chosen from:
a hydrogen atom and halogen atoms;
groups —$OR_6$, —$SR_6$ and —NH—$SO_2R_6$, wherein
  $R_6$ is chosen from linear and branched $C_1$–$C_6$ alkyl groups, optionally substituted with at least one group chosen from a halogen atom, a hydroxyl group, $C_1$–$C_4$ alkoxy groups, an amino group, amino($C_1$–$C_4$ alkyl) groups, wherein at least one branch of said $R_6$ optionally forms at least one 3- to 6-membered ring;
  a phenyl group, optionally substituted with one or two groups chosen from $C_1$–$C_4$ alkyl groups, a trifluoromethyl group, a carboxyl group, $C_1$–$C_4$ alkoxycarbonyl groups, a halogen atom, a hydroxyl group, $C_1$–$C_4$ alkoxy groups, an amino group and amino($C_1$–$C_4$ alkyl) groups; and
  a benzyl group, optionally substituted with one or two oxy groups, and further provided that said compound of formula (I') is not one of the following compounds:

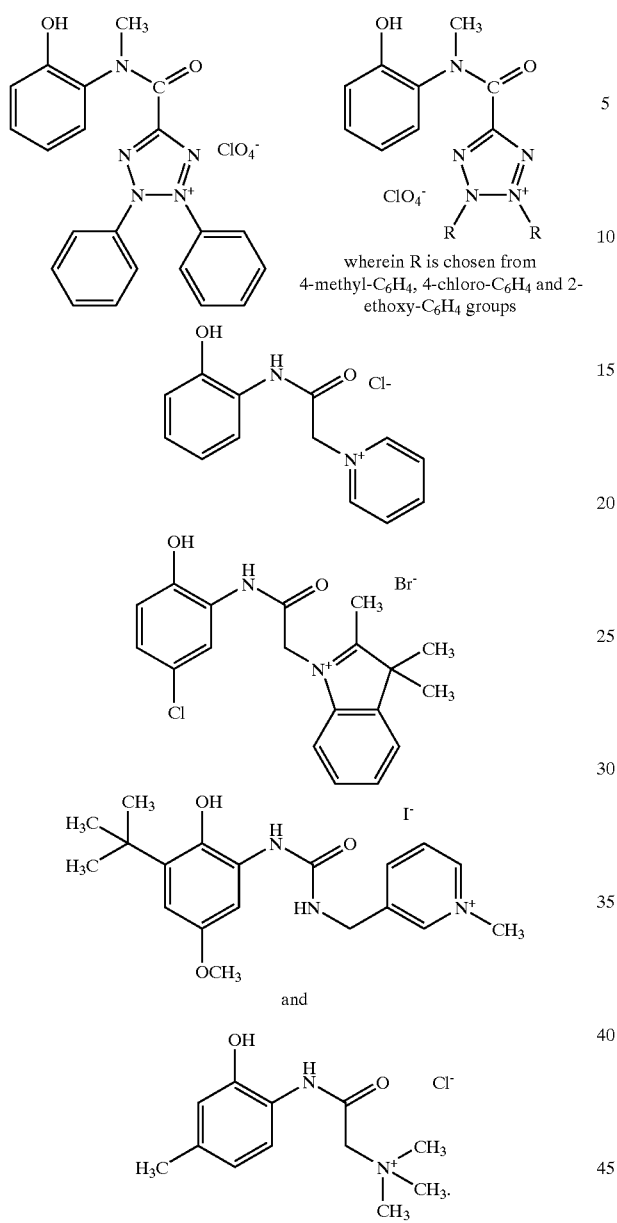

wherein R is chosen from
4-methyl-$C_6H_4$, 4-chloro-$C_6H_4$ and 2-ethoxy-$C_6H_4$ groups and 80. A composition according to claim 1, wherein said unsaturated alkyl groups comprise at least one unit of unsaturation chosen from double bonds and triple bonds.

81. A compound of formula (I') or an acid addition salt thereof:

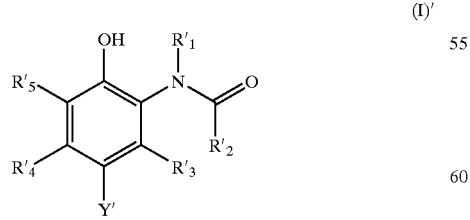
(I')

wherein
at least one of said groups $R'_1$, $R'_2$, $R'_3$, $R'_4$, and $R'_5$, as defined below, is a group Z', as defined below, and wherein:

$R'_1$ is chosen from:
(1) a hydrogen atom;
(2) linear and branched, saturated and unsaturated groups containing from 1–15 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
  (i) said $R'_1$ does not comprise a group chosen from a peroxide group, a diazo group, a nitro group, and a nitroso group, and
  (ii) said $SO_2$ group is not directly linked to the nitrogen atom at the 7-position of formula (I);
(3) a group Z' chosen from cationic groups of formula (II);

(II)

wherein:
groups B are chosen from linear and branched, saturated and unsaturated groups containing from 1–15 carbon atoms, optionally substituted with at least one substituent chosen from a halogen atom and a group Z, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the proviso that:
  (i) said B does not comprise a group chosen from a peroxide group, a diazo group, a nitro group, and a nitroso group; and
groups D are chosen from cationic groups of formulae (III) and (IV):

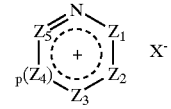
(III)

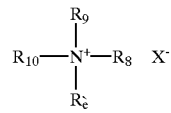
(IV)

wherein:
group $Z_1$, group $Z_2$, group $Z_3$, and group $Z_4$, which are identical or different, are each chosen from
  1) an oxygen atom and a sulfur atom,
  2) a nitrogen atom, optionally substituted with an $R_{11}$ group, as defined below, and
  3) a carbon atom, optionally substituted with one or two $R_{11}$ groups, as defined below, which are identical or different;
group $Z_5$ is chosen from
  1) a nitrogen atom and
  2) a carbon atom, optionally substituted with an $R_{11}$ group, as defined below;
two of the adjacent groups $Z_1$, $Z_2$, $Z_3$, $Z_4$ and $Z_5$ may optionally form a 5- to 7-membered ring, wherein each member is chosen from
  1) an oxygen and a sulfur atom,
  2) a nitrogen atom, optionally substituted with an $R_{11}$ group, as defined below, and
  3) a carbon atom, optionally substituted with one or two $R_{11}$ groups, as defined below, which are identical or different;

wherein:
said groups $R_{11}$ are chosen from:
a hydrogen atom;
a group Z' as defined above;
linear and branched, saturated and unsaturated groups containing from 1 to 10 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the proviso that:
(i) said $R_{11}$ does not comprise a group chosen from a peroxide group, a diazo group, a nitro group, and a nitroso group,
$Z_6$ is chosen from said $R_{11}$ groups, provided that $Z_6$ is not a hydrogen atom;
$Z_1$ and $Z_6$, or $Z_5$ and $Z_6$, optionally form a 5- to 7-membered ring chosen from saturated rings and unsaturated rings, wherein said members are each optionally substituted with one or two said radicals $R_{11}$, which are identical or different;
$R_7$, $R_8$, $R_9$, and $R_{10}$, which are identical or different, are each chosen from said groups $R_{11}$;
groups $R_7$, $R_8$, and $R_9$ optionally form, in pairs with the quaternary nitrogen atom to which they are attached, at least one 5- to 7-membered saturated ring, wherein said members are each chosen from
1) an oxygen atom and a sulfur atom,
2) a nitrogen atom, optionally substituted with a said $R_{11}$ group, and
3) a carbon atom, optionally substituted with one or two said $R_{11}$ groups, which are identical or different;
$X^-$ is chosen from organic anions and inorganic anions;
said groups B are linked to said groups D by any one of the atoms of said group D;
n and p, independently of each other, are equal to 0 or 1;
when n=0, then said group $R_{10}$ is optionally a direct bond, wherein said cationic group of formula (IV) is linked directly to said compound of formula (I) by way of the nitrogen cation of said cationic group of formula (IV);
$R'_2$ is chosen from:
(1) a hydrogen atom;
(2) a group Z' as defined above;
(3) linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
(i) said $R'_2$ does not comprise a group chosen from a peroxide group, a diazo group, a nitro group, and a nitroso group; and
(ii) $R'_2$ is not a hydroxyl or a thio group;
said $R'_1$ and said $R'_2$, together with the atoms to which they are attached, optionally form a 5- to 7-membered ring chosen from saturated rings and unsaturated rings, wherein said members are each chosen from a carbon atom, a nitrogen atom, an oxygen atom, a sulfur atom, and a carbonyl group, and said members are optionally substituted with 1 or 2 groups R, wherein
R is chosen from linear and branched, saturated and unsaturated, $C_1$–$C_6$ alkyl groups, optionally substituted with at least one halogen atom, wherein at least one carbon atom is optionally and independently replaced by an oxygen atom, a nitrogen atom, a sulfur atom, or an $SO_2$ group, and at least one branch of said branched $C_1$–$C_6$ alkyl group optionally forms at least one ring chosen from saturated and unsaturated 3- to 6-membered rings; with the proviso that:
(i) said R does not comprise a group chosen from a peroxide group, a diazo group, a nitro group, and a nitroso group;
$R'_3$ and $R'_4$, which are identical or different, are each chosen from:
a hydrogen atom and halogen atoms;
a group Z' as defined above;
linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally form at least one 3- to 7-membered ring comprising at least one carbon atom, with the provisos that:
(i) said $R'_3$ and said $R'_4$ do not comprise a group chosen from a peroxide group, a diazo group, a nitro group, and a nitroso group;
(ii) said $R'_3$ and said $R'_4$ are not a hydroxyl group; and
(iii) said $R'_3$ and said $R'_4$ are not directly linked to the benzene ring of formula (I) by an —NH—NH— group;
$R'_5$ is chosen from:
a hydrogen atom and halogen atoms;
a group Z' as defined above;
linear and branched, saturated and unsaturated groups containing from 1–20 carbon atoms, optionally substituted with at least one halogen atom, wherein at least one carbon atom is optionally and independently replaced by an oxygen atom, a nitrogen atom, a sulfur atom, or an $SO_2$ group, and at least one branch of said branched groups optionally forms at least one 3- to 7-membered ring comprising at least one carbon atom, with the provisos that:
(i) said $R'_5$ does not comprise a group chosen from a peroxide group, a diazo group, a nitro group, and a nitroso group;
(ii) said $R'_5$ is chosen from a group other than a hydroxyl group, a thio group, an amino group, and an optionally substituted sulphonylamino group; and
(iii) said $R'_5$ is not directly linked to the benzene ring of formula (I) by a —NH—NH— group;
said $R'_1$ and said $R'_3$, together with the atoms to which they are attached, optionally form a 6- to 7-membered saturated ring, wherein said members are each chosen from a carbon atom, a nitrogen atom, an oxygen atom, a sulfur atom, and a carbonyl group, and said members are optionally substituted with 1 or 2 said groups R as defined above, with the proviso that:
(i) said R does not comprise a group chosen from a peroxide group, a diazo group, a nitro group, and a nitroso group; and
said $R'_2$ and said $R'_3$, together with the atoms to which they are attached, optionally form a 5- to 7-membered saturated ring, wherein said members are each chosen from a carbon atom, a nitrogen atom, an oxygen atom, a sulfur atom, and a carbonyl group, and said members are optionally substituted with 1 or 2 said groups R as defined above, with the proviso that:
(i) said R does not comprise a group chosen from a peroxide group, a diazo group, a nitro group, and a nitroso group;
(ii) when said R'$_2$ and said R'$_3$ form a 5- to 7-membered saturated ring, said R'$_3$ optionally is a bond;

Y' is chosen from:
a hydrogen atom and halogen atoms;
groups —OR$_6$, —SR$_6$ and —NH—SO$_2$R$_6$, wherein R$_6$ is chosen from linear and branched C$_1$–C$_6$ alkyl groups, optionally substituted with at least one group chosen from a halogen atom, a hydroxyl group, C$_1$–C$_4$ alkoxy groups, an amino group, amino(C$_1$–C$_4$ alkyl) groups, wherein at least one branch of said R$_6$ optionally forms at least one 3- to 6-membered ring;
a phenyl group, optionally substituted with one or two groups chosen from C$_1$–C$_4$ alkyl groups, a trifluoromethyl group, a carboxyl group, C$_1$–C$_4$ alkoxycarbonyl groups, a halogen atom, a hydroxyl group, C$_1$–C$_4$ alkoxy groups, an amino group and amino(C$_1$–C$_4$ alkyl) groups; and
a benzyl group, optionally substituted with one or two oxy groups, and further provided that said compound of formula (I') is not one of the following compounds:

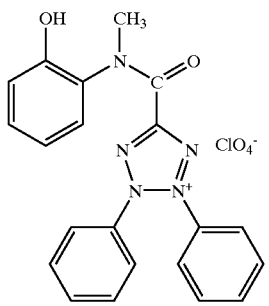

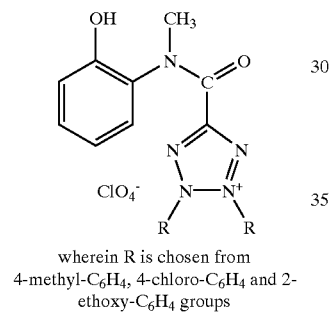

wherein R is chosen from 4-methyl-C$_6$H$_4$, 4-chloro-C$_6$H$_4$ and 2-ethoxy-C$_6$H$_4$ groups -continued

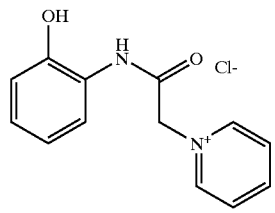

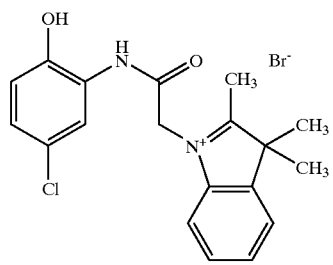

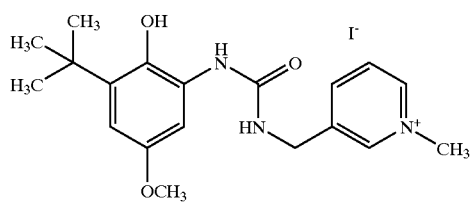

and

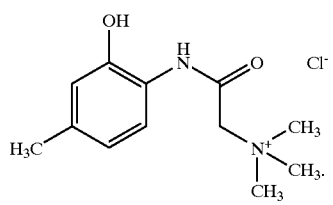

* * * * *

UNITED STATES PATENT AND TRADEMARK OFFICE
CERTIFICATE OF CORRECTION

PATENT NO. : 6,544,298 B1
DATED : April 8, 2003
INVENTOR(S) : Laurent Vidal et al.

It is certified that error appears in the above-identified patent and that said Letters Patent is hereby corrected as shown below:

<u>Title page, Item [54] and Column 1, lines 3-5,</u>
Title, after "COUPLER", and "COUPLERS", insert a comma; and after "DYEING" (first occurrence), insert a comma.

<u>Column 29,</u>
Line 24, after "an $R_{11}$", delete the comma.

<u>Column 33,</u>
Line 9, "optionally from" should read -- optionally form --.

<u>Column 53,</u>
Line 48, after "$Z_1$", delete the comma.

<u>Column 68,</u>
Line 2, "5to" should read -- 5- to --; and after "7-membered", insert -- ring, --.
Line 3, after "wherein", insert -- each --.

<u>Column 73,</u>
Line 12, "group Rio" should read -- group $R_{10}$ --.
Line 46, "$C_{1-6}$ alkyl" should read -- $C_1$-$C_6$ alkyl --.

<u>Column 80,</u>
Lines 14-15, "1,2,4-triazoliniurm," should read -- 1,2,4-triazolinium, --.
Line 33, "1,2,4-triazolinium4-yl," should read -- 1,2,4-triazolinium-4-yl, --.
Line 51, "N-($C_1$-$C_4$)alkylpyridinium4-yl," should read -- N-($C_1$-$C_4$) alkylpyridinium-4-yl, --.
Line 53, "N-(2-hydroxyethyl)pyridinium4-yl," should read -- N-(2-hydroxyethyl) pyridinium-4-yl, --.

<u>Column 81,</u>
Line 39, "$R_4$is" should read -- $R_4$ is --.
Line 59, "-$OCH_2$(CO)$OCH_3$group;" should read -- -$OCH_2$(CO)$OCH_3$ group; --.

UNITED STATES PATENT AND TRADEMARK OFFICE
CERTIFICATE OF CORRECTION

PATENT NO. : 6,544,298 B1
DATED : April 8, 2003
INVENTOR(S) : Laurent Vidal et al.

It is certified that error appears in the above-identified patent and that said Letters Patent is hereby corrected as shown below:

Column 84,
Lines 26-27, "1-[(2-Hydroxy-4-acetylaminophenylcarbamoyl) methyl]-1,4-dimethylpiperazin-1- ium" should read-- 1-[(2-Hydroxy-4-acetylaminophenylcarbamoyl) methyl]-1,4-dimethylpiperazin-l-ium --.
Lines 28-29, " 1-[(2-Hydroxy-4-methoxycarbonylaminophenylcarbarnoyl) methyl]-1,4-dimethylpiperazin-l-ium" should read -- 1-[(2-Hydroxy-4-methoxycarbonylaminophenylcarbamoyl) methyl]-1,4-dimethylpiperazin-1-ium --.

Column 88,
Line 6, "dying" should read -- dyeing --.
Line 24, "weight of th" should read -- weight of the --.

Column 96,
Line 57, "to6-membered" should read -- to 6-membered --.

Column 98,
Line 67, after "are each chosen", insert -- from --.

Column 109,
In the structure between lines 42-49,

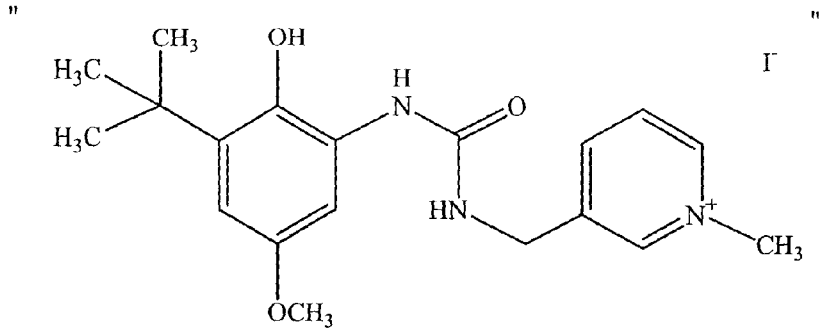

UNITED STATES PATENT AND TRADEMARK OFFICE
CERTIFICATE OF CORRECTION

PATENT NO. : 6,544,298 B1
DATED : April 8, 2003
INVENTOR(S) : Laurent Vidal et al.

It is certified that error appears in the above-identified patent and that said Letters Patent is hereby corrected as shown below:

should read

-- 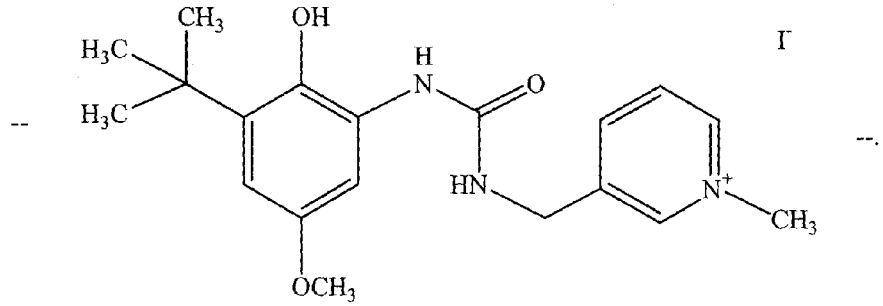 --.

Signed and Sealed this

Seventh Day of October, 2003

JAMES E. ROGAN
*Director of the United States Patent and Trademark Office*